(12) United States Patent
McLoughlin et al.

(10) Patent No.: US 9,764,084 B2
(45) Date of Patent: Sep. 19, 2017

(54) AUTO-INJECTOR

(75) Inventors: Martin John McLoughlin, Hemel Hempstead (GB); Darrell P. Morgan, Sonning Common (GB); Michael James David Heald, Berkshire (GB); Kevin Richard Lozeau, Black Rock (AU); Agnete Enga, Oslo (NO); Heather Martin, Barcelona (ES); Eric Freitag, Brooklyn, NY (US); Daniel Formosa, Piermont, NY (US); Brian Lipford, Baltimore, MD (US); Jake Cowperthwaite, Baltimore, MD (US); Alex Flamm, Baltimore, MD (US); Ilario Melzi, Milan (IT)

(73) Assignee: UCB BIOPHARMA SPRL, Bussels (BE)

( * ) Notice: Subject to any disclaimer, the term of this patent is extended or adjusted under 35 U.S.C. 154(b) by 523 days.

(21) Appl. No.: 14/123,047

(22) PCT Filed: Jun. 4, 2012

(86) PCT No.: PCT/IB2012/001394
§ 371 (c)(1),
(2), (4) Date: Jul. 9, 2014

(87) PCT Pub. No.: WO2012/164402
PCT Pub. Date: Dec. 6, 2012

(65) Prior Publication Data
US 2014/0358072 A1 Dec. 4, 2014

Related U.S. Application Data

(60) Provisional application No. 61/492,530, filed on Jun. 2, 2011.

(51) Int. Cl.
*A61M 37/00* (2006.01)
*A61M 5/145* (2006.01)
(Continued)

(52) U.S. Cl.
CPC ...... *A61M 5/14546* (2013.01); *A61M 5/1452* (2013.01); *A61M 5/158* (2013.01);
(Continued)

(58) Field of Classification Search
CPC .............. A61M 5/3204; A61M 5/3202; A61M 2205/586; A61M 2005/3215;
(Continued)

(56) References Cited

U.S. PATENT DOCUMENTS

| 2,966,910 A | 1/1961 | Camber |
| 3,395,704 A | 8/1968 | Fray et al. |

(Continued)

FOREIGN PATENT DOCUMENTS

| DE | 201009001836 U1 | 5/2009 |
| EP | 0 518 416 A1 | 12/1992 |

(Continued)

OTHER PUBLICATIONS

OHIM Design Registration Registered May 19, 2011, Registration No. 001277941-001.
(Continued)

*Primary Examiner* — Emily Schmidt
(74) *Attorney, Agent, or Firm* — Muncy, Geissler, Olds & Lowe, P.C.

(57) ABSTRACT

There is provided an auto-injector for a syringe that is suitable for use in the injected delivery of drug to a patient. The auto-injector comprises a cassette unit arranged for receipt of a syringe provided with a needle cover and removable cap. The auto-injector also comprises a drive unit arranged for docking receipt of the cassette unit at a docking position and a drive arrangement. The drive unit is provided with a timer that starts a time count on removal of the removable cap and needle cover from the cassette unit.

17 Claims, 53 Drawing Sheets

(51) Int. Cl.
*A61M 5/20* (2006.01)
*A61M 5/32* (2006.01)
*A61M 5/158* (2006.01)
*A61M 5/172* (2006.01)
*A61M 5/50* (2006.01)
*A61M 5/315* (2006.01)
*A61M 5/31* (2006.01)

(52) U.S. Cl.
CPC .............. *A61M 5/172* (2013.01); *A61M 5/20* (2013.01); *A61M 5/3134* (2013.01); *A61M 5/3137* (2013.01); *A61M 5/3202* (2013.01); *A61M 5/326* (2013.01); *A61M 5/3213* (2013.01); *A61M 5/5086* (2013.01); *A61M 5/3129* (2013.01); *A61M 5/31511* (2013.01); *A61M 5/3204* (2013.01); *A61M 2005/206* (2013.01); *A61M 2005/3139* (2013.01); *A61M 2005/3152* (2013.01); *A61M 2005/3215* (2013.01); *A61M 2202/04* (2013.01); *A61M 2205/27* (2013.01); *A61M 2205/276* (2013.01); *A61M 2205/33* (2013.01); *A61M 2205/50* (2013.01); *A61M 2205/502* (2013.01); *A61M 2205/505* (2013.01); *A61M 2205/583* (2013.01); *A61M 2205/584* (2013.01); *A61M 2205/586* (2013.01); *A61M 2205/8206* (2013.01); *F04C 2270/0421* (2013.01)

(58) Field of Classification Search
CPC ............ A61M 5/3134; A61M 2205/60; A61M 2205/6018; A61M 2205/6063; A61M 2205/6072
See application file for complete search history.

(56) References Cited

U.S. PATENT DOCUMENTS

| | | | |
|---|---|---|---|
| 4,950,246 A * | 8/1990 | Muller | A61M 5/1452 128/DIG. 1 |
| 5,662,617 A | 9/1997 | Odell et al. | |
| D439,657 S | 3/2001 | Bridle | |
| 6,368,307 B1 | 4/2002 | Ziemba et al. | |
| 6,558,353 B2 | 5/2003 | Zohmann | |
| D484,244 S | 12/2003 | Starnes | |
| 6,869,418 B2 | 3/2005 | Marano-Ford | |
| D543,273 S | 5/2007 | Young et al. | |
| 7,811,260 B2 | 10/2010 | Miller et al. | |
| D636,088 S | 4/2011 | Loew et al. | |
| D650,070 S | 12/2011 | Mori | |
| D652,512 S | 1/2012 | Sherwood et al. | |
| D652,513 S | 1/2012 | Sherwood et al. | |
| D652,919 S | 1/2012 | Sherwood et al. | |
| 8,277,437 B2 | 10/2012 | Saal et al. | |
| D671,638 S | 11/2012 | Young et al. | |
| 8,454,560 B2 | 6/2013 | Strobl | |
| 8,469,922 B2 | 6/2013 | Langley et al. | |
| 8,591,463 B1 | 11/2013 | Cowe | |
| D695,395 S | 12/2013 | Tani et al. | |
| D695,396 S | 12/2013 | Tani et al. | |
| D696,770 S | 12/2013 | Schneider et al. | |
| 8,834,429 B2 | 9/2014 | Grant et al. | |
| D724,203 S | 3/2015 | McLoughlin et al. | |
| D726,901 S | 4/2015 | McLoughlin et al. | |
| D726,902 S | 4/2015 | McLoughlin et al. | |
| D755,956 S | 5/2016 | McLoughlin et al. | |
| 2003/0050602 A1 | 3/2003 | Pettis et al. | |
| 2003/0225358 A1 | 12/2003 | Berman et al. | |
| 2004/0062148 A1* | 4/2004 | Skyggebjerg | A61J 7/0481 368/107 |
| 2005/0261693 A1 | 11/2005 | Miller et al. | |
| 2006/0270986 A1 | 11/2006 | Hommann et al. | |
| 2007/0239117 A1 | 10/2007 | Chelak et al. | |
| 2008/0171983 A1 | 7/2008 | Knutson | |
| 2008/0287785 A1 | 11/2008 | Saitoh et al. | |
| 2008/0312602 A1 | 12/2008 | Barrow-Williams et al. | |
| 2009/0182284 A1 | 7/2009 | Morgan | |
| 2009/0234297 A1 | 9/2009 | Jennings | |
| 2010/0016793 A1 | 1/2010 | Jennings et al. | |
| 2010/0016795 A1 | 1/2010 | McLoughlin | |
| 2010/0137801 A1 | 6/2010 | Streit et al. | |
| 2010/0185148 A1 | 7/2010 | Gillespie, III et al. | |
| 2010/0268169 A1 | 10/2010 | Llewellyn-Hyde et al. | |
| 2010/0298780 A1 | 11/2010 | Laiosa | |
| 2011/0009830 A1 | 1/2011 | Kosinski et al. | |
| 2011/0224616 A1 | 9/2011 | Slate et al. | |
| 2012/0053528 A1 | 3/2012 | Bollenbach et al. | |
| 2013/0221097 A1 | 8/2013 | Day et al. | |
| 2013/0226139 A1 | 8/2013 | Day et al. | |
| 2013/0281936 A1 | 10/2013 | Kemp et al. | |
| 2014/0018744 A1 | 1/2014 | Holmqvist | |
| 2014/0358072 A1 | 12/2014 | McLoughlin et al. | |
| 2014/0358083 A1 | 12/2014 | McLoughlin et al. | |
| 2015/0045734 A1 | 2/2015 | McLoughlin et al. | |
| 2015/0165135 A1 | 6/2015 | McLoughlin et al. | |
| 2015/0182691 A1 | 7/2015 | McLoughlin et al. | |
| 2015/0202374 A1 | 7/2015 | McLoughlin et al. | |
| 2015/0258278 A1 | 9/2015 | McLoughlin et al. | |
| 2017/0000955 A1 | 1/2017 | McLoughlin et al. | |
| 2017/0007763 A1 | 1/2017 | McLoughlin et al. | |

FOREIGN PATENT DOCUMENTS

| | | |
|---|---|---|
| EP | 0518416 A1 | 12/1992 |
| EP | 0 824 923 A1 | 2/1998 |
| EP | 0824923 A1 | 2/1998 |
| EP | 0 897 728 A1 | 2/1999 |
| EP | 0897728 A1 | 2/1999 |
| EP | 2384778 A1 | 8/2010 |
| GB | 2 437 922 A | 11/2007 |
| GB | 2437922 A | 11/2007 |
| GB | 2 438 593 A | 12/2007 |
| GB | 2438593 A | 12/2007 |
| GB | 2467637 A | 8/2010 |
| WO | WO 01/37905 A2 | 5/2001 |
| WO | WO-01/37905 A2 | 5/2001 |
| WO | WO 02/09797 A1 | 2/2002 |
| WO | WO-02/09797 A1 | 2/2002 |
| WO | WO 02/100467 A2 | 12/2002 |
| WO | WO-02/100467 A2 | 12/2002 |
| WO | WO 03/101368 A2 | 12/2003 |
| WO | WO-03/101368 A2 | 12/2003 |
| WO | WO 03/101527 A1 | 12/2003 |
| WO | WO-03/101527 A1 | 12/2003 |
| WO | WO 2004/043524 A1 | 5/2004 |
| WO | WO 2005/097233 A2 | 10/2005 |
| WO | WO-2005/097233 A2 | 10/2005 |
| WO | WO-2006/091695 A1 | 8/2006 |
| WO | WO 2006/091695 A1 | 8/2006 |
| WO | WO 2006/108026 A2 | 10/2006 |
| WO | WO-2006/108026 A2 | 10/2006 |
| WO | WO 2009/040603 A1 | 4/2009 |
| WO | WO-2009/040603 A1 | 4/2009 |
| WO | WO 2009/066130 A1 | 5/2009 |
| WO | WO 2009/081103 A1 | 7/2009 |
| WO | WO-2009/081103 A1 | 7/2009 |
| WO | WO 2009/087355 A1 | 7/2009 |
| WO | WO-2009/087355 A1 | 7/2009 |
| WO | WO 2009/090499 A2 | 7/2009 |
| WO | WO-2009/090499 A2 | 7/2009 |
| WO | WO-2009/143255 A1 | 11/2009 |
| WO | WO 2009/143255 A1 | 11/2009 |
| WO | WO-2010/043533 A1 | 4/2010 |
| WO | WO 2010/043533 A1 | 4/2010 |
| WO | WO2010/097116 A1 | 9/2010 |
| WO | WO-2010/136076 A1 | 12/2010 |
| WO | WO 2010/136076 A1 | 12/2010 |
| WO | WO-2010/136078 A1 | 12/2010 |
| WO | WO 2010/136078 A1 | 12/2010 |
| WO | WO 2010/139635 A1 | 12/2010 |
| WO | WO-2010/139635 A1 | 12/2010 |
| WO | WO 2010/139793 A1 | 12/2010 |
| WO | WO-2010/139793 A1 | 12/2010 |

(56) References Cited

FOREIGN PATENT DOCUMENTS

| WO | WO-2010/147553 A1 | 12/2010 |
|----|-------------------|---------|
| WO | WO 2010/147553 A1 | 12/2010 |
| WO | WO 2011/032960 A1 | 3/2011 |
| WO | WO-2011/032960 A1 | 3/2011 |
| WO | WO-2011/051366 A2 | 5/2011 |
| WO | WO 2011/051366 A2 | 5/2011 |
| WO | WO 2011/141907 A1 | 11/2011 |
| WO | WO-2011/141907 A1 | 11/2011 |
| WO | WO 2012/064258 A1 | 5/2012 |
| WO | WO-2012/064258 A1 | 5/2012 |
| WO | WO 2012/145685 A1 | 10/2012 |
| WO | WO 2012/164397 A1 | 12/2012 |
| WO | WO 2013/006119 A1 | 1/2013 |
| WO | WO 2013/085454 A1 | 6/2013 |
| WO | WO 2014/154498 A1 | 10/2014 |

OTHER PUBLICATIONS

International Search Report/Written Opinion PCT/IB2012/001231 dated Nov. 15, 2012.
International Search Report/Written Opinion PCT/IB2012/001705 dated Dec. 4, 2012.
International Search Report/Written Opinion PCT/IB2012/001150 dated Dec. 7, 2012.
International Search Report/Written Opinion PCT/IB2012/001172 dated Dec. 7, 2012.
International Search Report/Written Opinion PCT/IB2012/001394 dated Dec. 7, 2012.
International Search Report/Written Opinion PCT/IB2012/001426 dated Dec. 7, 2012.
International Search Report/Written Opinion PCT/IB2012/001507 dated Feb. 4, 2013.
International Search Report/Written Opinion PCT/IB2012/002105 dated Feb. 4, 2013.
International Search Report/Written Opinion PCT/IB2012/001147 dated Feb. 11, 2013.
International Search Report/Written Opinion PCT/EP2013/065940 dated Nov. 4, 2013.
International Search Report/Written Opinion PCT/EP2013/065939 dated Nov. 18, 2013.
International Search Report/Written Opinion PCT/EP2013/065934 dated Nov. 22, 2013.
International Search Report/Written Opinion PCT/EP2013/065938 dated Nov. 29, 2013.
International Search Report/Written Opinion PCT/EP2015/051253 dated Jul. 15, 2015.
International Search Report/Written Opinion PCT/EP2015/051257 dated Mar. 23, 2015.
International Search Report/Written Opinion PCT/EP2015/051258 dated Sep. 15, 2015.
OHIM Design Registration Registered May 19, 2011, Reg. No. 001277941-001.

\* cited by examiner

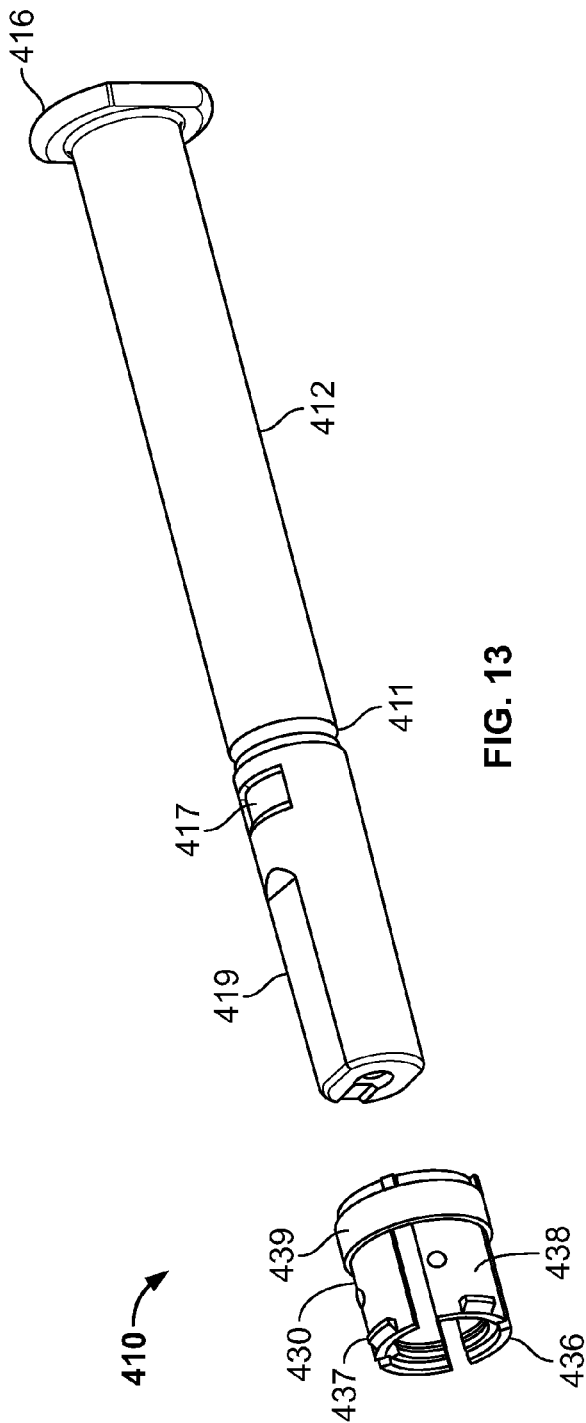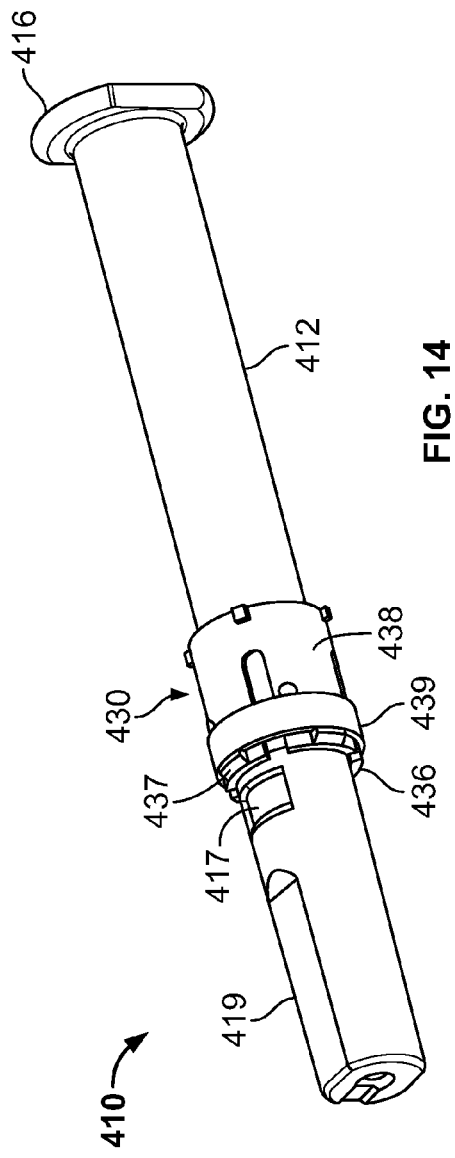

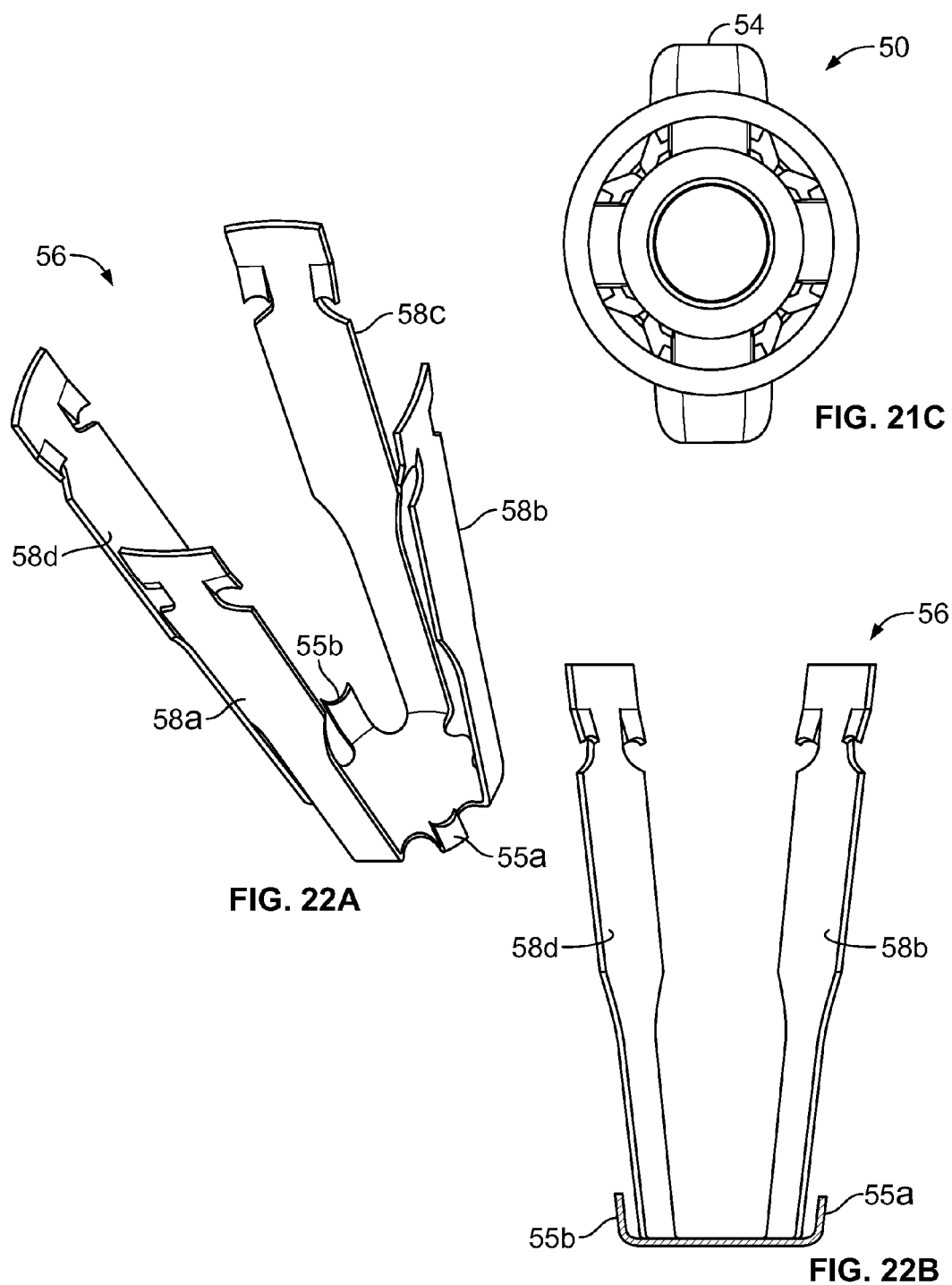

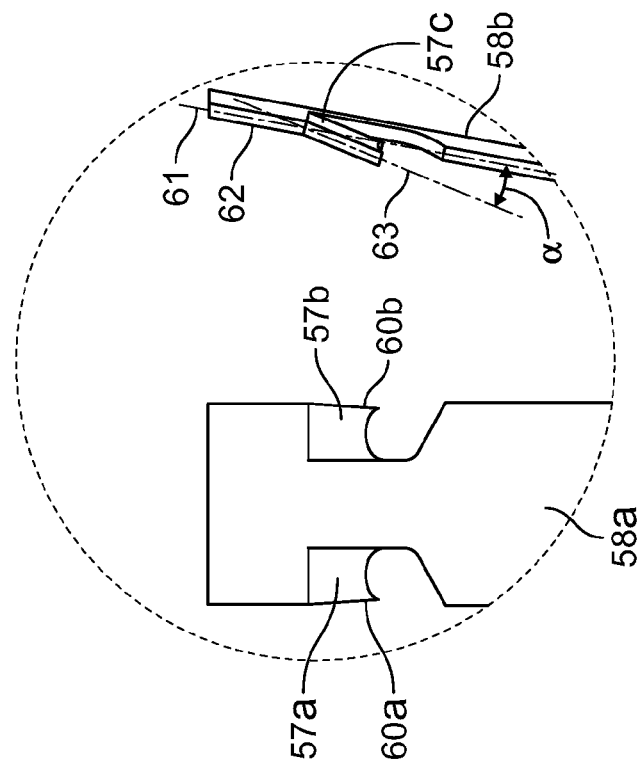
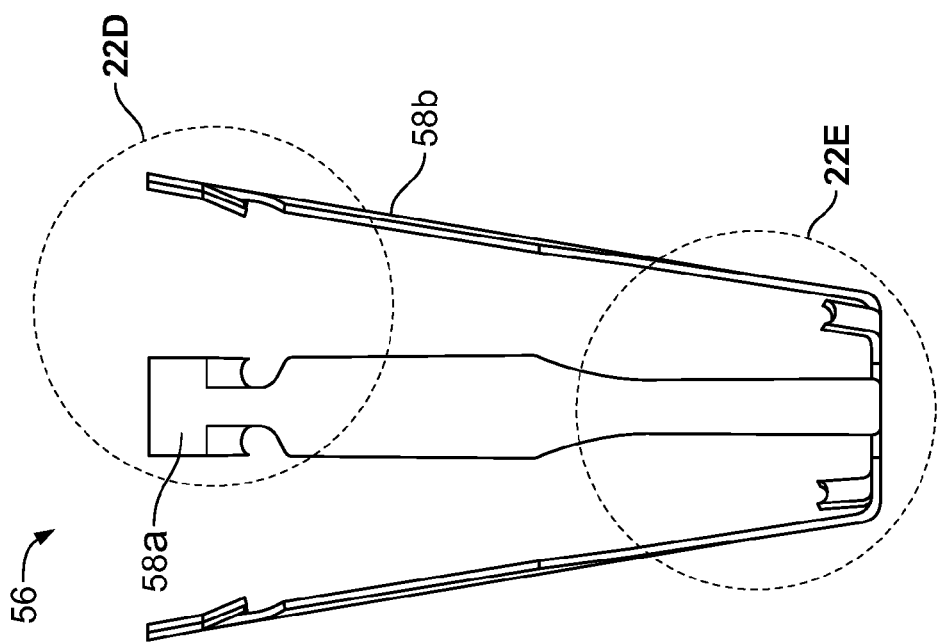
FIG. 22D
FIG. 22C

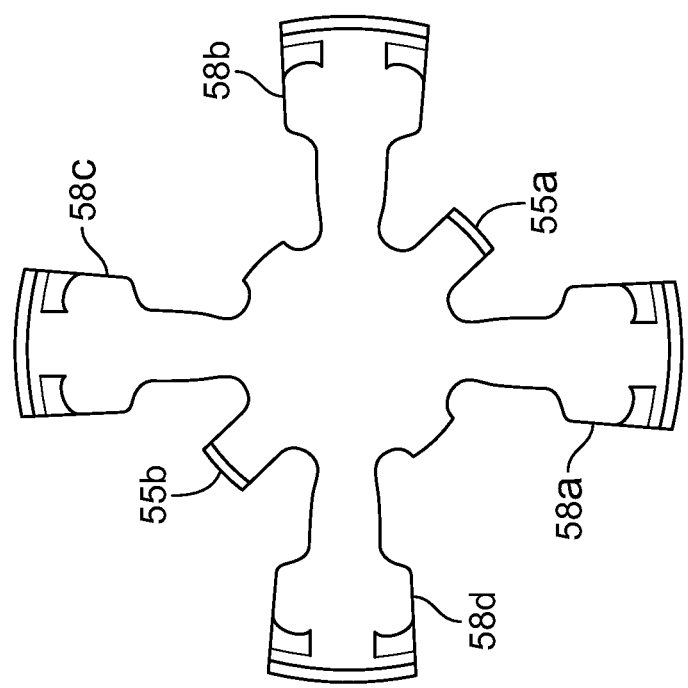
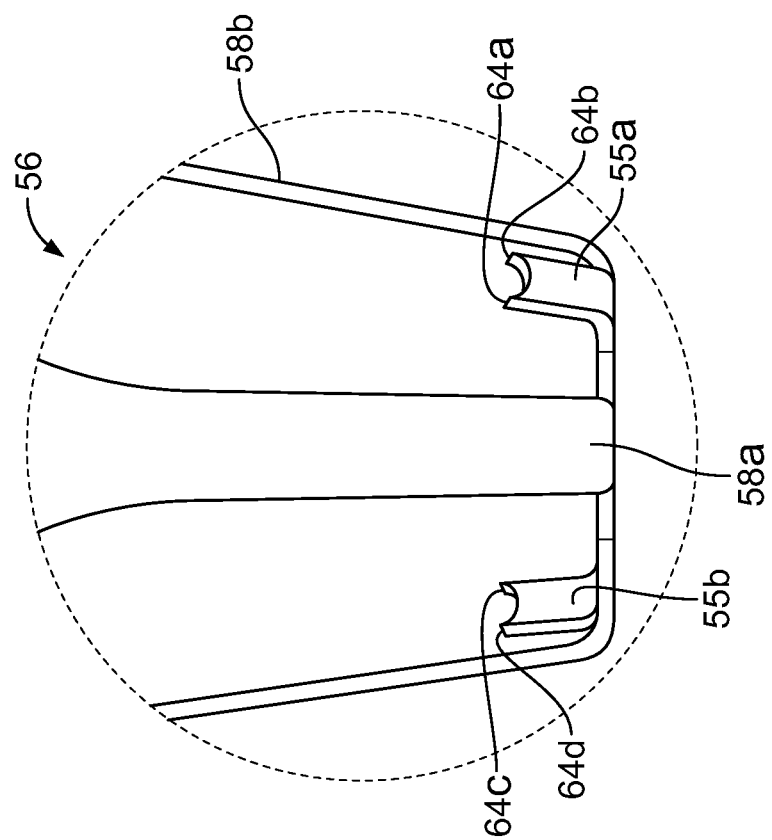
FIG. 22F
FIG. 22E

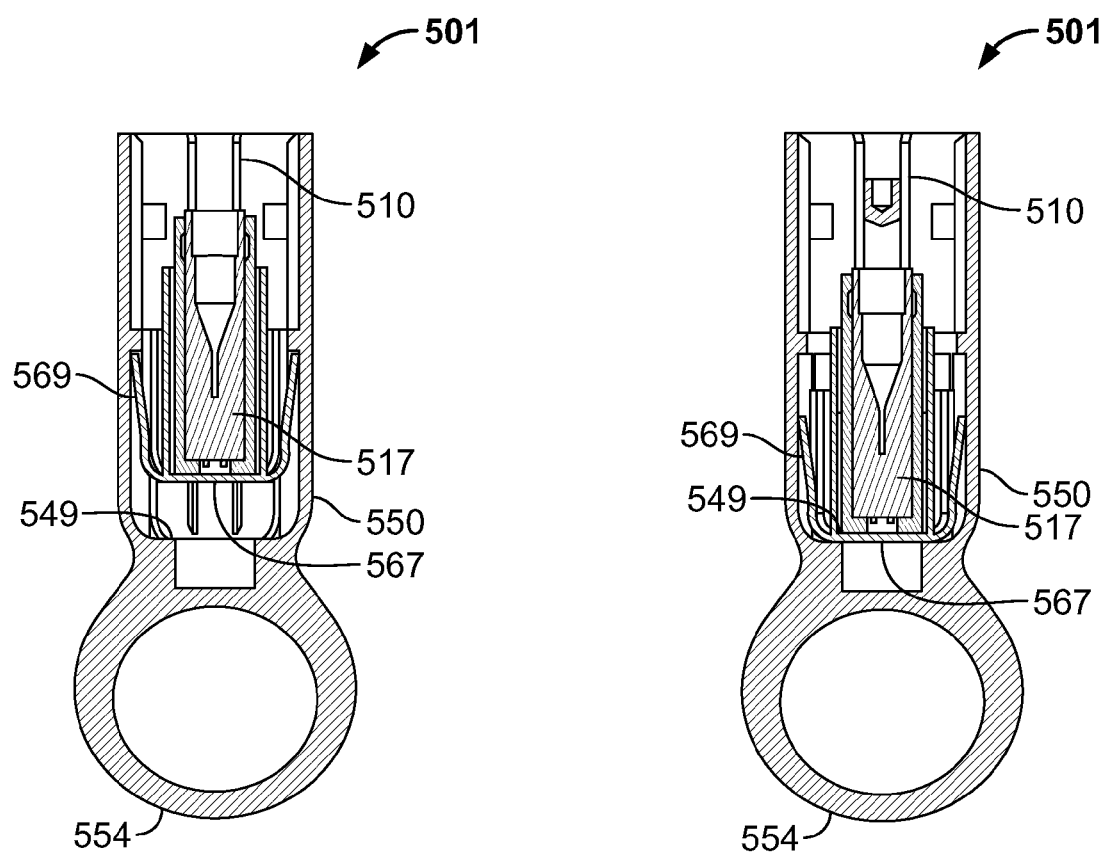
FIG. 27A    FIG. 27B

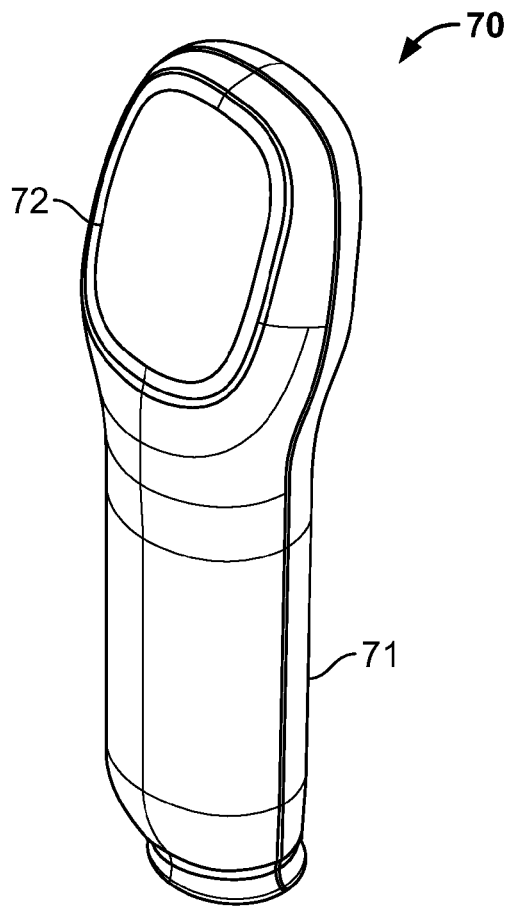
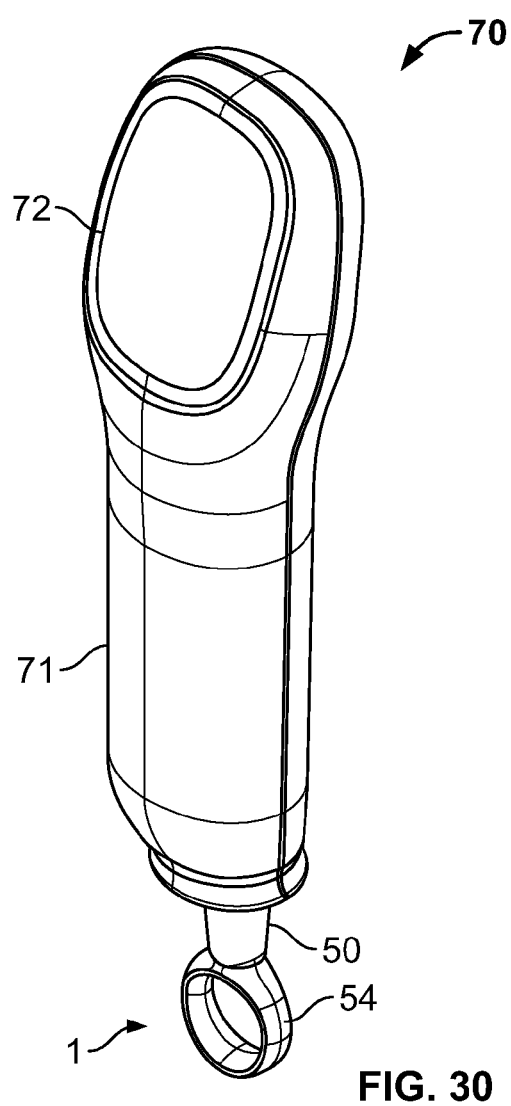
FIG. 29
FIG. 30

AUTO-INJECTOR

CROSS-REFERENCE TO RELATED APPLICATION

This application claims the benefit of U.S. Provisional Patent Application No. 61/492,530, filed Jun. 2, 2011, which is hereby incorporated by reference herein in its entirety.

BACKGROUND

The present invention relates to an auto-injector device for receipt of a syringe that is suitable for use in the injected delivery of a drug formulation to a patient.

It is well-known to use syringes for the delivery of injectable liquid drug formulation to a patient. Syringes rely on puncturing of the patient's skin by a hollow needle through which the injectable liquid drug (e.g. in solution or suspension form) is delivered to the muscle or tissue of the patient. Typically, syringes comprise a barrel for containing a volume of the liquid drug; a hollow needle defining a needle tip for dispensing of the liquid; and a plunger that is axially movable within the barrel.

It is also well-known to provide auto-injectors for use with syringes. Such auto-injectors typically comprise a body for housing the syringe and an actuating mechanism, which is triggered in use, to allow for automatic delivery of the liquid drug formulation from the syringe. Actuating mechanisms typically comprise a source of drive (e.g. a strong spring) for drivable movement of a drive transfer element (e.g. a plunger rod) that transfers drive to the plunger for axial movement thereof within the syringe barrel. Such movement of the plunger results in the plunged driving of the liquid drug from the syringe barrel to the hollow needle for dispensing to the patient via the needle tip thereof.

For safety and hygiene reasons, it is desirable that the hollow needle does not protrude from the housing of the auto-injector other than when expelling the liquid drug formulation during an injection procedure. Thus, auto-injectors have been developed in which, the housing is arranged such that a needle receiving part allows for the needle of the syringe to be axially moveable therein from a first (i.e. rest) position in which the hollow needle is shrouded by the needle receiving part to a second (i.e. use) position in which at least the tip of the needle protrudes from that needle receiving part of the housing for penetrating the skin of the patient to an injection position. Only when the needle is at such injection position should it be possible for drug delivery to commence. Thus, auto-injectors have been developed which provide a two stage actuating mechanism, which first acts to transfer drive force to move the syringe from the 'rest' to the 'use' position, and which only then secondly acts to transfer drive force to the plunger for expelling of liquid drug contents from the syringe barrel.

The majority of auto-injectors are configured as a single device that incorporates both syringe and actuating mechanism in the same device housing. It is common for such devices to be arranged to be disposable such that following injected delivery of the liquid drug formulation, and typically also following retraction of the syringe back into the housing, the whole device may be safely disposed of.

SUMMARY

It has been proposed to configure auto-injectors to include an electrically powered source of drive. Such configurations are particularly suitable for use by patients whose manual dexterity is so compromised (e.g. due to severe arthritis) that electrical powering is of real practical assistance. The use of electrically powered drive systems can also allow for more complex drive arrangements (e.g. two speed injection procedures) to be engineered. Furthermore, electrical powered devices can also be arranged to include electrical control systems and electronic data management systems including those that provide information and feedback to the patient by means of a suitable user interface.

In some situations, it is undesirable for an electrically powered auto-injector to be fully disposable. Auto-injectors disclosed herein, in certain embodiments, include both a re-useable drive unit comprising an electrically powered source of axial drive and a cassette unit comprising a syringe, which releasably interfits with the drive unit and can be arranged to be disposable. The housing of the drive unit defines a docking cavity arranged for docking receipt of the cassette unit at a docking position. Such auto-injectors may be 'environmentally friendly,' where the majority of components are retained to be used for further injection procedures. It also allows for the drive unit to be fitted with additional features such as electronics, which may not be cost effective on a completely disposable device.

The cassette unit comprises a cassette unit housing defining a cassette unit housing cavity and a needle projection aperture. The cassette unit housing cavity is arranged for receipt of a standard syringe comprising a barrel for containing a volume of a liquid drug formulation, a hollow needle at a front end of said barrel defining a needle tip for dispensing of the liquid drug formulation and a plunger that is axially movable within the barrel. Either the syringe or the cassette unit and syringe held thereby is movable within the drive unit housing from a rest position, in which the needle tip of the syringe is within the drive unit housing to a use position, in which the needle tip protrudes from a needle delivery aperture of the drive unit housing. The cassette unit is also provided with a removable cap that fits over and thereby, acts such as to close off, the needle projection aperture. Connecting to the removable cap, there is also provided a needle cover defining a needle sheath arranged in a sheathing configuration for sheathing of said needle tip.

The drive unit includes a drive arrangement comprising an electrically powered source of axial drive. In certain implementations, the drive unit includes a first drive transfer element for transferring the axial drive to the cassette unit for advancing the syringe to said use position, and a second drive transfer element for subsequently transferring the axial drive to the plunger of the syringe for moving the plunger into the barrel of the syringe to eject at least part of the volume of liquid drug formulation.

One problem associated with the use of such an auto-injector having a re-useable drive unit and a separate cassette unit is to ensure that the injection procedure is carried out in a timely manner on removal of the cap and needle cover from the cassette unit, thereby unsheathing the needle tip and exposing it to air and possible contaminants including microbial contaminants. Particular aspects of the problem include the preventing of drying out of the drug formulation contents of the syringe and/or preventing degradation (e.g. as a result of oxidative processes) of the drug formulation on exposure to air or to microbial contaminants.

In solution, the drive unit of the present auto-injector is provided with a timer that starts a time count on removal of the removable cap and needle cover from the cassette unit. In embodiments, the drive unit includes an electronic display and the time count is displayed on the electronic display so that the user is given an indication of time elapsed following removal of the cap and needle cover from the cassette unit. In embodiments, the timer counts upwards (i.e. from zero) on removal of the removable cap and needle cover). In other embodiments, the timer counts downwards (i.e. from a pre-determined time count) on removal of the removable cap and needle cover. Thus, for example an indication of time remaining to safely use the device may be calculated and in embodiments, alternatively or additionally presented to the user on the display.

In developments of the solution, the timer is arranged such that on reaching a certain, pre-determined time count a stop command to stop the drive functioning of the drive unit is generated. The timer and stop command therefore acts to ensure that drug is delivered to the patient within a set time limit following removal of the removable cap and needle cover from the syringe of the cassette unit.

In further developments of the solution, one or more cap removal sensors are provided to detect removal of the removable cap and needle cover from the cassette unit. Thus, the device may be arranged such that the one or more cap removal sensors communicate with the timer (e.g. via an electronic data unit or control unit) to send a cap removal detection signal to the timer to initiate the time count thereof.

According to one aspect of the present invention there is provided an auto-injector comprising
(a) a cassette unit comprising
a cassette unit housing defining a cassette unit housing cavity and a needle projection aperture;
said cassette unit housing cavity arranged for receipt of a syringe comprising
  a barrel for containing a volume of a liquid drug formulation;
  a hollow needle at a front end of said barrel, said hollow needle defining a needle tip for dispensing of said liquid drug formulation; and
  a plunger that is axially movable within the barrel;
a removable cap that fits over and thereby, acts such as to close off, the needle projection aperture; and
connecting to said removable cap, a needle cover defining a needle sheath for sheathing of said needle tip; and
(b) a drive unit comprising
a drive unit housing defining a docking cavity and a needle delivery aperture, wherein said docking cavity is arranged for docking receipt of the cassette unit at a docking position, whereupon said cassette unit and/or said syringe is movable from a rest position, in which the needle tip of the syringe is within the drive unit housing to a use position, in which the needle tip protrudes from said needle delivery aperture; and
a drive arrangement, said drive arrangement comprising
  one or more electrically powered sources of axial drive;
  a first drive transfer element for transferring said axial drive to the cassette unit and/or to the syringe for advancing the syringe to said use position; and
  a second drive transfer element for subsequently transferring the axial drive to said plunger of the syringe for moving the plunger into the barrel of the syringe to eject at least part of said volume of liquid drug formulation,
wherein the drive unit is provided with a timer that starts a time count on removal of the removable cap and needle cover from the cassette unit.

In embodiments, the timer is arranged such that on reaching a certain, pre-determined time count a stop command to stop the drive functioning of the drive unit is generated.

In embodiments, the timer is arranged such that on reaching a certain, pre-determined time count an alarm command to initiate an audible alarm of the drive unit is generated.

In embodiments, one or more cap removal sensors are provided to detect removal of the removable cap and needle cover from the cassette unit. In embodiments, the one or more cap removal sensors communicate with the timer to send a cap removal detection signal to the timer to initiate the time count thereof.

In embodiments, the drive unit includes an electronic display and the time count is displayed on the electronic display.

These and other embodiments of the present invention are set forth in the later description, which describes for illustrative purposes only various embodiments thereof.

In relation to aspects of the auto-injector device described herein the term 'forward' is used to mean that end of the device, which locates closest to the injection site in use (i.e. the needle tip end) and the term 'rear' or 'rearward' is used to mean that end of the device, which locates furthest from the injection site in use.

There is provided an auto-injector device that is arranged for use with a syringe that contains a liquid drug formulation. The syringe is arranged to be suitable for use in the injected delivery of the liquid drug formulation to a patient.

The auto-injector comprises both a drive unit and a cassette unit receivable by the drive unit. The individual drive unit and cassette unit parts thereof comprise further separate aspects of the present invention. In embodiments the drive unit and cassette unit are provided as a kit of parts.

Cassette Unit

The cassette unit comprises a cassette unit housing defining a cassette unit housing cavity. The cassette unit housing cavity is arranged for receipt of a syringe and is therefore typically sized and shaped for this purpose. The cassette unit housing may be arranged as a single part or a multi-part (e.g. two part) cassette unit housing assembly.

In embodiments, the syringe is held in generally fixed fashion within the cassette unit housing. In other embodiments, the syringe is movable within the cassette unit housing such as in a direction parallel with or along the drive axis.

In embodiments, wherein the syringe is held in generally fixed fashion within the cassette unit housing, at least the needle tip of the syringe normally protrudes out of the cassette unit housing cavity such as from a needle projection aperture thereof.

In other embodiments, the syringe is movable within the cassette unit housing from a first position, in which the needle tip of the syringe is within the cassette unit housing to a second position, in which at least the needle tip protrudes from a needle projection aperture thereof.

The syringe that is receivable within the cassette unit housing cavity comprises a syringe barrel for holding a volume of the liquid drug formulation; a hollow needle at a front end of the barrel, the hollow needle defining a needle tip for dispensing of said liquid drug formulation; and a plunger (e.g. in the form of a rubber stopper) that is axially movable within the syringe barrel. The syringe plunger is movable axially within the barrel so as to enable the liquid drug formulation to be expelled from the barrel and thence through the hollow needle via the dispensing tip for injection into the patient. The syringe barrel is typically, comprised of glass but may also be comprised of a relatively hard plastic polymer such as hardened polyethylene, polycarbonate or cyclic olefin polymers.

In embodiments, the plunger is comprised of a natural or synthetic polymer friction material, which frictionally interacts with the side wall of the syringe barrel. Suitable plunger materials include natural or synthetic rubbers or elastomeric materials.

In more detail, the syringe barrel is selected such as to define a barrel chamber for containing a suitable volume of the liquid drug formulation. In embodiments, that suitable volume is selected to correspond to a single dose of the drug formulation to be delivered to the patient. In other words, delivery of that single dose involves expelling all of the liquid drug formulation contents of the barrel chamber through the hollow needle for injection into the patient.

In embodiments, the rear end of the syringe barrel is provided with an end flange. In embodiments, the forward end of the syringe barrel is shaped to provide a shoulder. In embodiments, forward of that shoulder the syringe narrows further into a neck, which typically forms the needle-holding part thereof.

In embodiments, the needle barrel is provided with a barrel sleeve that is arranged to fit over part or all of the length of the needle barrel. The barrel sleeve may also extend out beyond the syringe barrel to wholly or partly enclose a length of the forward shoulder of the syringe barrel and of the hollow needle that extends from (the forward shoulder) of the syringe barrel.

In embodiments, the cassette unit is arranged to accommodate multiple syringe sizes. Common sizes of syringe include the 2.25 ml syringe and the 1 ml 'long' syringe, which has a smaller syringe barrel diameter.

In embodiments, accommodation of multiple syringe sizes within the same cassette unit geometry is achievable by providing suitable adapters to the barrel of the syringe. In embodiments, sleeve form adapters are employed.

In embodiments, the sleeve form adapter is arranged for receipt by the syringe barrel and fits at least partly over the flange of the rear end of the syringe barrel. In embodiments, the sleeve adapter is arranged for snap fitting over the end flange of the syringe. In embodiments, the flange is effectively capped by the relevant 'end flange' part of the sleeve form adapter.

In embodiments, a major portion of the syringe barrel and end flange thereof is in use, sleeved by the sleeve form adapter. The overall effect of this sleeving of a major portion is firstly to increase the effective diameter of the syringe barrel; secondly to provide strengthening reinforcement to the end flange; and thirdly to increase the effective length of the syringe.

In one particular embodiment, the cassette unit is shaped and sized based on the geometry of the larger 2.25 ml syringe. A syringe having a smaller outer dimension (e.g. a 1 ml 'long' syringe) may then be accommodated in this same cassette unit by use of a sleeve adapter that effectively functions to adapt the outer syringe geometry (e.g. the outer diameter thereof) to closely correspond to or to be identical with that of the 2.25 ml syringe.

In embodiments, adding a sleeve adapter to the smaller diameter 1 ml 'long' syringe can make it slightly longer than the 2.25 ml syringe. In embodiments, when the cassette unit is assembled with the 2.25 ml syringe, an adapter ring may be added underneath the syringe flange to make its effective flange thickness the same as that of a smaller 1 ml syringe with a sleeve adapter.

In embodiments, the sleeve adapter is provided with one or more slits in the wall(s) of the sleeve adapter such as to define flexible fingers, which allow the adapter to flex open. In embodiments, the presence of such flexible fingers is of utility during assembly of the sleeved syringe as the needle cover (e.g. rigid needle shield), which typically has a larger diameter than the syringe barrel, passes through the centre of it when the syringe is pressed into the adapter. In embodiments, the end flange at the rear end of the syringe then snaps into the rear end of the adapter such that the syringe is locked into the adapter once assembled.

In embodiments, one or more positioning and/or retaining features are provided to the cassette unit housing for positioning and/or retaining the syringe and sleeve form adapter in the cassette unit housing cavity. In embodiments, the one or more positioning and/or retaining features comprise one or more snap features provided interiorly to the cassette unit housing.

In certain implementations, the ability of the cassette unit to accommodate syringes of different sizes confers certain advantages. In the case of drive units with a variable performance across the injection stroke it may be advantageous in some circumstances to use a syringe of larger bore diameter because the same volume of drug can be delivered from a shorter injection stroke, thereby enabling the drive unit performance to be optimized.

Similarly, for a given combination of needle and drug (same needle bore and viscosity) the volume injected per unit displacement of the plunger is greater in the case of a wider bore syringe by a factor proportional to the square of the difference in syringe diameter. A faster injection can therefore be achieved for the same plunger displacement velocity. In this case the force applied by the plunger will be greater in the larger syringe due to the increase in volumetric flow rate. This may be useful in cases where the maximum displacement velocity is limiting.

Also, the flexibility in dose delivery rate provided by variable syringe sizes may also be beneficial in optimizing the power requirements of the electrically powered drive unit. Thus, in embodiments this may limit peak current drain of the batteries thereby enabling smaller batteries to be used, maximizing the time between recharge or replacement and/or prolonging their useful life.

It has been appreciated that to reduce the risk of the syringe shattering under the loads associated with injecting the drug, it is important for a majority of the load path to travel through the shoulder at the forward end of the syringe and lesser load to pass through the flange at the rear end of the syringe.

In embodiments, the forward shoulder of the syringe is provided with one or more shoulder support features. In embodiments, the one or more shoulder support features are integral (e.g. integrally formed) with the cassette unit housing. In other embodiments, the one or more shoulder support features are defined by one or more separate shoulder support parts provided to the cassette unit.

In embodiments, the one or more shoulder support features locate (e.g. in snap-fit arrangement) between the needle cover (e.g. rigid needle shield) and the forward shoulder of the syringe. In embodiments, the sleeve adapter as described above, is provided with such one or more shoulder support features that in embodiments, snap-fit between the needle cover (e.g. rigid needle shield) and the forward shoulder of the syringe. This snap fitting is typically enabled after the syringe assembly has been pressed through the sleeve adapter during the assembly operation.

In embodiments, a clearance space is defined between the bottom of the syringe flange and the closest surface of the sleeve adapter. In embodiments, the sleeve form adapter acts to space the end flange of the syringe from the inner walls of the cassette unit housing. In embodiments, when the syringe is loaded within the cassette unit housing the flange of the syringe is spaced from the inner walls of the cassette unit housing and/or the sleeve adapter and in embodiments, is not in contact with anything.

In embodiments, a ring of compliant (e.g. resilient or flexible) material such as rubber or a suitable synthetic polymeric material is employed to bear some of the load on the flange and/or to accommodate tolerances. In embodiments, that ring of compliant material is arranged for receipt over the shoulder support feature. In embodiments, the ring of compliant material acts such as to secure the shoulder support feature in place such as by securing a snap-fit arrangement in place.

In embodiments, at least part of the syringe or syringe/sleeve adapter combination interacts with (e.g. inserts into) a constraining feature of the cassette unit housing that has a tight clearance between its inner walls and the outside diameter of the standard (e.g. 2.25 ml) syringe. In embodiments, this constraining feature of the cassette unit housing interacts with the shoulder and/or neck of the syringe. In embodiments, this feature is the only surface acting to constrain the position of the syringe within the cassette unit housing (e.g. during injection). In embodiments, the constraining feature of the cassette unit housing that constrains the syringe also prevents the sleeve adapter from flexing outwards when the injection loads are applied to the syringe. With the rear end of the sleeve adapter (e.g. any defined fingers thereof) securely snapped under the shoulder of the syringe and so prevented from flexing outwards, the syringe is effectively secured within the cassette unit housing. In embodiments, if this were not the case the force applied to the syringe during injection could push the fingers open and enable the syringe to push through.

The hollow needle defines a needle bore, which is most typically of circular cross-section and of selected bore diameter. It may be appreciated that in embodiments, the bore diameter may affect the force required to expel the liquid drug formulation through the needle and also the velocity at which the liquid drug formulation is expelled.

The selected needle bore may also, in embodiments affect the degree of patient discomfort during injection. Smaller bore diameters, typically provide more patient comfort, whereas larger bore diameters enable more rapid/lower force delivery of the liquid through the needle. A compromise is therefore needed in selecting a needle bore to provide acceptable patient comfort and liquid delivery through the needle characteristics.

Examples of typical needles that are suitable for use therein include 12.5 mm ("half inch") long thin wall needles of grade 23G, 25G or 27G. These have a needle bore of from about 0.2 to 0.4 mm such as from 0.25 to 0.35 mm. Other examples include both regular and thin wall needles used in conventional syringes including those with bevels such as 3 and 5 bevels.

The cassette unit housing and any inner cassette unit housing sub assembly thereof is shaped to define a cassette unit housing cavity within which the syringe is receivable, and in embodiments, a needle projection aperture. The cassette unit housing cavity is typically cylindrical in form, thereby matching the typically cylindrical outer profile of a syringe. The cassette unit housing cavity may be further shaped with any manner of grooves, indentations or other shaping or surface details to define a 'lock and key' relationship between the cassette unit housing and any inner cassette unit housing sub assembly thereof and the syringe. Colour guides, arrows and any other surface markings may also be employed.

Typically, the cassette unit housing and/or any inner cassette unit housing sub assembly thereof is provided with a barrel receiving part for receiving the barrel of the syringe; a plunger receiving part for receiving the plunger of the syringe; and in embodiments, a needle receiving part for receiving the hollow needle of the syringe.

In embodiments, the plunger receiving part of the cassette unit housing and/or any inner cassette unit housing sub assembly thereof allows the plunger within the syringe barrel to be received thereby and for the plunger to be movable (e.g. axially) therein from a first position to a second position, in which it is moved somewhat into the syringe barrel. During use the plunger is in embodiments, movable to a fully plunged position in which most, in embodiments all of the liquid drug formulation contents of the barrel have been expelled.

In embodiments, the needle receiving part of the cassette unit housing and/or any inner cassette unit housing sub assembly thereof includes a needle projection aperture through which the hollow needle may protrude from the housing, for example during expelling of the liquid drug formulation through the hollow needle and its needle tip for delivery to the patient.

In embodiments, the syringe is movable within the cassette unit housing cavity from a rest position, in which the needle tip is within the cassette unit housing to a use position, in which the needle tip protrudes from the needle projection aperture. In other embodiments, the syringe is in fixed relationship with the cassette housing in which, typically the needle tip protrudes from the needle projection aperture.

Where the syringe is movable in the cassette unit housing, it may be desirable for safety and hygiene reasons that the needle does not protrude from (i.e. out with) the cassette unit housing other than when expelling the liquid drug formulation during an injection procedure. Thus, the cassette unit housing and/or any inner cassette unit housing sub assembly thereof and cassette unit housing cavity defined thereby is generally arranged such that the needle receiving part thereof allows for the needle of the syringe to be axially moveable therein from a first position in which the needle is wholly housed (or shrouded) by the needle receiving part to a second position in which at least the tip of the needle protrudes from that needle receiving part of the cassette unit housing.

In embodiments, where the syringe is movable within the cassette unit the cassette unit housing includes biasing means (e.g. a spring) arranged such that the needle is normally biased towards the first position, wherein such biasing means are overcome during the actuation of the syringe (e.g. by an actuating mechanism) to allow for movement of the needle to the second position.

In embodiments, it is desirable for cassette unit housing to allow for the needle of the syringe to be retracted into the housing after use. Thus, it is desirable to be able to retract the needle back into the needle receiving part of the cassette unit housing after the injection procedure, that is to say to retract the needle from the second position to a retracted position that may in embodiments, correspond to the first position or in other embodiments, correspond to a third position, which in embodiments is further away from the needle projection aperture. A needle retract mechanism may thus, be provided to the cassette unit housing (e.g. responsive to a biasing means such as a light return spring) to retract the syringe needle back into the cassette unit housing.

In embodiments, it is desirable for the cassette unit housing to allow for the needle of the syringe to be shrouded by a needle shroud element after use. Thus, in particular it is desirable to be able to provide a means of shrouding the needle of the syringe that is moved or otherwise brought into operation after completion of the injection procedure. Such means in embodiments comprises a movable shroud element that is adapted to be movable to a shrouding configuration at the end of the injection procedure.

In embodiments, the cassette unit housing is provided with a removable cap that fits over and thereby, acts such as to close off, the needle projection aperture. It may therefore, be appreciated that when in the capped position, the removable cap acts such as to prevent ingress of contaminants into the needle receiving part of the housing.

In embodiments, the syringe further comprises a needle cover defining a needle sheath arranged in a sheathing configuration for sheathing (e.g. sealing) of the needle tip.

In embodiments, the needle sheath is comprised of a (e.g. resiliently) compressible material such as a natural or synthetic rubber material. In a storage configuration, the needle tip sticks into (e.g. is spiked or staked into) the needle sheath such that sealing of the needle tip is achieved. Usually, at least the first 3 to 4 mm of the needle tip end is so sheathed. It will be appreciated that for clinical reasons, the sealing of the needle tip acts in embodiments, such as to prevent passage of contaminant, bacterial or otherwise, through the needle tip and thus into the needle bore and syringe barrel chamber. Sterile sealing is preferred.

In embodiments, the needle cover is provided with a needle sheath cover for covering the needle sheath thereof. In embodiments, the needle sheath cover is comprised of a rigid material (e.g. polypropylene). In embodiments, the needle sheath cover is provided with one or more gripping elements (e.g. hooks) arranged for gripping of the needle sheath. In embodiments, the needle sheath is provided with one or more features arranged for receipt of the one or more gripping elements such as one or more indents, grooves or cavities.

In embodiments, the needle cover is provided to (e.g. fixed to or integral with) a removable cap for the cassette unit housing. Thus, in embodiments, the needle cover projects within the cap such that when the removable cap is in the capped position the needle sheath and any needle sheath cover therefor projects towards the needle tip of the syringe. In such embodiments, when in the capped position, the needle tip is sheathed by the needle sheath, and when the cap is removed the needle sheath and any needle sheath cover therefor are also removed such as to thereby, unsheathe the needle tip. In embodiments, the removable cap defines an essentially closed cylindrical cap chamber, optionally tapering, and the needle sheath and any needle sheath cover are provided along the axis of that cylindrical chamber.

In embodiments, the interior of the removable cap is provided with a connector defining one or more needle cover gripping elements for gripping the needle cover (i.e. gripping the needle sheath and/or any needle sheath cover therefor). In embodiments, such gripping elements are arranged for gripping of the needle cover when in the capping position. In embodiments such gripping elements are (e.g. additionally) arranged for gripping of the needle cover on removal of the cap such that removal of the cap also results in removal of the needle cover and hence, unsheathing of the needle tip. In embodiments, the needle cover gripping elements are arranged to project away from the top inner surface (e.g. of the cylindrical cap chamber) of the removable cap and towards its open end.

In embodiments, the connector comprises one or more needle cover gripping elements (e.g. gripping legs) attaching to a central hub. In embodiments, the connector is in the form of a cage-like needle cover gripper. In embodiments, each gripping element (e.g. leg) is provided (e.g. at the foot thereof) with one or more gripping protrusions such as one or more internally facing hooks or barbs. In embodiments, the internally facing hooks or barbs are disposed at an angle with respect to the gripping leg. In embodiments, the connector locates within the removable cap such that the central hub locates adjacent to or slightly spaced from the top inner cap wall or surface and the gripping legs project away from the top inner cap wall or surface and towards the open end of the cap. Other needle cover gripper arrangements are disclosed in Applicant's co-pending PCT publication no. WO2009/081103 the entire contents of which are incorporated herein by reference.

In embodiments, the removable cap is provided with a connector. The connector is shaped to fit within and engage the needle cover and to engage the inner part of the removable cap. In embodiments, the connector includes one or more needle gripper elements in the form of first legs attaching to a central hub and spaced symmetrically away from one another, each first leg having one or more internally facing barbs pointing toward a forward region of the connector and adapted to engage a proximal region of the needle cover. In embodiments, the one or more internally facing barbs are disposed at an angle with respect to the first leg. In embodiments, the connector also includes one or more second legs spaced symmetrically away from one another, each second leg having one or more externally facing barbs located in the forward region of the connector and adapted to engage a forward region of the inner part of the removable cap. In embodiments, the one or more first legs are biased initially at about 60 to 80 degrees with respect to the horizontal. Arrangements of removable cap and connector of this type are disclosed in Applicant's co-pending PCT publication no. WO2009/090499 the entire contents of which are incorporated herein by reference.

In embodiments, the geometry of the removable cap is selected to allow for the needle cover to be sufficiently aligned with the needle of the syringe so that on re-capping the needle does not undesirably catch on the needle sheath inside the needle cover. In embodiments, wherein the connector comprises one or more needle cover gripping elements (e.g. gripping legs) attaching to a central hub, Applicant has found that to assist re-sheathing of the needle cover it is desirable to position the connector within the removable cap such that the central hub is in spaced relationship to the top inner cap wall of the removable cap. When so-positioned, the gripping legs project away from the top inner cap wall and towards the open end of the cap. Applicant has found that having the central hub in somewhat spaced relationship to the top inner cap wall allows for a certain 'give' in the axial position of the needle cover such that in the event of any snagging of needle cover by the needle tip during re-sheathing, the connector and/or needle cover is free to move into the 'give' space, thereby ensuring that the snagging event does not result in any bending, or in a worst case scenario snapping, of the needle. The occurrence of any needle stick hazards during re-capping and re-sheathing is thus, minimized. In addition, the presence of 'give' space ensures that it is always possible to refit the cap, which may otherwise be prevented by needle snagging.

In embodiments, the removable cap is provided with a spacer insert and the connector is provided to (e.g. locates within) the spacer insert. In these embodiments, the function of the spacer insert is effectively to assist in defining of the 'give' space as described above. In embodiments, the spacer insert defines a central end hub and an inner boss, which extends from the central end hub to define a chamber for receiving the connector and in embodiments also, in use for receiving the needle cover as gripped by the connector. In embodiments, the spacer insert also defines an outer boss, which extends from the end hub and in embodiments, also extends about (e.g. circumferentially about) the inner boss. In embodiments, the outer boss includes crenellated portions therein. In embodiments, the outer boss defines flexible fingers, which splay out from the central end hub and thus, extend about the outer surface (e.g. of the lower part of) the outer boss. In embodiments, the flexible fingers of the outer boss locate within the crenellated portions of the outer boss. In embodiments, the spacer insert is comprised of a plastic (e.g. a plastic polymer) material and thus, may be referred to as a plastic 'outer flower' structure. In embodiments, the chamber of inner boss of the spacer insert is provided with a connector (e.g. a needle cover gripper such as in the form of a cage-like structure) and defining plural gripping elements arranged about a central hub. In embodiments, the connector is comprised of a metal and may thus, be referred to as a metal 'inner flower' structure.

To assist with re-sheathing of the needle cover on re-capping of the cassette unit after an injection procedure, the position of spacer insert and connector held there-within is in embodiments, arranged within the removable cap such that central end hub of the spacer insert is in spaced relationship to the effective end wall of the removable cap. By effective end wall it is meant either the actual end wall of the removable cap or a structure (e.g. ledge-like structure) that functions as a seat for the central end hub of the spacer insert and thus, defines the minimum spaced relationship between that central end hub and the end of the removable cap. Having the central end hub of the spacer insert in somewhat spaced relationship to the effective end wall of the removable cap allows for a certain 'give' in the axial position of the connector and needle cover gripped thereby such that in the event of any snagging of needle cover by the needle tip during re-sheathing, the spacer insert, connector and needle cover are free to move into the 'give' space, thereby ensuring that the snagging event does not result in any bending, or in a worst case scenario snapping, of the needle. The occurrence of any needle stick hazards during re-capping and re-sheathing is thus, minimized.

In embodiments, the removable cap is provided with a finger-grip feature that is sized and shaped for gripping by the finger of a user and to provide a ready means for removing the cap and needle cover attached thereto. In embodiments, the finger-grip feature is shaped to provide a ring (e.g. a gripping ring or ring pull) for ready finger gripping by the user by placing a finger or thumb inside the ring.

In embodiments, the removable cap is provided with one or more first engagement features arranged for selectively engaging one or more second engagement features of the cassette unit housing when the cap is in the capping position. Thus, in the capping position an engaging relationship may (e.g. selectively) be established between the removable cap and the cassette unit housing.

In embodiments, the first engagement features of the removable cap and the second engagement features of the cassette unit housing are arranged to have any form, which allows for engaging relationship to be established. In embodiments, latching, peg and socket and snap-fit features arranged for mutual engagement are envisaged.

In embodiments, the removable cap is provided (e.g. at the brim thereof) with an arrangement of first engagement features that are sized and shaped to extend up into the cassette unit housing when the cap is in the capping position. In embodiments, the arrangement of first engagement features is in the form of a crown of such first engagement features. In embodiments, that crown is defined by an arrangement of protruding arms having shaped tips.

In embodiments, the cassette unit housing is provided (e.g. at the forward end thereof) with an arrangement of second engagement features that are sized and shaped to extend up into the removable cap when the cap is in the capping position. In embodiments, the arrangement of second engagement features is in the form of a crown of such second engagement features. In embodiments, that crown is defined by an arrangement of protruding arms having shaped tips.

In embodiments, the first engagement features of the removable cap are arranged for engaging with features of the inner cassette unit housing and optionally, also with features of the syringe. In embodiments, that engaging is by latch engagement or snap engagement of the engagement features of the cap with features of the inner cassette unit housing and/or features of the syringe.

In embodiments, the second engagement features of the cassette unit housing are arranged for engaging with (e.g. inner) features of the removable cap. In embodiments, that engaging is by latch engagement or snap engagement of the engagement features of the cassette unit housing with features of the (e.g. inner part of the) removable cap.

In embodiments, the one or more first engagement features of the removable cap are arranged for selective engagement with the one or more second engagement features of the cassette unit housing (e.g. of the inner wall(s) thereof) such that when so-engaged rotation of the cap and hence of any needle cover attaching thereto (e.g. by means of a connector) is restricted or prevented. Such restriction/prevention of cap rotation has been found to be desirable to prevent any damage to the syringe needle within the needle cover as may potentially result from any unintended/undesirable rotation (e.g. non-symmetric or off central axis rotation) of the cap and hence connector and needle cover relative to the needle.

In embodiments, the cassette unit housing and removable cap are arranged such that when the removable cap and needle cover connecting thereto are brought into capping relationship (i.e. moved towards the capping position) the one or more first engagement features of the removable cap move into engaging relationship with the one or more second engagement features of the cassette unit housing. The establishment of this engaging relationship acts such as to prevent rotation of the cap, and hence also of the needle cover attaching thereto.

In particular embodiments, during such insertion of the removable cap into the cassette unit housing the tips of the crown of first engagement features of the removable cap snap into second engagement features provided to the walls of the inner cassette unit housing. The protruding arms of each crown of first engagement features are arranged to fit about rigid second engagement features of the cassette unit housing such as to prevent rotation of the cap, and hence also of the needle cover attaching thereto.

In embodiments, the geometry of the removable cap is selected to allow for the needle cover to be sufficiently aligned with the needle of the syringe so that on re-capping the needle does not undesirably catch on the needle sheath inside the needle cover. In embodiments, the geometry of the first engagement features of the removable cap and/or second engagement features of the cassette unit housing is selected to allow for such ease of re-capping. In embodiments, the arms of the crown of first and/or second engagement features are arranged for guiding into the cassette unit housing e.g. by a guide feature (e.g. lead-in) provided to the inner cassette unit housing. In embodiments, once the first engagement features of the removable cap begin to engage with the second engagement features of the cassette unit housing it is held concentrically enough to prevent the needle from catching on the needle sheath. This is important to ensure that on re-capping the needle cover is able to fully sheathe the used needle to minimize the occurrence of any needle stick hazards.

In embodiments, the cassette unit is provided with a cap lock (i.e. cap removal prevention) feature for selectively preventing removal of the removable cap. In embodiments, the cap lock feature is movable from a first cap locking position in which it prevents removal of the cap from the cassette unit to a second cap un-locking position in which it no longer prevents such cap removal.

In embodiments, the cap lock feature is configured as a shuttle lock, which may shuttle from the first cap locking position to the second non-locking position. In embodiments, the cap lock feature is biased to the first locking position.

In embodiments, the cap lock (i.e. cap removal prevention) feature selectively prevents removal of the removable cap until either the cassette unit locates at the docking position within the drive unit housing or until a release mechanism is activated. In embodiments, the cap lock feature of the cassette unit is only movable from the first cap locking position to the second cap non-locking position when the cassette unit locates at the docking position within the drive unit housing. In embodiments, the cap lock feature is in the first position during insertion of the cassette unit into the drive unit and moves to the second position when the cassette unit is in the docking position in the drive unit.

In embodiments, the drive unit includes a cap lock release feature arranged such that on moving of the cassette unit towards the docking position in the drive unit said cap lock release feature interacts with the cap lock feature of the cassette unit to move the cap lock feature to the second cap unlocking position when the cassette unit is at the docking position in the drive unit.

In embodiments, the cap lock feature (e.g. configured as a shuttle lock) includes one or more locking features, which in the cap locking position act such as to prevent movement (e.g. inwards movement) of one or more of the first engagement features of the removable cap and/or the second engagement features of the cassette unit housing.

In embodiments, in the first cap locking position the one or more locking features locate inwards or outwards of one or more of the first engagement features of the removable cap and/or of the second engagement features of the cassette unit housing such as to block disengaging movement (e.g. flexing movement) thereof. Thus, in embodiments, the removable cap and needle cover attached thereto are locked into the cassette unit when the cap lock (e.g. shuttle lock) is in such a cap locking position because the one or more first engagement features of the cap and/or the one or more second engagement features of the cassette unit housing are blocked from disengaging (e.g. by flexing movement) from their mutually engaging relationship.

In embodiments, the cap lock (e.g. shuttle lock) biases and is biased to a cap locking position. In embodiments, the cap lock (e.g. shuttle lock) is spring loaded so that the cap locking feature biases towards its first cap locking position. In embodiments, when the cap lock (e.g. shuttle lock) is moved forwards in the cassette unit housing, the first engagement features of the cap and/or second engagement features of the cassette unit housing are free to disengage (e.g. by suitable flexing movement) from their mutually engaging relationship. Once the cap lock (e.g. shuttle lock) is in this disengaged position, the removable cap and hence also the needle cover can be removed from the cassette unit.

In embodiments, the cap lock feature is arranged such that for replacement of the removable cap onto the cassette unit (e.g. after injection use of the syringe) the cap lock feature must be in the second, non-locking position.

Thus, in embodiments, the cap lock feature is arranged such that to replace the needle cover attached to the removable cap back onto the syringe, the cap lock feature must be in the second, non-locking position.

In embodiments, such as where the syringe is movable within the cassette unit, the cassette unit housing is provided with one or more (e.g. resiliently) flexible elements that extend (e.g. protrude) into the cassette unit housing cavity. In embodiments, the one or more (e.g. resiliently) flexible elements are provided as one or more separate parts that attach or fix to an inner wall of the housing or are otherwise in embodiments, held within the housing. In other embodiments, the one or more (e.g. resiliently) flexible elements are provided integrally with the housing (e.g. formed as an integral moulding therewith). The one or more flexible elements are typically provided to the needle receiving part of the cassette unit housing. The one or more (e.g. resiliently) flexible elements are desirably arranged to perform two separate functions.

Generally, in the rest configuration the needle sheath locates to seal off the needle tip, the one or more (e.g. resiliently) flexible elements contact the needle cover to restrict (e.g. prevent) movement thereof. Thus, movement of the needle cover is restricted by the action of the (e.g. resiliently) flexible elements, which in embodiments engage with the needle cover to hold it, and thereby restrict movement thereof. Such restriction of movement assists in maintaining the integrity of the seal relationship between the needle tip and the needle sheath.

In the use configuration, the needle cover is generally removed from the needle tip such as to unseal that tip. In this use configuration, the one or more (e.g. resiliently) flexible elements flex into the cassette unit housing cavity to provide a barrier surface. This barrier surface acts such as to obstruct the exit of the syringe barrel from the cassette unit housing cavity. Such obstructing function is particularly important in the instance of fracture (i.e. breakage) of the syringe, which is generally comprised of glass material. In this instance, the barrier surface acts such as to obstruct the exit of fractured parts (e.g. glass shards) of the syringe from the housing cavity. The patient is thereby, protected from coming into contact with such fractured parts, and thus potential injury in the event of such a syringe fracture event occurring.

In embodiments, the one or more (e.g. resiliently) flexible elements comprise a ring comprised of a (e.g. resiliently) flexible material such as a plastic polymer (e.g. an elastomer) or natural or synthetic rubber material. That ring (e.g. an O-ring) is generally provided to an inner wall of the (cylindrical) cassette unit housing such that the outer ring circumference thereof attaches to the inner wall of the cassette unit housing. In the rest configuration, the inner ring circumference thereof contacts the needle cover (e.g. the needle sheath or a needle sheath cover provided thereto) and is somewhat compressed inwards as a result of that contact, the effect of which is to restrict movement of the needle cover. In the use configuration, the needle cover is removed, and in the absence of compressive contact with the needle cover, the ring expands outwards into the cassette unit housing cavity to provide a barrier surface, which acts such as to obstruct the exit of the syringe barrel from the cassette unit housing cavity. In embodiments, the diameter of the uncompressed inner ring circumference of the ring is less than that of the syringe barrel such that when the ring is in its uncompressed state the syringe barrel may not pass through the ring.

In embodiments, each of the one or more (e.g. resiliently) flexible elements comprises a flexible finger element comprised of a (e.g. resiliently) flexible material such as a plastic polymer. Each finger element is generally provided to an inner wall of the (cylindrical) cassette unit housing such that the finger base thereof attaches to the inner wall of the cassette unit housing. Typically, an arrangement (e.g. circular arrangement) of flexible finger elements is employed such as from three to eight finger elements. In the rest configuration, the finger tip of each finger element contacts the needle cover (e.g. the needle sheath or a needle sheath cover provided thereto) and is somewhat flexed inwards as a result of that contact, the effect of which is to restrict movement of the needle cover. In the use configuration, the needle cover is removed, and in the absence of the compressive contact with the needle cover, the flexible finger element(s) flex into the cassette unit housing cavity to provide a barrier surface, which acts such as to obstruct the exit of the syringe barrel from the cassette unit housing cavity. Where the flexible finger elements are provided as a circular arrangement, it is preferable that the diameter of the inner circumferential aperture defined by the extremes of the finger tips thereof is less than that of the syringe barrel such that when the finger elements of that circular arrangement flex outwards the syringe barrel may not pass through the inner circumferential aperture defined thereby.

Drive Unit

The auto-injector herein is arranged to allow for actuation (i.e. firing) of the syringe and hence, to allow for injected delivery of drug to a patient. The auto-injector thus, also includes a drive unit for transferring axial drive to the syringe.

The drive unit comprises a drive unit housing defining a docking cavity and a needle delivery aperture. The docking cavity is arranged for docking receipt of the cassette unit at a docking position, whereupon said cassette unit and/or the syringe is movable from a rest position, in which the needle tip of the syringe is within the drive unit housing to a use position, in which the needle tip protrudes from said needle delivery aperture. The docking cavity and receivable part of the cassette unit are correspondingly sized and shaped to facilitate the intended docking relationship. The drive unit housing may be arranged as a single part or a multi-part (e.g. two part) drive unit housing assembly.

The drive arrangement comprises at least one electrically powered source of axial drive. The electrical power may be provided by mains electrical supply or by a battery, which in embodiments may be rechargeable.

Electrical energy may be conserved by a variety of means to enable the auto-injector to operate for longer on a given source of energy, such as a battery. Energy conservation or saving methods have additional advantages in terms of reducing the size requirements of the power source (e.g. battery) and thus the weight and portability of the auto-injector.

Electrical energy saving methods may be employed to reduce power consumption of the drive unit. One such method is to use a clock or timer circuit to switch the power on and off at regular or predetermined intervals. In another method a power management system is employed to selectively switch on/off specific electronic functions, such as visual display units or sensors, in order to power these functions only when they are required to perform a particular sequence of events. Thus different electronic functions may be switched on and off at varying intervals and for varying periods under control of a power management system.

In embodiments, the at least one electrically powered source of axial drive comprises an electrically powered motor. The motor may provide linear or rotary drive, but in general, rotary motors used in combination with suitable gearing arrangements are most suitable. The motor may for example, comprise a DC electric motor, a piezoelectric (PZ) motor, an ultrasonic motor, a solenoid motor or a linear motor. In embodiments, the electronic drive system comprises a DC motor, a PZ motor, a stepper motor or an ultrasonic motor. Embodiments are envisaged in which, plural electrically powered sources of axial drive are employed such as a different drive source (e.g. motor) for each of the first and second drive transfer elements.

The drive arrangement comprises a first drive transfer element for transferring axial drive to the cassette unit and/or the syringe for advancing the syringe to said use position; and a second drive transfer element for subsequently transferring axial drive to the plunger of the syringe for moving the plunger into the barrel of the syringe to eject at least part of the volume of liquid drug formulation.

In embodiments, the first and second drive transfer elements are configured as separate parts. In other embodiments, the first and second drive transfer elements are in coupling relationship (e.g. via one or more coupling elements) or form an integral part of a single (i.e. composite) drive transfer element.

In embodiments, the source of axial drive is configured to selectively confer axial drive to the first and second drive transfer elements. Any manner of gearing and/or coupling arrangements may be employed to achieve this purpose.

In embodiments, the drive arrangement comprises one or more lead screw drive mechanism. In other embodiments, the drive arrangement comprises one or more rack and pinion drive mechanisms. In embodiments, any of such drive mechanisms directly comprise the first and/or second drive transfer elements. In other embodiments, any of such drive mechanisms may be arranged to communicate with the first and/or second drive transfer elements by suitable gearing or coupling arrangements.

In embodiments, the electrically powered source of drive is able to exert an axial drive force of up to 60N via the first and/or second drive transfer elements to the syringe. In embodiments, the force exerted may be arranged to vary over the actuation profile such as from a range of 60 to 40N at the start of actuation to from 40 to 20N at the end of the actuation profile.

In embodiments, release of axial drive force (e.g. actuation of the electrically powered source of drive) is responsive to a trigger (e.g. a user-actuable trigger). In embodiments, the trigger comprises a button, switch or lever arrangement. In other embodiments, a press actuation mechanism that is actuable in response to pressing of the drive unit housing against the skin of a patient is also envisaged. In other embodiments, a skin sensor mechanism is provided to the drive unit housing that is actuable in response to sensing of the skin of the patient.

Axial drive force applied to the first drive transfer element results in drivable movement of the syringe from the rest to the use position. In embodiments, the first drive transfer element communicates directly with (e.g. contacts or abuts) the syringe barrel for transferring drive thereto. In embodiments, the first drive transfer element communicates directly with (e.g. contacts or abuts) the cassette unit for transferring drive thereto, and thus results in drive being transferred to the syringe barrel. In embodiments, the first drive transfer element communicates indirectly with (e.g. via a slaving or coupling element) the syringe barrel and/or the cassette unit for transferring drive thereto.

In embodiments, the first drive transfer element communicates directly or indirectly with a cassette unit holder that holds the cassette unit and syringe thereof within the drive unit such as to transfer drive to the cassette unit holder to thereby result in drivable movement of the syringe from the rest to the use position.

Axial drive force applied to the second drive transfer element (e.g. plunger rod) results in drivable movement of the plunger within the syringe barrel, ultimately to a fully plunged position when most, in embodiments all, of the liquid drug formulation contents of the syringe barrel have been drivably expelled therefrom.

In embodiments, the second drive transfer element communicates directly with (e.g. contacts or abuts) the plunger of the syringe for transferring drive thereto. In embodiments, an end portion of the second drive transfer element directly communicates with (e.g. contacts or abuts) the plunger. In other embodiments, the second drive transfer element communicates indirectly with (e.g. via a slaving or coupling element) the plunger of the syringe for transferring drive thereto. In certain other embodiments, an end portion of the second drive transfer element indirectly communicates with the plunger such as via a washer or other intermediate element.

In embodiments, the first and/or second drive transfer element takes the form of a screw drive element or rod drive element, but other suitable forms are also envisaged.

In embodiments, the drive arrangement includes a first coupling for coupling the first drive transfer element to the cassette unit and/or to syringe barrel of the syringe, wherein said first coupling is a reversible coupling arranged for decoupling when the syringe moves to the use position. Thus, in the initial rest position, application of axial drive force to the first drive transfer element results in movement of the syringe as a whole, but in embodiments, not of the plunger relative to the syringe barrel. It may be appreciated that this preferred initial absence of relative plunger movement is favoured if the frictional forces to be overcome in moving the syringe barrel within the housing are arranged to be much less than for moving the plunger within the syringe barrel. This is typically so since the plunger is often a natural or synthetic rubber element, which frictionally interacts with the sidewall of the syringe barrel. In embodiments, the first coupling is a friction clutch coupling arranged for decoupling by declutching thereof when the syringe moves to the use position.

In embodiments, once the syringe is in the use position (i.e. needle protruding) the first coupling decouples (e.g. demounts) such that no coupling then exists between the first drive transfer element and the syringe barrel. All further axial drive force applied to the second drive transfer element therefore results in plunging axial movement of the plunger within the syringe barrel, which acts to drive the liquid drug formulation contents of the syringe barrel into the hollow needle for injected delivery from the needle tip.

In embodiments, the first and second drive transfer elements are comprised as a single drive shuttle element. In embodiments, the shuttle has an axially symmetric form such as cylindrical form. Guides (e.g. a central aperture of an end wall) may be provided to the shuttle to assist that axial receipt.

In embodiments, a reset mechanism is provided for resetting the drive arrangement after actuation thereof. In embodiments, the reset mechanism is responsive to the electrically powered source of drive.

It is noted that fundamentally any electrically powered source of drive herein must convert electrical energy (e.g. stored in batteries) into mechanical motion for movement of the syringe and/or cassette unit and/or the plunger. Electric motors typically use electrical energy to produce rotational motion in the form of a rotating shaft. Various methods are well known for conversion of rotational energy into linear displacement of the plunger. Conceivable methods are a lead screw and worm gear arrangement, cams, a rack and pinion system or a system of rigid linkages using the lever principle. The various methods have certain advantages and disadvantages in terms of complexity, efficiency, mechanical advantage, gearing, maximum displacement velocity, maximum force etc.

Applicant has appreciated that generally for an injection, it is desirable to maintain a constant force over the full displacement stroke of the plunger. The performance in terms of maximum velocity and maximum force of cam and lever based mechanisms will typically vary with position along the injection stroke such that at extremes of the displacement range the maximum force or velocity of the plunger may be substantially different from that in the centre of the displacement range. The lead screw and worm gear or rack and pinion systems have the advantage that they can maintain constant forces over their full displacement range. The velocity of the plunger displacement determines the injection time, which is a key parameter in determining patient comfort. Finally, the maximum force that the electrically powered source of drive of the drive unit can produce will determine the limits of drug viscosity and/or needle bore that the device can use in injections. In general, the maximum plunger velocity and maximum force will be inversely related. That is, higher injection force will limit the velocity achievable.

In one aspect, an auto-injector drive unit includes a drive unit housing arranged for docking receipt of an injection cassette unit, a drive arrangement for ejecting at least part of a liquid drug formulation from the cassette unit, and a timer that starts a time count on removal of a removable needle cap from the cassette unit.

In embodiments, the timer is arranged such that on reaching a certain, predetermined time count a stop command to stop drive functioning of the drive unit is generated. The stop command may disable one or more electrically powered sources of drive. The stop command may initiate a blocking function that acts to block movement of drive transfer elements.

In embodiments, one or more cap removal sensors are provided to detect removal of the needle cap from the cassette unit. The cap removal sensors communicate with the timer to send a cap removal detection signal to the timer to initiate the time count thereof.

In embodiments, the drive unit includes an electronic display and the time count is displayed on the electronic display. The timer is arranged such that on reaching a certain, pre-determined time count an alarm command to initiate an audible alarm of the drive unit is generated.

In one aspect, an auto-injector drive unit includes housing means for receiving an injection cassette unit, drive means for ejecting at least part of a liquid drug formulation from the cassette unit, and timing means for starting a time count on removal of a cap means from the cassette unit.

Interaction of Cassette Unit with Drive Unit

The syringe is movable within the drive unit housing from a rest position, in which the needle tip of the syringe is within the drive unit housing to a use position, in which the needle tip protrudes from the needle delivery aperture of the drive unit housing.

In embodiments, the syringe is in fixed relationship to the cassette unit housing and the required movement of the syringe is by movement of the cassette unit housing and syringe fixed thereto within the drive unit housing.

In other embodiments, the syringe is in movable relationship to the cassette unit housing and the required movement of the syringe is by movement of the syringe within the cassette unit housing.

In other embodiments, composite arrangements are envisaged, in which the syringe movement is achieved by a combination of both movement of the syringe within the cassette unit housing and by movement of the cassette unit housing within the drive unit housing.

In embodiments, the drive unit housing and/or any inner drive unit housing sub assembly thereof includes a needle projection aperture through which the hollow needle may protrude, for example during expelling of the liquid drug formulation through the hollow needle and its needle tip for delivery to the patient.

In embodiments, it is desirable for safety and hygiene reasons that the needle does not protrude from (i.e. out with) the drive unit housing other than when expelling the liquid drug formulation during an injection procedure. Thus, the drive unit housing and/or any inner drive unit housing sub assembly thereof and drive unit housing cavity defined thereby is generally arranged such that a needle receiving part thereof allows for the needle of the syringe to be axially moveable therein from the rest position in which the needle is wholly housed (or shrouded) by the needle receiving part to the use position in which at least the tip of the needle protrudes from that needle receiving part of the drive unit housing.

In embodiments, the drive unit housing includes biasing means (e.g. a spring) arranged to act on the syringe and/or the cassette unit housing such that the needle of the syringe is normally biased towards the rest position, wherein such biasing means are overcome during the actuation of the syringe (e.g. by an actuating mechanism) to allow for movement of the needle to the use position.

In embodiments, it is desirable for drive unit housing to allow for the needle of the syringe to be retracted into the housing after use. Thus, it is desirable to be able to retract the needle back into the needle receiving part of the housing after the injection procedure, that is to say to retract the needle from the use position to a refracted position that may in embodiments, correspond to the rest position or in other embodiments, correspond to a third position, which in embodiments is further away from the needle delivery aperture. A needle retract mechanism may thus, be provided (e.g. responsive to a biasing means such as a light return spring or by reverse action of the drive mechanism) to retract the syringe needle back into the drive unit housing.

In embodiments, it is desirable for the drive unit housing to allow for the needle of the syringe to be shrouded by a needle shroud element after use. Thus, in particular it is desirable to be able to provide a means of shrouding the needle of the syringe that is moved or otherwise brought into operation after completion the injection procedure. Such means in embodiments comprises a movable shroud element that is adapted to be movable to a shrouding configuration at the end of the injection procedure.

In embodiments, the drive unit includes a cassette unit holder for holding the cassette unit within the drive unit housing. In embodiments, the cassette unit holder defines one or more inner walls against at least a part of which the cassette unit seats when held within the cassette unit holder.

In embodiments, the cassette unit holder is sized and shaped such as to allow for a relatively tight clearance between the cassette unit and the inner walls of the cassette unit holder. Such tight tolerances allow for reliable positioning of the cassette unit within the cassette unit holder and drive unit.

In embodiments, the cassette unit holder is mounted within the drive unit for movement along the drive axis, which corresponds to the injection axis, thereby allowing for movement of the cassette unit and syringe within the drive unit between its rest and in use (i.e. injected) positions. In embodiments, the cassette unit holder mounts to a linear slide that orients along a direction that is parallel with or corresponds to the drive axis.

In embodiments, the cassette unit holder is provided with one or more cassette unit locking features for reversibly locking the cassette unit within the holder and hence, within the drive unit.

In embodiments, the one or more cassette unit locking features are arranged to be in a locking position when the cassette unit is in the docking position and in a non-locking position otherwise, including when the cassette unit is at the intermediate pre-docking position.

In embodiments, movement of the cassette unit from the intermediate pre-docking position to the docking position results in movement of the one or more locking features from the non-locking to the locking position.

In embodiments, each cassette unit locking feature comprises a latching feature, lock tab feature or snap-lock feature. In embodiments, engagement of the locking feature provides tactile or audible feedback to the user as an indication that the cassette unit has been correctly received within the cassette unit holder of the drive unit.

In embodiments, the cassette unit holder is provided with one or more cassette unit locking features protruding from the inner wall(s) thereof. In embodiments, the cassette unit locking features are biased towards (e.g. in response to biasing means) or naturally bias towards the cassette locking position.

In embodiments, the cassette unit holder has plural (e.g. two) cassette unit locking features (e.g. snap lock-tabs) integral with and protruding inwards from the walls thereof.

In embodiments, each of the cassette unit locking features has one or more angled faces arranged such that the locking feature may be pushed outwards as a result of force applied to the angled face.

In embodiments, each cassette unit locking feature (e.g. lock tab) has angled faces at the top and bottom thereof arranged such that the locking feature (e.g. lock tab) flexes outwards when a force (e.g. from an edge of another mechanical part) is pushed into them from either direction.

In embodiments, the angled face at the bottom side of the locking feature allow for it to flex out of the way as the cassette unit is inserted into the cassette unit holder until the cassette unit is inserted to a holding and locking position, wherein the locking feature flexes back to its original position and lockingly engages the cassette unit housing. In this position the cassette unit is held in the cassette unit holder by the locking features (e.g. lock-tabs) because the top faces of the locking features (e.g. lock-tabs) support the cassette unit. The angled faces on the top of the locking features (e.g. lock-tabs) also allow for the cassette unit to be pulled out of the cassette unit holder by having the lock-tabs flex outwards in a similar fashion as when a cassette unit is inserted into the cassette unit holder of the drive unit of the auto-injector.

In embodiments, once the cassette unit has been inserted initially into the cassette unit holder, a reader of the drive unit reads an identifier on the cassette unit to verify details relating to it. Once positive verification has been established, the cassette unit is transported to the docking position such as by drawing it into the drive unit. In embodiments, this receipt of the cassette into the cassette unit holder corresponds to the pre-docking intermediate position referred to hereinafter.

In embodiments, as the cassette is transported to the docking position within the drive unit, the one or more locking features of the cassette unit holder are aligned with rigid features within the drive unit that maintain the locking features in the locking position such as by preventing lock-tabs from flexing outwards. Thus, the cassette unit is effectively locked within the drive unit when the locking features are aligned with these rigid features of the drive unit.

In embodiments, the length of the rigid features of the drive unit are arranged such that the cassette unit cannot be locked in the drive unit with the needle protruding from the needle delivery aperture such as at any insertion depth of the needle. Typically during the injection process, high loads are transmitted from the plunger through the cassette unit and reacted on the top surfaces of the locking features (e.g. lock-tabs). In embodiments where the top surface is angled, there is a horizontal component to the reaction load that attempts to flex the locking features (e.g. lock-tabs) outwards. However, where the locking features (e.g. lock-tabs) are aligned with (e.g. behind) the rigid features of the drive unit they cannot be flexed outwards and the cassette unit remains rigidly fixed in the drive unit.

In embodiments, once the cassette unit has been received at the docking position the removable cap and needle cover attached thereto is removed. Where in embodiments, there is a cap lock feature this must first be released. In embodiments, as the cassette is moved to the docking position (e.g. by being drawn fully up into the drive unit) the cassette unit is also brought into contact with cap lock unlocking features, which in embodiments comprise one or more (e.g. two) rigid arms, which extend into the cassette unit to depress, and thereby to unlock, the cap lock feature. In embodiments, the cap lock unlocking features are not rigidly fixed within the drive unit, and the rigid arms thereof that move into the cassette unit to depress, and thereby to unlock, the cap lock feature pass through cut-outs in the top of the cassette unit holder.

In embodiments, the drive unit is provided with a timer (e.g. timer function) that starts a time count on removal of the removable cap and needle cover from the cassette unit. In embodiments, the timer function is initiated by the removal of the removable cap and needle cover from the cassette unit. In embodiments, the timer counts upwards (i.e. from zero) on removal of the removable cap and needle cover). In other embodiments, the timer counts downwards (i.e. from a pre-determined time count) on removal of the removable cap and needle cover. Thus, for example an indication of time remaining to safely use the device may be calculated.

In embodiments, the timer is arranged such that on reaching a certain, pre-determined time count a stop command to stop the drive functioning of the drive unit is generated. Drive action of the drive unit is thus, prevented. In embodiments, the stop command is to disable (e.g. switch off or de-power) said one or more electrically powered sources of axial drive. In embodiments, the stop command is to initiate a blocking function that acts to block the movement of said first and/or second drive transfer elements. In embodiments, the timer therefore acts to ensure that drug is delivered to the patient within a set time limit following removal of the removable cap and needle cover from the syringe of the cassette unit.

In embodiments, one or more cap removal sensors (e.g. cap removal sensing means) are provided to detect removal of the removable cap and needle cover from the cassette unit. In embodiments, the one or more cap removal sensors communicate with the timer (e.g. via an electronic data unit or control unit) to send a cap removal detection signal to the timer to initiate the time count thereof.

In embodiments, the drive unit includes an electronic display and the time count is displayed on the electronic display.

In embodiments, to move the cassette unit within the drive unit, a first drive transfer element (e.g. a lead-screw) connects to (e.g. by threading through) a flange connecting to the cassette unit holder.

In embodiments, the cassette unit holder mounts to a linear slide such that it is slidably movable in a direction parallel to or corresponding to the drive axis. In embodiments, the first drive transfer element (e.g. lead-screw) couples to the output shaft of a motor/gear-head assembly such as via a universal joint. The universal joint allows for misalignment between the drive axis and the linear slide, which allows that the cassette unit holder and motor can be held rigidly in the drive unit without over-constraining the positioning of the cassette unit holder. Over-constraining the cassette unit holder could cause excessive friction or binding in the threads of the lead-screw and nut and so make high accelerations and velocities of the cassette unit holder difficult to achieve.

In embodiments, the lead-screw has four starts and a lead of 6.35 mm. Such a high lead allows for rapid linear accelerations of the cassette unit holder so that the needle can reach a velocity of 100 mm/sec before it pierces the patient's skin. In embodiments, this mechanism is arranged such as to be back-drivable.

In embodiments, the nut attached to the cassette unit holder has a specific linear travel for a given rotation of the screw. In consequence, the depth the needle is inserted into the patient is set by the rotational position of the screw. The position of the screw can be determined using several means including encoders and monitoring step-counts, in cases in which the motor being used is a stepper motor.

In embodiments, the drive unit can be configured to provide any suitable needle insertion depth with a typical needle insertion depth being between about 4 and 8 mm. Once the needle has been inserted into the patient, the injection of drug may be initiated. To inject the drug, axial drive force is applied to the second drive transfer element (e.g. plunger rod) to drivably move the plunger within the syringe barrel.

In embodiments, to apply the necessary driving load to the syringe plunger a second drive transfer element in the form of lead screw (e.g. a plunger screw) is rotated through a nut that is fixed relative to the syringe. Since the nut is fixed, the lead screw advances linearly as it is rotated. Having the nut fixed relative to the syringe allows for the plunger screw to stay fixed relative to the syringe when the cassette unit holder is moved within the device for needle insertion or retraction in an emergency. Otherwise, in embodiments, the plunger screw would be required to travel the distance that the cassette unit holder moves during needle insertion prior to its being able to make contact with the syringe to apply drive load to the syringe plunger. In embodiments, in the case of emergency retraction when the cassette unit holder needs to be moved into the drive unit in the middle of an injection, the plunger screw would have to be moved into the drive unit before the cassette unit could be rapidly retracted into the drive unit.

In embodiments, during an injection, loads reaching near 60N are applied to the syringe plunger via the second drive transfer element (e.g. the plunger screw).

In embodiments, the second drive transfer element (e.g. the rotating plunger screw) could direct undesirably high (e.g. torsion) drive loads on the system if the second drive transfer element makes direct contact with the syringe plunger. To minimize these torsion loads, the syringe barrel of the cassette unit may be provided with a plunger slaving part. Thus, the second drive transfer element acts to transfer axial drive to the plunger slaving part and hence, to the plunger of the syringe for moving the plunger into the barrel of the syringe to eject at least part of said volume of liquid drug formulation.

In embodiments, the plunger slaving part is in contact with the plunger of the syringe and is axially movable within the barrel. In embodiments, the plunger slaving part is arranged such that when a drive load is applied to a rear (e.g. top) drive-receiving face thereof the drive load is evenly transmitted to the plunger. In embodiments, the plunger slaving part engages (e.g. is in threaded engagement) with the plunger. In embodiments, the diameter of the plunger slaving part corresponds to the diameter of the plunger.

In embodiments, the plunger is made of a material that is resiliently compressible (e.g. rubber or an organic polymeric material) and the plunger slaving part is made of a less compressible material. In embodiments, the plunger slaving part is made of a rigid material (e.g. a hard plastic polymer material such as poly propylene).

In embodiments, the rear face of the plunger slaving part has a central recess for receipt of a drive transfer element. In embodiments, the central recess is of conical form. Thus in embodiments, the second drive transfer element defines a drive end arranged for receipt by the central recess of the rear drive-receiving face of the plunger slaving part. In embodiments, the drive end defines a conical tip and said central recess is of conical form to guide and centre said conical tip therein. In embodiments, the angle of the conical recess is greater than the angle of the conical tip.

In embodiments, the slaving part may be configured to perform a second purpose of providing an easy-to-identify visual indicator of the plunger's position within the syringe so that the patient can visually confirm the drug had been fully injected. In this embodiment, the slaving part may be called a stopper position indicator.

In the above described plunger screw embodiment, the plunger screw is rotated through a fixed nut. In consequence, the combination of the high linear force with the rotating plunger screw could result in high torsion loads on the system if the plunger screw makes direct contact with the syringe plunger. To minimize these torsion loads, the plunger screw is in embodiments, provided with a pointed tip to give rise to a point load instead of a face load. The pointed tip of the plunger screw makes contact with a slaving part, which is made of a hard material, thus acting to reduce friction and torsion loads on the system. The slaving part contacts (e.g. engages) the plunger such that when a load is applied to its top face the load is evenly transmitted directly into the plunger. In embodiments, the top of the slaving part has a conical recess to guide and centre the pointed end of the plunger screw as it is lowered into contact. In embodiments, the angle of the conical recess is greater than the angle of the conical end of the plunger screw to achieve point contact between the tip of the plunger screw and the top surface, while also guiding the syringe plunger during its travel.

In embodiments, the plunger screw is rotated by a screw gear, which receives drive force from the source of axial drive. In embodiments, the plunger screw slide fits through the center of the gear and is keyed to gear via a flat. Since in this embodiment, the plunger screw has a flat, there are sharp corners where the flat is cut across the threads. In consequence, reliefs are provided in the walls of pass-through hole in the screw gear to eliminate the possibility of the thread corners from catching on the screw gear as the plunger screw slides through it. In embodiments, the screw gear is fixed within the device via a press-fit with a ball bearing that is fixed within the drive unit.

In embodiments, to control the position and angular velocity of the screw gear, and thus the position and velocity of the plunger screw, the screw gear is arranged to mesh with a gear mounting to the shaft of a motor/gearhead assembly. In embodiments, the rotation and angular velocity of the output of the motor/gearhead shaft directly correlates to the position and velocity of the plunger screw. Thus, the position of the plunger screw is determined by the rotational position of the screw. This position of the plunger screw is in embodiments, monitored using encoders anywhere in the drive train that has rotating components or by monitoring step-counts if using a stepper motor.

In embodiments, the drive unit is arranged to initially receive the cassette unit housing at an intermediate pre-docking position for subsequent transport of the cassette unit to the docking position.

In embodiments, the drive unit is arranged to initially receive the cassette unit housing at the intermediate pre-docking position for automated verification thereof. Such verification can for example, be for the purpose of checking of drug and dosage information, checking that the drug is not past its expiry date and/or checking that the cassette has not been used previously.

In embodiments, the cassette unit is receivable by a cassette unit holder of the drive unit and the position corresponding to (e.g. initial) receipt of the cassette into the cassette unit holder corresponds to the intermediate position at which the automatic verification step is carried out.

In embodiments, the cassette unit further comprises an identifier. The identifier comprises data in a form that may be readily subject to interrogation. The drive unit comprises a reader for reading (interrogating) the identifier of the cassette unit and, in communication with the reader, a verifier for verifying the identifier.

In embodiments, the drive unit is arranged such that transport of the cassette unit to the docking position is permitted only following positive verification of the identifier. Thus, only appropriately identified cassette units are finally receivable into the device to enable injected drug delivery there from.

In embodiments, the identifier may include labelling selected from the group consisting of visual text, machine-readable text, bar codes, and dot codes. In embodiments, the identifier is in the form of a passive transceiver (e.g. an RFID tag) that is interrogable by means of an active transceiver (e.g. an RFID reader). In embodiments, the identifier is in the form of a bar code that is interrogable by means of a bar code reader.

In embodiments, the cassette unit comprises a first transceiver for transmitting and receiving data and the drive unit comprises a second transceiver for transmitting and receiving data, wherein data is transferable at least from the first transceiver to the second transceiver, and in embodiments in two-way fashion from the first transceiver to the second transceiver. The data is in embodiments in digital form and suitable for transfer by electronic, radio or optical means.

An advantage of embodiments of this type is the ability to store many types of information in different parts of the memory structure of the transceivers. The information is furthermore stored in a form, which is readily and accurately transferable. The information could for example, include manufacturing and distribution compliance information written to the memory at various points in the manufacturing or distribution process, thereby providing a detailed and readily accessible product history of the cassette unit housing. Such product history information may, for example, be referred to in the event of a product recall. The compliance information could, for example, include date and time stamps. The information could also include a unique serial number stored in encrypted form or in a password protectable part of the memory, which uniquely identifies the drug product and therefore may assist in the detection and prevention of counterfeiting. The information could also include basic product information such as the nature of the drug and dosing information, customer information such as the name of the intended customer, and distribution information such as the intended product destination.

On loading the drive unit with the cassette unit housing the second transceiver may, for example, read the unique serial number, batch code and expiry date of the drug and any other information on the first transceiver. In this way the nature and concentration of the drug in the syringe of the cassette unit, may be determined. Other information, such as the date and time of administration of the drug, or environmental exposure data such as the minimum/maximum temperatures or levels of humidity the cassette unit has been exposed to, may also be read and displayed to the user. In embodiments, this information is displayed to the patient on a visual display unit.

Data may also be transferred to and from any transceiver during the period of use of the auto-injector by the patient. For example, the auto-injector may include an electronic data system having various sensors associated therewith. Any data collected by the sensors or from any data collection system associated with the electronic data system including a clock or other date/time recorder is transferable. Data may be transferred each time the patient uses the auto-injector. Or alternatively, data may be stored in a database memory of the electronic data system and periodically downloaded to any transceiver. In either case, a history of the usage of the auto-injector may be built up in the memory of any transceiver.

In embodiments, the first and second transceiver each comprise an antenna or equivalent for transmitting or receiving data and connecting thereto a memory. The memory will typically comprise an integrated circuit chip. Either transceiver may be configured to have a memory structure, which allows for large amounts of information to be stored thereon. The memory structure can be arranged such that parts of the memory are read-only, being programmed during/after manufacture, other parts are read/write and further parts are password protectable. Initial transfer of information (e.g. at the time of manufacture or of dispensing) to or from any transceiver can be arranged to be readily achievable by the use of a reader which is remote from the auto-injector, thereby minimising the need for direct product handling.

In embodiments, data is transferable (e.g. in two-way fashion) between the first transceiver on the cassette unit and second transceiver on the drive unit without the need for direct physical contact therebetween. In embodiments, data is transferable wirelessly between the first and second transceiver.

In embodiments, the second transceiver on the drive unit is an active transceiver and the first transceiver on the cassette unit is a passive transceiver. The term active is used to mean directly powered and the term passive is used to mean indirectly powered.

In embodiments, the first transceiver on the cassette unit comprises an identifier or tag comprising an antenna for transmitting or receiving interrogating energy; and an integrated circuit chip connecting with said antenna, and the second transceiver on the drive unit comprises a reader for said identifier or tag. In this case the identifier or tag is a passive transceiver and the reader is an active transceiver. In embodiments, the reader is not in direct contact with the tag or identifier that is to be read.

In embodiments, the integrated circuit chip has a read only memory area, a write only memory area, a read/write memory area or combinations thereof. In embodiments, the integrated circuit chip has a one-time programmable memory area. In embodiments, the one-time programmable memory area contains a unique serial number. In embodiments, the integrated circuit chip has a preset memory area containing a factory preset, non-changeable, unique data item. In embodiments, the preset memory item is in encrypted form. In embodiments, the integrated circuit chip has plural memory areas thereon. In embodiments, any memory area is password protected. In embodiments, any memory area contains data in encrypted form. Electronic methods of checking identity, error detection and data transfer may also be employed. In embodiments, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

In embodiments, the tag is on a carrier and the carrier is mountable on the cassette unit. In embodiments, the carrier comprises an insulating material such as a glass material or, a paper material or an organic polymeric material such as polypropylene.

The interrogating energy may be in any suitable form including ultrasonic, infrared, radiofrequency, magnetic, optical and laser form. Any suitable channels may be used to channel the energy including fibre optic channels.

In embodiments, the first transceiver on the cassette comprises a radiofrequency identifier (RFID) comprising an antenna for transmitting or receiving radiofrequency energy; and an integrated circuit chip connecting with said antenna, and the second transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or identifier to be read.

The radiofrequency identifier can be any known radiofrequency identifier. Such identifiers are sometimes known as radiofrequency transponders or radiofrequency identification (RFID) tags or identifiers. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

In embodiments, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In embodiments, the first transceiver on the cassette unit comprises a magnetic identifier or tag comprising an antenna for transmitting or receiving magnetic field energy; and an integrated circuit chip connecting with said antenna, and the second transceiver on the drive unit comprises a reader for said magnetic identifier or tag. In this case the magnetic identifier or tag is a passive transceiver and the reader is an active transceiver.

In embodiments, the first transceiver on the cassette unit comprises a microelectronic memory chip and the second transceiver on the drive unit comprises a reader for said microelectronic memory chip. The microelectronic memory chip may comprise an Electrically Erasable Programmable Read Only Memory (EEPROM) chip, a SIM card-type memory chip or a flash type memory chip. In this case the microelectronic memory chip is a passive transceiver and the reader is an active transceiver.

Once the reader has read (or interrogated) the identifier of the cassette unit, that identifier data is communicated to a verifier, which conducts a verification step.

In embodiments, the verifier carries out the verification by comparing one or more pieces of data read from the identifier with acceptable data values. In embodiments, the comparison makes reference to a look-up table of acceptable values, which may include data that is patient specific. In one embodiment, the acceptable values of look-up table are pre-loaded into an electronic data unit of the drive unit. In another embodiment, the acceptable values of look-up table are downloadable to an electronic data unit of the drive unit (e.g. by communicating with an online data source). In one embodiment, the acceptable values of look-up table are calculable by an electronic data unit of the drive unit (e.g. based on data input by the user or feed-ins from sensors of the device). In one example, the data relates to type of drug with a comparison being made between the type of drug contained within the syringe and that required by the patient. In another example, the data relates to the 'use by' date of the drug with verification being made by reference to an electronic calendar of the electronic data unit of the drive unit with positive verification being registered only if the 'use by' date of the drug has not been exceeded. In another example, the data relates to the 'lot number' of the cassette unit and a check is made against whether that 'lot number' has been subject to a recall or not.

In embodiments, the drive unit is arranged such that transport of the cassette unit from the intermediate position to the docking position is permitted only following positive verification of the identifier. Thus, only appropriately verified cassette units are finally receivable into the device for drug delivery there from.

In embodiments, that transport of the cassette unit to the docking position is by automatic control under the action of the electrically powered source of drive. Thus, in embodiments positive verification of the cassette unit gives rise to a 'transport to docking position' signal from the electronic data unit to the source of drive, which results in the required transporting action.

In embodiments, the drive unit comprises a compartment for storage of one or more cassette units.

Electronic Data System

In embodiments, the auto-injector additionally comprises an electronic data system, typically under the control of one or more microcomputers. In embodiments, the electronic data system has input/output capability and comprises a memory for storage of data; one or more microprocessors for performing operations on said data; and a transmitter for transmitting a signal relating to the data or the outcome of an operation on the data. In embodiments, the electronic data system is arranged to be responsive to or activated by the voice of a user. Thus, for example the electronic data system may be switched on or off in response to a voice command.

In embodiments, the electronic data system is integral with the drive unit. Alternatively, the electronic data system forms part of an electronic data unit such as on a circuit board or plug-in, which is reversibly associable with the drive unit.

In embodiments, the drive unit or separable electronic data unit additionally comprises a data input system for user input of data to the electronic data system. In embodiments, the data input system comprises a man machine interface (MMI) in embodiments selected from a keypad, voice recognition interface, graphical user interface (GUI) or biometrics interface.

In embodiments, the electronic data system additionally comprises a visual display unit for display of data to the user. The display may for example, comprise a screen such as an LED or LCD screen. In embodiments the visual display unit is associable with the drive unit.

In embodiments, the auto-injector additionally comprises a data link for linking to a local data store to enable communication of data between the local data store and the electronic data system. The data store may also comprise data management, data analysis and data communication capability.

The data store may itself form part of a portable device (e.g. a handheld device) or it may be sized and shaped to be accommodated within the patient's home. The data store may also comprise a physical storage area for storage of replacement cassette units. The data store may further comprise an electrical recharging system for recharging any electrical energy store of the drive unit, particularly a battery recharging system.

The data link may for example enable linking with a docking station, a personal computer, a network computer system or a set-top box by any suitable method including a hard-wired link, an infrared link or any other suitable wireless communications link.

In embodiments, the auto-injector additionally comprises a communicator for wireless communication with a network computer system to enable transfer of data between the network computer system and the electronic data system. In embodiments, the communicator enables two-way transfer of data between the network computer system and the electronic data system. Wi-Fi enabled communicators are envisaged.

In embodiments, the data is communicable between the network computer system and the electronic data system in encrypted form. All suitable methods of encryption or partial encryption are envisaged. Password protection may also be employed. In embodiments, the communicator employs radiofrequency or optical signals.

In embodiments, the communicator communicates via a gateway to the network computer system. In another aspect, the communicator includes a network server (e.g. a web server) such that it may directly communicate with the network.

In a further aspect, the communicator communicates with the gateway via a second communications device. In embodiments, the second communications device is a telecommunications device, more in embodiments a cellular phone or pager. In embodiments, the communicator communicates with the second communications device using spread spectrum radiofrequency signals. A suitable spread spectrum protocol is the Bluetooth (trade mark) standard, which employs rapid (e.g. 1600 times a second) hopping between plural frequencies (e.g. 79 different frequencies). The protocol may further employ multiple sending of data bits (e.g. sending in triplicate) to reduce interference.

In embodiments, the network computer system comprises a public access network computer system. The Internet is one suitable example of a public access network computer system, wherein the point of access thereto can be any suitable entry point including an entry point managed by an Internet service provider. The public access network computer system may also form part of a telecommunications system, which may itself be a traditional copper wire system, a cellular system or an optical network.

In another aspect, the network computer system comprises a private access network computer system. The private access network system may for example, comprise an Intranet or Extranet, which may for example, be maintained by a health service provider or drug manufacturer. The network may for example include password protection; a firewall; and suitable encryption means.

In embodiments, the communicator enables communication with a user-specific network address in the network computer system. The user-specific network address may be selected from the group consisting of a web-site address; an e-mail address and a file transfer protocol address. In embodiments, the user-specific network address is accessible to a remote information source such that information from said remote information source might be made available thereto.

In embodiments, information from the user-specific network address is made available to the remote information source. In embodiments, the remote information source is a source of drug prescriptions, for example a doctor's practice or a hospital; a pharmacy; an emergency assistance provider; a manufacturer of drugs; or a research establishment.

In embodiments, the auto-injector additionally comprises a geographic positioning system such as a global positioning system or a system, which relies on the use of multiple communications signals and a triangulation algorithm.

In embodiments, the auto-injector additionally comprises an orientation sensor for checking on the orientation thereof. In embodiments, the auto-injector is arranged to operate only when in certain defined orientations (e.g. upright or nearly so).

Kit of Parts

In embodiments, there is also provided a kit of parts comprising a cassette unit (absent syringe) as described above; and a syringe containing a liquid drug formulation.

In embodiments, there is further provided a kit of parts comprising a cassette unit (which may in embodiments, be in kit of parts form) as described above; and a drive unit as described above.

In embodiments, there is further provided a kit of parts comprising an auto-injector (which may in embodiments, be in kit of parts form) as described above; and packaging therefor. Suitable packaging typically comprises a storage container for the drive unit and one or more cassette units.

In certain implementations, an injection kit includes a cassette unit housing having an inner surface and a plurality of syringe barrels having different physical dimensions. The kit may also include a plurality of sleeve form adapters configured to receive at least one of the syringe barrels, where the sleeve form adapter has an outer surface configured to interfit with the inner surface of the cassette unit housing.

In certain embodiments, each syringe barrel has a unique circumference size or a unique contoured surface that mates with the sleeve form adapter.

Method of Assembling a Medicament-Injector

In certain implementations, a method of assembly a medicament-injector includes selecting a syringe barrel among a plurality of syringe barrels, each of the plurality of syringe barrels having a different physical dimension than is found in the other of the plurality. The method may also include selecting a sleeve form adapter configured to mate with the selected syringe barrel, interfitting the syringe barrel within the sleeve form adapter, and installing the sleeve form adapter within a cassette unit. In certain embodiments, each syringe barrel has a unique circumference size or a unique contoured surface that mates with the sleeve form adapter.

BRIEF DESCRIPTION OF THE DRAWINGS

The disclosure is further described with reference to the accompanying drawings, in which:

FIG. 13 is a part-exploded view of an alternative syringe with shoulder support assembly suitable for use with any of the cassette units of FIGS. 1 to 12;

FIG. 14 is a perspective view of the alternative syringe with shoulder support assembly of FIG. 13;

FIGS. 21a to 21c respectively show cross-sectional, side cross-sectional and plan views of the removable cap absent connector of the assembly of FIG. 16;

FIGS. 22a to 22f are various views of the connector for connecting the needle cover to the removable cap in the assembly of FIG. 16;

FIGS. 27a and 27b are sectional views showing details of the fifth cassette unit of FIG. 25 at respective, first (pre-use) and second (after-use and recapping) positions;

FIG. 29 is a perspective view of a first drive unit, particularly suitable for use with any of the third to fifth cassette units herein;

FIG. 30 is a perspective view of the first drive unit of FIG. 29 with a cassette unit received at the docking position;

DETAILED DESCRIPTION

To provide an overall understanding of the systems, devices and methods described herein, certain illustrative embodiments will now be described. For the purpose of clarity and illustration these systems and methods will be described with respect to auto-injectors that employ electrically powered drive units and cassette units that receive medicament syringes. It will be understood by one of ordinary skill in the art that the systems, devices and methods described herein may be adapted and modified as is appropriate, and that these systems, devices and methods may be employed in other suitable applications, such as for other types of drive units and cassette units, and that other such additions and modifications will not depart from the scope hereof.

Figure 1:
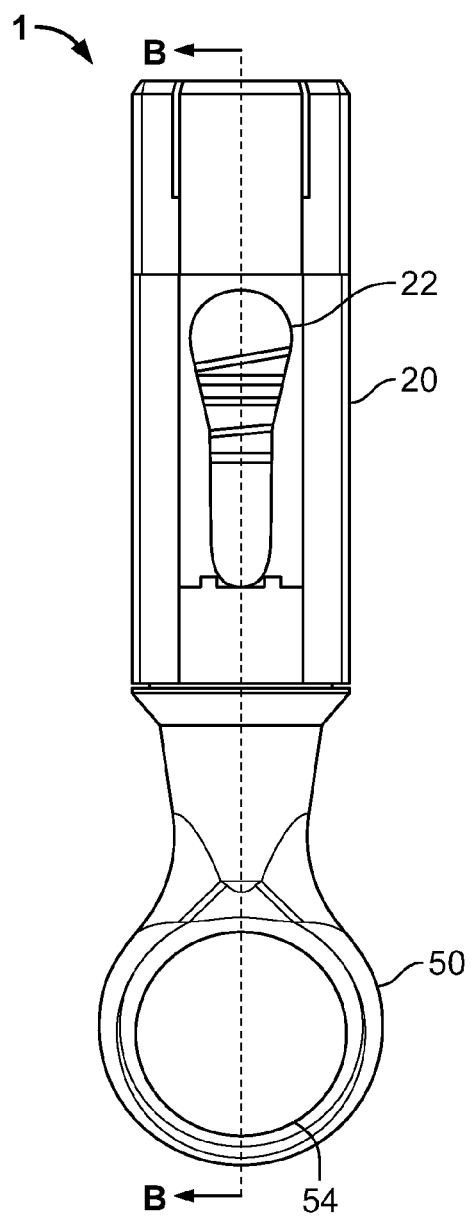
FIG. 1 is a perspective view of a first cassette unit of an auto-injector herein arranged for use with a 2.25 ml syringe and shown in the 'pre-use' configuration.
Figure 2A:
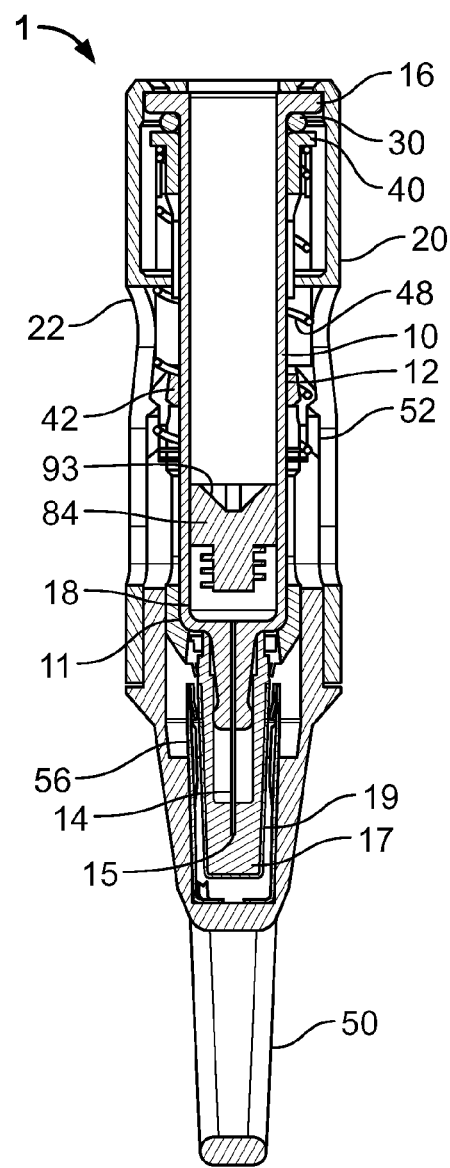
FIG. 2a is a sectional view taken along line B-B of the first cassette unit of FIG. 1 now shown in the 'post-use' configuration.
Figure 2B:
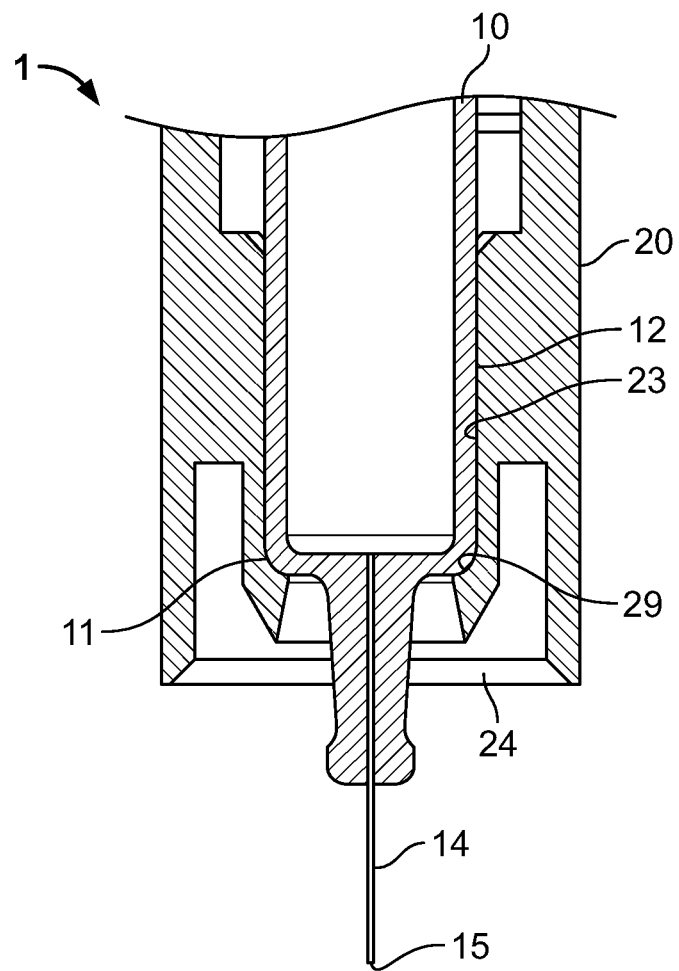
FIG. 2b is a sectional view taken along line B-B of the first cassette unit of FIG. 1 of a detail of the syringe shoulder part of that first cassette unit, as shown with the end cap removed and also absent syringe plunger.
Figure 3:
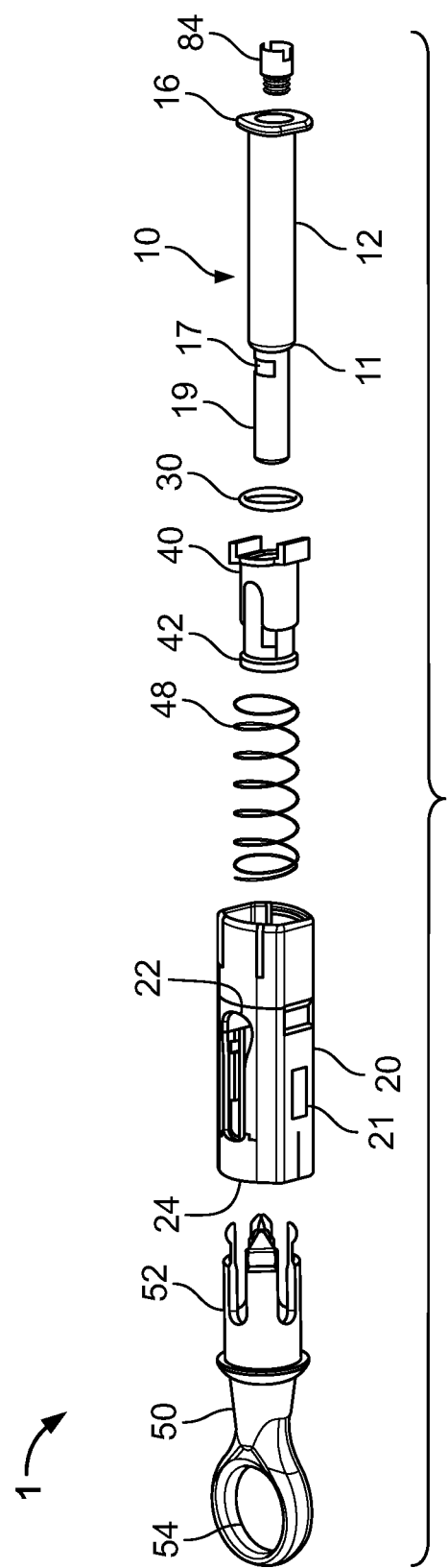
FIG. 3 is an exploded view of the first cassette unit of FIG. 1.
Figure 4:
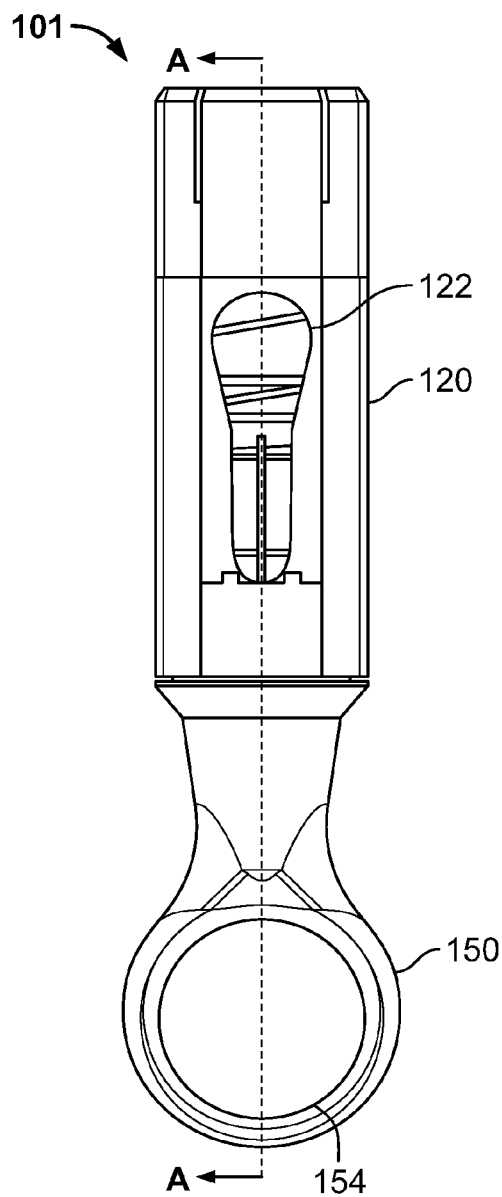
FIG. 4 is a perspective view of a second cassette unit of an auto-injector herein arranged for use with a 1 ml syringe and shown in the 'pre-use' configuration.
Figure 5A:
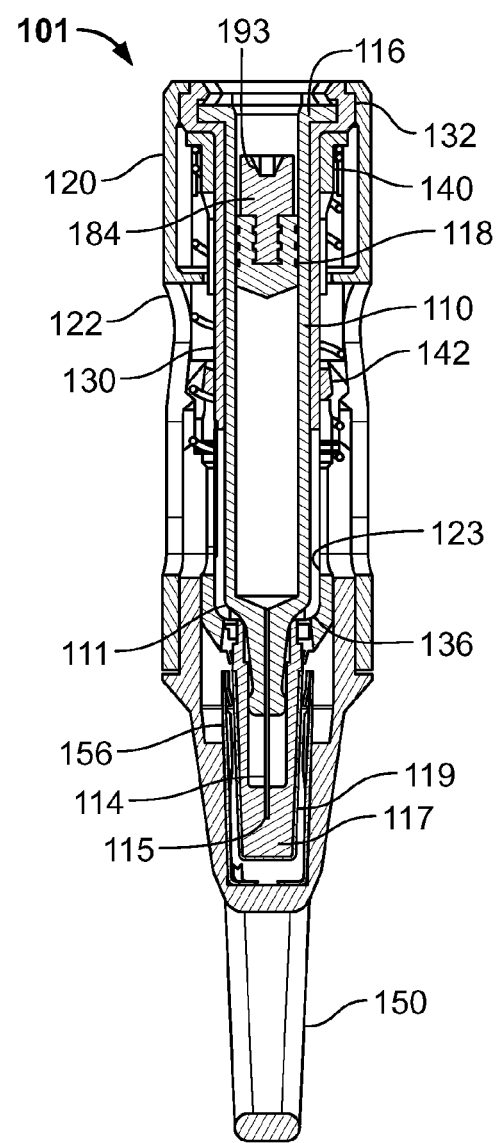
FIG. 5a is a sectional view taken along line A-A of the second cassette unit of FIG. 4 also in the 'pre-use' configuration.
Figure 5B:
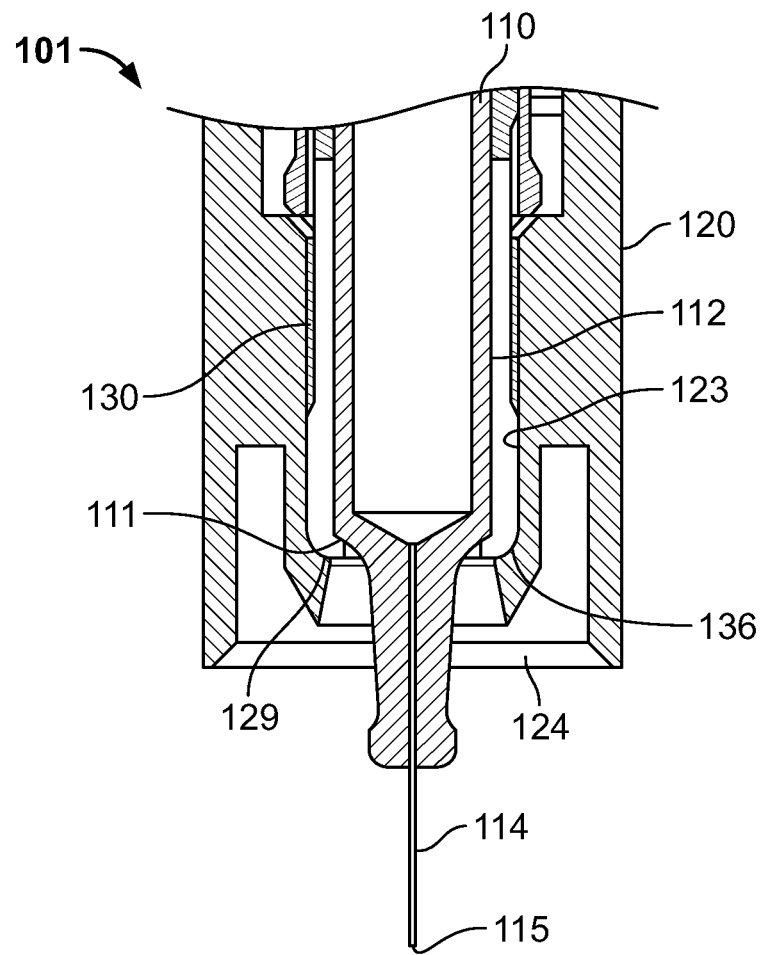
FIG. 5b is a sectional view taken along line A-A of the second cassette unit of FIG. 4 of a detail of the syringe shoulder part of that second cassette unit, as shown with the end cap removed.
Figure 6:
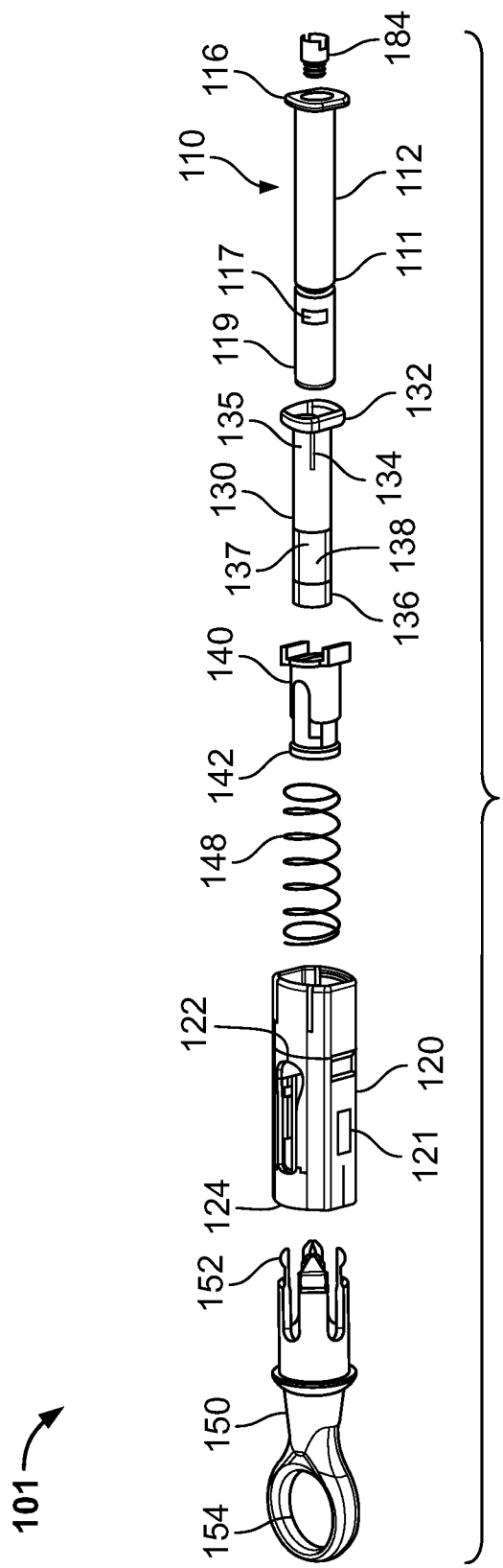
FIG. 6 is an exploded view of the second cassette unit of FIG. 4.

Referring now to the drawings, FIGS. 1 to 3 show a first cassette unit 1 of an auto-injector herein arranged for use with a 2.25 ml syringe. FIGS. 4 to 6 show a second cassette unit that may be appreciated to be a variant of the first cassette unit, but adapted to receive a smaller 1 ml syringe. The syringe size may be selected from a wide range of sizes.

The first cassette unit 1 of FIGS. 1 to 3 is arranged for use with a syringe 10 that contains a liquid drug formulation (not shown). The cassette unit 1 comprises an elongate form cassette unit housing 20 that is arranged for receipt of the syringe 10 and is sized and shaped for this purpose. The cassette unit housing 20 is provided with a viewing window 22 that allows for viewing of the contents of the syringe 10 to check for dispensing thereof. The cassette unit 1 is provided with a removable cap 50 that is arranged to engage the needle cover comprising needle sheath 17 and rigid needle sheath shell 19 of the syringe 10 and that is shown at FIGS. 1 and 2 in the capped position. Engagement of the needle cover 17, 19 by the removable cap 50 is by means of cage-like needle cover gripper 56, further details of which are described by reference to FIGS. 16 to 24 herein. The cap 50 is provided at the brim thereof with a crown arrangement of first engagement features 52 that are sized and shaped to extend up into the cassette unit housing 20 when the cap 50 is in the capping position. The cap is shaped to define a ring pull 54 for receipt by the finger of a user. The interactions of the cap 50 with the needle cover 17, 19 and with cap lock feature 40 are described in more detail hereinafter.

The syringe 10 is of a standard 2.25 ml type and comprises a barrel 12 with end flange 16 for holding a liquid drug formulation; a hollow needle 14 at one end of the barrel 12; and a syringe plunger 18 in the form of a rubber stopper that is arranged for axial movement within the barrel 12 such as to enable the liquid drug formulation to be expelled through the hollow needle 14. As shown at FIG. 2, the syringe plunger 18 is at the 'end of use' position. The hollow needle 14 defines a needle bore, which is of circular cross-section (e.g. 23G, 25G or 27G diameter) and a needle tip 15. The needle tip 15 is sheathed by needle sheath 17, which is provided with rigid needle sheath shell 19. The needle sheath 17 and rigid shell 19 in combination define a 'needle cover'.

The syringe plunger 18 is provided with a slaving part 84 that is received as an insert to the rear end of the plunger 18. The slaving part 84 is arranged to function such that when a load is applied to its top face the load is evenly transmitted directly into the plunger 18. The rear face of the plunger slaving part 84 has a central recess 93 of conical form for receipt of a drive transfer element. The slaving part 84 is brightly-coloured and performs a second function of providing an easy-to-identify visual indicator of the position of the plunger 18 within the syringe 10 so that the patient can visually confirm the drug had been fully injected. The cassette unit housing 20 of the cassette unit 1 is arranged to define a cassette unit housing cavity that is sized and shaped for generally fixed receipt of the syringe 10. The cassette unit housing 20 defines at its forward end a needle delivery aperture 24 through which in use, the hollow needle 14 of the syringe 10 protrudes on removal of the cap 50 and needle cover 17, 19 there from. Syringe 10 is provided with an adapter ring 30 that seats adjacent to the end flange 11 of the syringe barrel 12. The cassette unit housing 20 is also provided with a security label 21, which may in aspects be an RFID tag label for use in verification purposes.

The cassette unit 1 is provided with a cap lock feature 40 with lock ring 42 arranged for locking interaction with the first engagement features 52 of the removable cap 50 for selectively preventing removal of the cap 50 from the cassette unit housing 20 and also for preventing rotation of the cap 50 relative to the cassette unit housing 20. A detailed description of the action of this cap lock feature 40 is provided hereinafter. Cap lock spring 48 fits around the cap lock feature 40.

Applicant has found that to reduce the risk of the syringe 10 shattering under the loads associated with injecting the drug, it is important for a majority of the load path to travel through the forward shoulder 11 of the syringe barrel 12 and lesser load to pass through the flange 16 at the rear end thereof. As most clearly seen by reference to FIG. 2b, the forward shoulder 11 of the syringe 10 is thus, arranged to seat adjacent to an annular shoulder support rim 29 that is defined at the forward end of the inner wall 23 of the cassette unit housing 20. In addition, the barrel 12 of the syringe 10 interacts with the inner wall 23 of the cassette unit housing 20, which thereby acts to constrain the position of the syringe 10 within the cassette unit housing 20.

The cassette unit 1 herein may be arranged to accommodate multiple syringe sizes by providing different shapes and sizes of adapters to the barrel 12 of the syringe 10. FIGS. 4 to 6 show a second cassette unit 101 that is a variant of the first cassette unit 1, but now adapted to receive a smaller syringe 110 of 1 ml capacity.

Thus, second cassette unit 101 of FIGS. 4 to 6 is arranged for use with a 1 ml syringe 110 that is arranged to contain a liquid drug formulation (not shown). The cassette unit 101 comprises an elongate form cassette unit housing 120 with security label 121 and viewing window 122 that is arranged for receipt of the syringe 110 and is sized and shaped for this purpose. The cassette unit 101 is provided with a removable cap 150 defining a crown arrangement of first engagement features 152 and ring pull 154, which cap 150 is shown at FIGS. 4 and 5 in the capped position.

The syringe 110 is of a standard 'long' 1 ml type and comprises a barrel 112 with end flange 116 for holding a liquid drug formulation (not shown); a hollow needle 114 at one end of the barrel 112; and a syringe plunger 118 (not visible in FIG. 5b) in the form of a rubber stopper that is arranged for axial movement within the barrel 112 such as to enable the liquid drug formulation to be expelled through the hollow needle 114. As shown at FIG. 5a, the syringe plunger 118 is at the 'pre-use' position. The hollow needle 114 defines a needle bore, which is of circular cross-section (e.g. 23G, 25G or 27G diameter) and a needle tip 115. The needle tip 115 is sheathed by needle sheath 117, which is provided with rigid needle sheath shell 119 to in combination define a 'needle cover'. As in the first cassette unit, the needle cover 117, 119 is engaged by the removable cap 150 by means of cage-like needle cover gripper 156, further details of which are described by reference to FIGS. 16 to 24 herein. As before, the syringe plunger 118 is provided with a slaving part 184 that inserts into the leading end of the plunger 118. The rear face of the plunger slaving part 184 has a central recess 193 of conical form for receipt of a drive transfer element. The slaving part 184 is also arranged to function as a stopper position indicator.

The housing 120 of the cassette unit 101 is arranged to define a cassette unit housing cavity sized and shaped for generally fixed receipt of the syringe 110. The cassette unit housing 120 defines at its forward end a needle delivery aperture 124 through which in use, the hollow needle 114 of the syringe 110 protrudes on removal of the cap 150 there from.

Syringe 110 is provided with a sleeve form adapter 130 arranged for receipt by the outer wall of the syringe barrel 112. The rear end 132 of the sleeve form adapter 130 is both flared and provided with plural slits 134 in the wall thereof such as to define rearward flexible fingers 138, which allow the adapter 130 to snap-fit over the flange 116 of the syringe barrel 116. Thus, the flange 116 of the syringe 110 is effectively captured by the flange-receiving part 132 of the sleeve form adapter 130. In overall terms, the sleeve form adapter 130 acts to sleeve a major portion of the syringe barrel 112 and end flange 116 thereof. The effect of this sleeved relationship is firstly to increase the effective diameter of the syringe barrel 112; secondly to provide strengthening reinforcement to the end flange 116 thereof; and thirdly to increase the effective length of the syringe 112.

The sleeve adapter 130 is also provided with plural slits 137 in the wall at the forward end 136 of the sleeve adapter 130 such as to define forward flexible fingers 138, which allow the forward end of the adapter 130 to flex open. The presence of such flexible fingers 138 is of utility during assembly of the sleeved syringe as the needle cover 117, 119 which typically has a larger diameter than the syringe barrel 112, passes through the centre of it when the syringe 110 is pressed into the sleeve adapter 130. The end flange 116 of the syringe 110 then snaps into the rear end 132 of the sleeve adapter 130 such that the syringe 110 is locked into the adapter 130 once assembled.

On a point of detail, adding such a sleeve adapter 130 to the 'long' (smaller diameter) 1 ml syringe 110 can make it slightly longer than the 2.25 ml syringe 10 of FIGS. 1 to 3. Thus, when the cassette unit 1 is assembled with the 2.25 ml syringe, adapter ring 30 is provided adjacent to the syringe flange 16 to make its effective flange thickness the same as that of the smaller 1 ml syringe 110 with a sleeve adapter 130.

Applicant has found that to reduce the risk of the syringe 110 shattering under the loads associated with injecting the drug, it is important for a majority of the load path to travel through the forward shoulder 111 of the syringe barrel 112 and lesser load to pass through the flange 116 at the rear end thereof. As most clearly seen by reference to FIG. 5b, the forward end 136 of sleeve adapter 130 fits around the forward shoulder 111 of the syringe 110 and thus, defines an annular shoulder support feature 136. That annular support feature 136 in turn, seats adjacent to an annular shoulder support rim 129 that is defined at the forward end of the inner wall 123 of the cassette unit housing 120. When the cap 150 is in place (i.e. as shown at FIG. 5a), the shoulder support feature 136 fits in snap-relationship between the rigid needle sheath shell 119 and the forward shoulder 111 of the syringe. This snap fitting is typically enabled after the syringe assembly has been pressed through the sleeve adapter 130 during assembly of the cassette unit 101.

The sleeve adapter 130 for the syringe 110 interacts with the inner wall 123 of the cassette unit housing 120, which thereby acts to constrain the position of the sleeve adapter 130 and syringe 110 within the cassette unit housing 120. The inner wall of the cassette unit housing 120 also prevents the flexible fingers 135, 138 of the sleeve adapter 130 from flexing outwards when injection loads are applied to the syringe 110. With the flexible fingers 138 of the forward end 136 of the sleeve adapter 130 securely snapped under the shoulder 111 of the syringe 110 and so prevented from flexing outwards, the syringe 110 is effectively secured within the cassette unit housing 101. Were this not to be the case the force applied to the syringe 110 during injection could conceivably push the forward fingers 138 open and enable the syringe 110 to push through.

Figure 15:
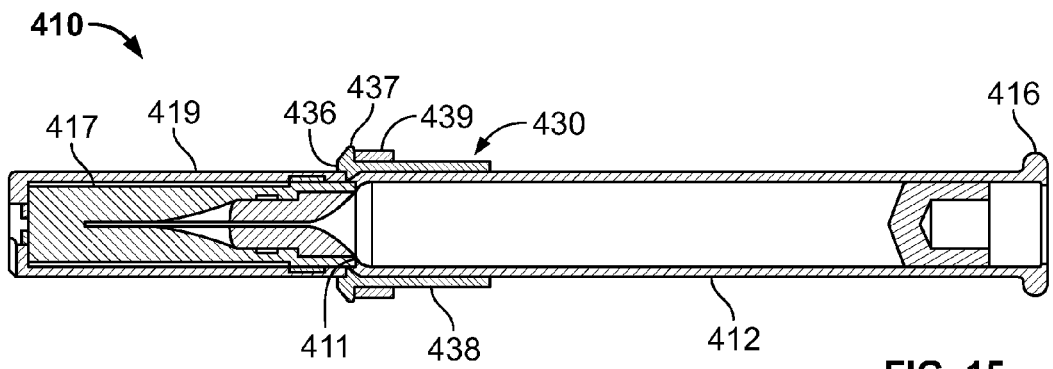
FIG. 15 is a sectional view of the alternative syringe with shoulder support assembly of FIG. 13.

FIGS. 13 to 15 show different views of an alternative shoulder support arrangement, which is again arranged such that a majority of the load path travels through the forward shoulder 411 of the barrel 412 of the syringe 410 and lesser load to pass through the flange 416 at the rear end thereof. In embodiments, the shoulder support arrangement allows for accommodation of manufacturing tolerances and/or acts to prevent shear stress. Variants of this alternative shoulder support arrangement are suitable for use with any of the cassette units 1; 101; 201; 301 described herein.

The alternative shoulder support arrangement makes use of sleeve adapter 430 having flexible fingers 438 with end tabs 437 at the forward end 436 thereof and securing ring 439 (e.g. formed of metal). In the supporting position shown at FIGS. 14 and 15, the sleeve adapter 430 seats over the forward shoulder 411 of the syringe 410 and securing ring 439 is pushed forwards up to the end tabs 437 to draw the flexible fingers 438 into securing relationship with the forward syringe shoulder 411. This movement of the ring 439 to the securing position is typically made after the syringe assembly comprising syringe 410 and needle cover comprising needle sheath 417 and rigid needle sheath shell 419 has been pressed through the sleeve adapter 430 during the assembly operation.

Figure 7:
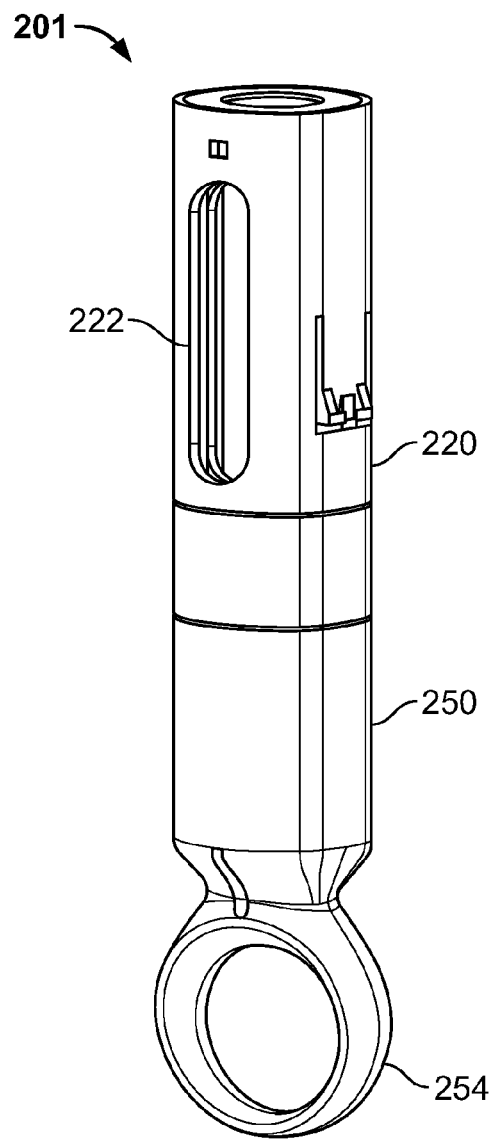
FIG. 7 is a perspective view of a third cassette unit of an auto-injector herein arranged for use with a 2.25 ml syringe and shown in the 'pre-use' configuration.
Figure 8:
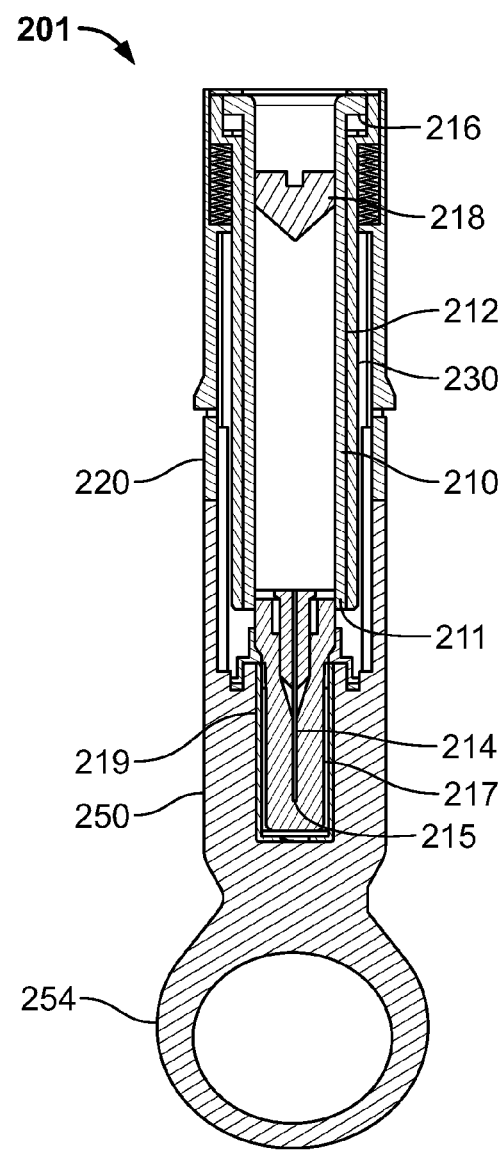
FIG. 8 is a sectional view of the third cassette unit of FIG. 7 also in the 'pre-use' configuration.
Figure 9:
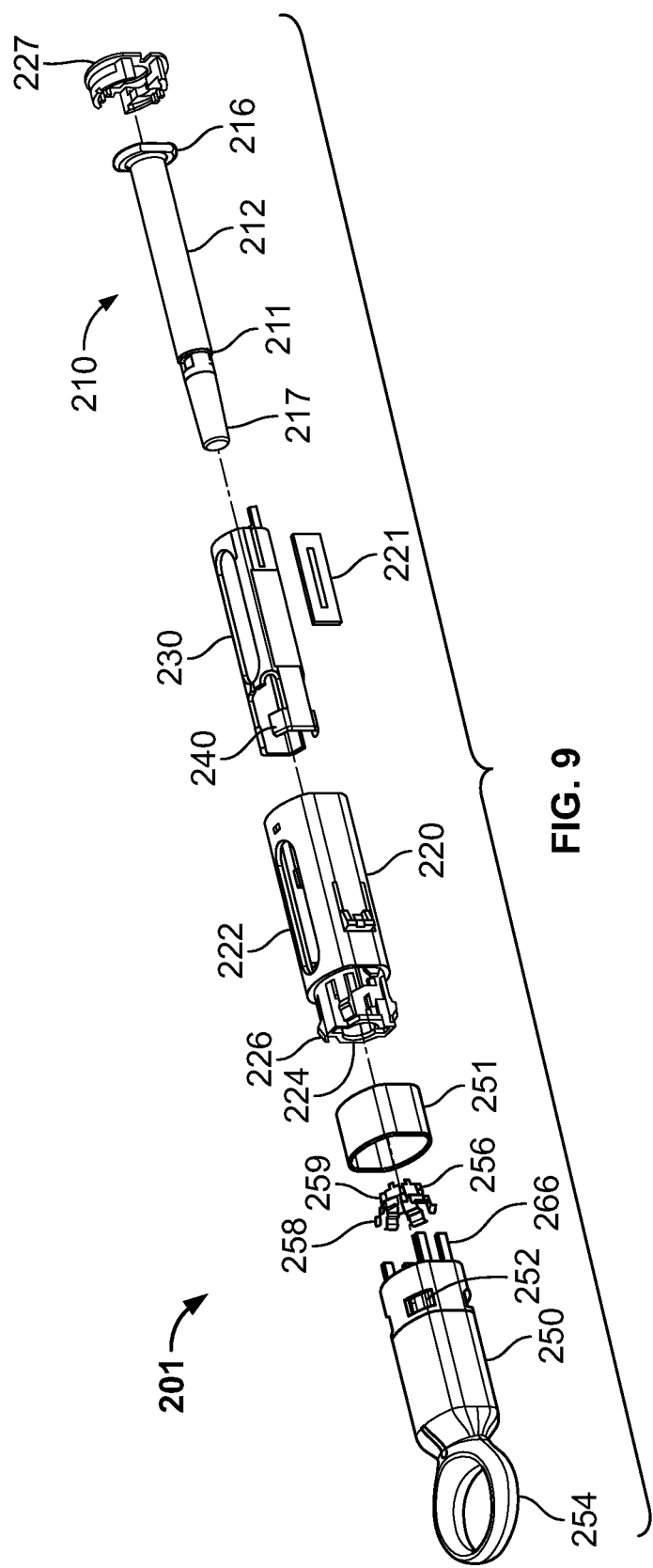
FIG. 9 is an exploded view of the third cassette unit of FIG. 7.
Figure 10:
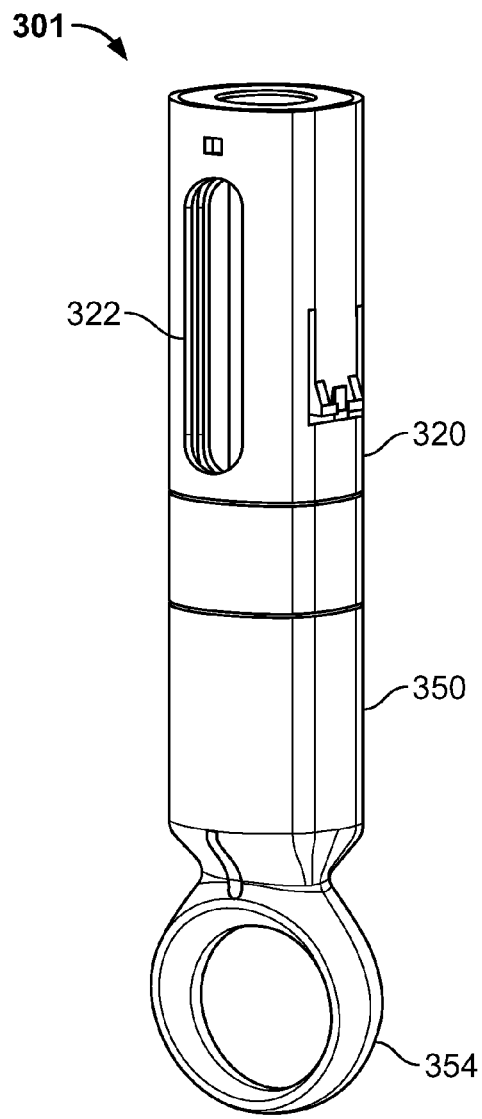
FIG. 10 is a perspective view of a fourth cassette unit of an auto-injector herein arranged for use with a 1 ml syringe and shown in the 'pre-use' configuration.
Figure 11:
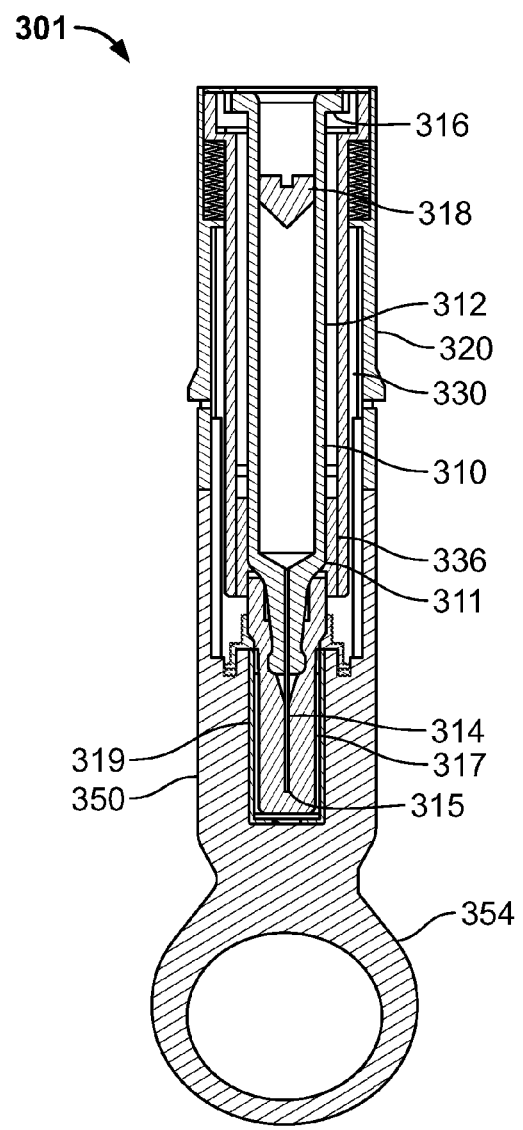
FIG. 11 is a sectional view of the fourth cassette unit of FIG. 10 also in the 'pre-use' configuration.
Figure 12:
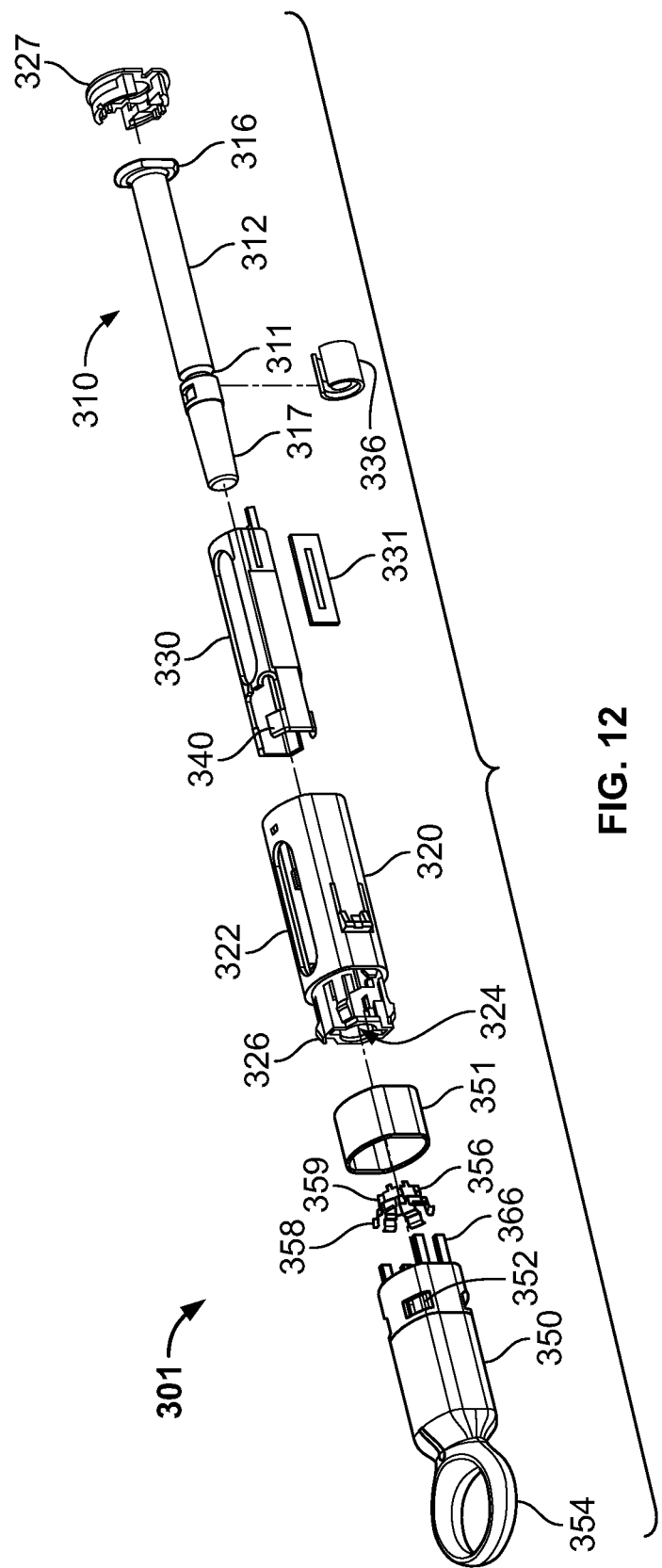
FIG. 12 is an exploded view of the fourth cassette unit of FIG. 10.

FIGS. 7 to 9 show a third cassette unit of an auto-injector herein arranged for use with a 2.25 ml syringe. FIGS. 10 to 12 show a fourth cassette unit that may be appreciated to be a variant of the third cassette unit, but adapted to receive a smaller 1 ml syringe.

The third cassette unit 201 of FIGS. 7 to 9 is arranged for use with a syringe 210 that contains a liquid drug formulation (not shown). The cassette unit 201 comprises an elongate form cassette unit housing 220 having an end cap 227 that is arranged for receipt of the syringe 210 and is sized and shaped for this purpose. The cassette unit housing 220 is provided with a viewing window 222 that allows for viewing of the contents of the syringe 210 to check for dispensing thereof. The cassette unit housing 220 is further provided with security label 221, which may in aspects be an RFID tag label for use in verification purposes. The cassette unit 201 is provided with a removable cap 250 that is arranged to engage the needle cover of the syringe 210 that is shown at FIGS. 7 and 8 in the capped position. Label 251 fits over cap 250. The cap 250 is provided at the brim thereof with a peripheral arrangement of through-hole first engagement features 252 and also with insert 266 whose arms protrude out-with the cap 250. The cap 250 is shaped to define a ring pull 254 for receipt by the finger of a user.

Needle cover gripper 256 in the form of a cage-like (or 'flower') structure and defining plural gripping elements 258 arranged about a central hub 259 is further provided to the removable cap 250. Such gripping elements 258 are arranged for gripping of the needle cover 217, 219 on removal of the removable cap 250 such that removal of the cap 250 also results in removal of the needle cover 217, 219 and hence, unsheathing of the needle tip 215.

The syringe 210 is of a standard 2.25 ml type and comprises a barrel 212 with end flange 216 for holding a liquid drug formulation; a hollow needle 214 at one end of the barrel 212; and a syringe plunger 218 in the form of a rubber stopper that is arranged for axial movement within the barrel 212 such as to enable the liquid drug formulation to be expelled through the hollow needle 214. The hollow needle 214 defines a needle bore, which is of circular cross-section (e.g. 23G, 25G or 27G diameter) and a needle tip 215. The needle tip 215 is sheathed by needle sheath 217, which is optionally provided with rigid needle sheath shell (not shown). The needle sheath 217 and optional rigid shell in combination define a 'needle cover'.

The cassette unit housing 220 of the cassette unit 201 is arranged to define a cassette unit housing cavity that is sized and shaped for generally fixed receipt of the syringe 210. The cassette unit housing 220 defines at its forward end a needle delivery aperture 224 through which in use, the hollow needle 214 of the syringe 210 protrudes on removal of the cap 250 there from. The cassette unit housing 220 defines at its rearward end an end cap 227 adjacent to which the end flange 216 of the syringe 210 seats.

The cassette unit 201 is provided with an inner housing sleeve 230 for sleeved receipt of the syringe 210. The cassette unit 201 may be arranged to accommodate multiple syringe sizes by providing inner housing sleeves 230 of different inner diameter.

The inner housing sleeve 230 also includes cap lock feature 240 arranged for locking interaction with the through-hole first engagement features 252 of the removable cap 250 and locking arm second engagement features 226 of the cassette unit housing 220 for selectively preventing removal of the cap 250 from the cassette unit housing 220 and also for preventing rotation of the cap 250 relative to the cassette unit housing 220

FIGS. 10 to 12 show a fourth cassette unit 301 that is a variant of the third cassette unit 201, but now adapted to receive a smaller syringe 310 of 1 ml capacity.

Thus, fourth cassette unit 301 of FIGS. 10 to 12 is arranged for use with a 1 ml syringe 310 that is arranged to contain a liquid drug formulation (not shown). The cassette unit 301 comprises an elongate form cassette unit housing 320 with viewing window 322 that is arranged for receipt of the syringe 310 and is sized and shaped for this purpose. The cassette unit 301 is again provided with a removable cap 350 defining a peripheral arrangement of through-hole first engagement features 352 and ring pull 354, which cap 350 is shown at FIGS. 10 and 12 in the capped position. The cap 350 is also provided with insert 366 whose arms protrude out-with the cap 350. Label 351 fits over cap 350. Again, the removable cap 350 is provided with a needle cover gripper 356 in the form of a cage-like (or 'flower') structure and defining plural gripping elements 358 arranged about a central hub 359.

The syringe 310 is of a standard 1 ml type and comprises a barrel 312 with end flange 316 for holding a liquid drug formulation; a hollow needle 314 at one end of the barrel 312; and a syringe plunger 318 in the form of a rubber stopper that is arranged for axial movement within the barrel 312 such as to enable the liquid drug formulation to be expelled through the hollow needle 314. The hollow needle 314 defines a needle bore, which is of circular cross-section (e.g. 23G, 25G or 27G diameter) and a needle tip 315. The needle tip 315 is sheathed by needle sheath 317, which is optionally provided with rigid needle sheath shell (not shown). The needle sheath 317 and optional rigid shell in combination define a 'needle cover'.

The cassette unit housing 320 of the cassette unit 301 is arranged to define a cassette unit housing cavity that is sized and shaped for generally fixed receipt of the syringe 310. The cassette unit housing 320 defines at its forward end a needle delivery aperture 324 through which in use, the hollow needle 314 of the syringe 310 protrudes on removal of the cap 350 there from. The cassette unit housing 320 defines at its rearward end an end cap 327 adjacent to which the flange end 316 of the syringe 310 seats.

The cassette unit 301 is provided with an inner housing sleeve 330 for sleeved receipt of the syringe 310. The housing sleeve 330 of this fourth cassette unit 301 has a smaller effective inner diameter to that of the housing sleeve 230 of the third cassette unit 201, but has the same effective outer diameter. Thus, the inner housing sleeve 330 of the fourth cassette unit 301 can function similarly to the sleeve adapter 130 of the second cassette unit 101 herein and allow for accommodation of the smaller 1 ml syringe.

Applicant has found that to reduce the risk of the smaller 1 ml syringe 310 shattering under the loads associated with injecting the drug, it is important for a majority of the load path to travel through the forward shoulder 311 of the syringe barrel 312 and lesser load to pass through the flange 316 at the rear end thereof. Thus, a shoulder support feature is provided in the form of a ring 336 that fits in snap-relationship between the needle cover 317 and the forward shoulder 311 of the syringe 310. The inner sleeve housing 330 for the syringe 310 interacts with the inner wall of the cassette unit housing 320, which thereby acts to constrain the position thereof the sleeve adapter. The inner housing sleeve 330 is further provided with security label 331, which may in aspects be an RFID tag label for use in verification purposes.

In overall terms, the inner sleeve housing 330 acts to sleeve a major portion of the syringe barrel 312. The effect of this sleeved relationship is firstly to increase the effective diameter of the syringe barrel 312. The shoulder support feature 336 also provides reinforcement to the shoulder 311 of the syringe 310.

The inner housing sleeve 330 also includes cap lock feature 340 arranged for locking interaction with the through-hole first engagement features 352 of the removable cap 350 and locking arm second engagement features 326 of the cassette unit housing 320 for selectively preventing removal of the cap 350 from the cassette unit housing 320 and also for preventing rotation of the cap 350 relative to the cassette unit housing 320. More details of this locking arrangement are provided at FIGS. 28*a* and 28*b*.

In each of the first to fourth cassette units 1; 101; 201; 301 described hereinbefore, a removable cap 50; 150; 250; 350 is arranged to engage a needle cover 17, 19; 117, 119; 217; 317 by means of a connector 56; 156; 256; 356. In each case, removal of the removable cap 50; 150; 250; 350 therefore results in removal of the needle cover 17, 19; 117, 119; 217; 317 connected thereto such as to allow for ready unsheathing of the needle tip 15; 115; 215; 315. More detail of this relationship is now described by reference to FIGS. 16 to 24, which illustrate an exemplary arrangement of particular relevance to the first and second cassette units of FIGS. 1 to 3 and 4 to 6. It will however, be appreciated that the underlying concepts now described may be readily be re-applied more generally such as to the third and fourth cassette units of FIGS. 7 to 9 and 10 to 12 respectively.

Figure 16:
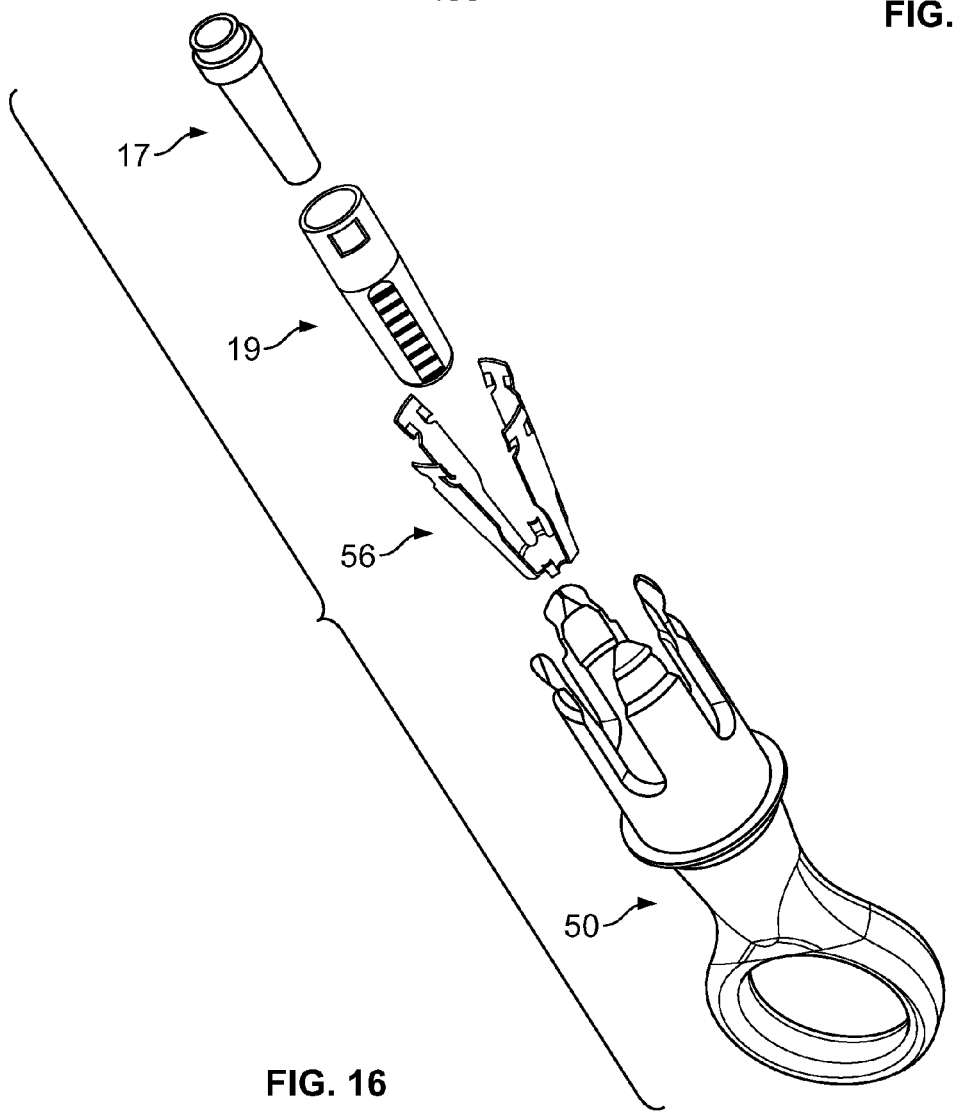
FIG. 16 is an exploded view of a removable cap assembly for use with the first and second cassette units of FIGS. 1 to 3; and 4 to 6 respectively showing an exemplary mating relationship between a needle cover, a connector, and a removable cap.

FIG. 16 illustrates an exemplary mating relationship between first needle cover comprising needle sheath 17, connector 56 and removable cap 50 to form in combination a removable cap assembly. The connector 56 receives the needle cover 17 and the removable cap 50 receives the connector 56 having the needle cover 17 enclosed within. In use, the patient can easily remove the cap assembly 17, 50, 56 and thereby, expose the needle 14 by simply pulling the removable cap 50 away from the cassette unit 1. The needle cover 17 of FIG. 16 may readily be adapted to include a rigid needle shield 19, as described in FIGS. 18*a* to 19.

Figure 17A:
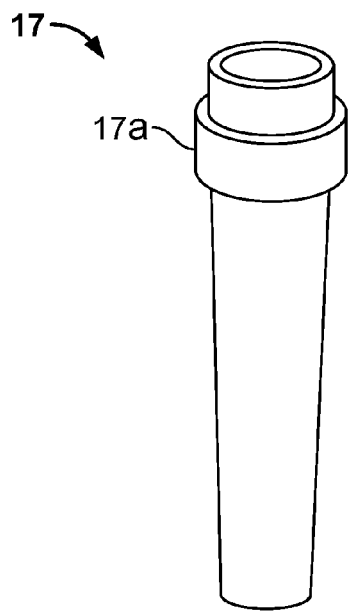
FIGS. 17a and 17b are perspective and cross sectional view of a first needle cover for use with the removable cap assembly of FIG. 16.
Figure 17B:
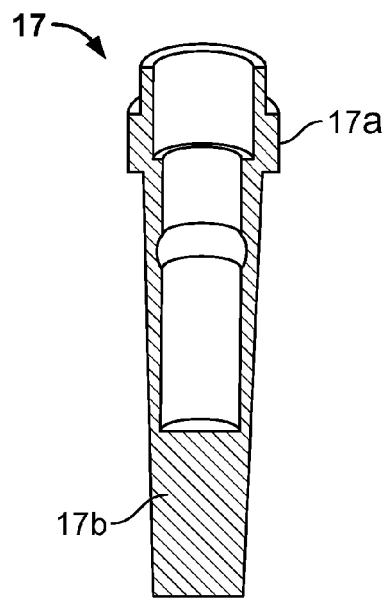

FIG. 17*a* depicts a perspective view of an exemplary embodiment of a sheath-like needle cover 17, which is cylindrical in shape and defines a shoulder 17*a* at the rear end. The needle sheath 17 may be made out of rubbery material that allows a portion of the connector 56 to dig into the outer surface thereof, such as that defined by the shoulder 17a to permanently engage the needle sheath 17 to the connector 56. FIG. 17b shows a cross sectional view of the same needle sheath 17. As depicted, the needle cover 17 includes a needle receiving portion 17b that is arranged in use, for piercing receipt of the tip 15 of the needle 14 as for example, shown at FIGS. 2 and 5. In embodiments, the needle receiving portion 17b is made from butadiene rubber. In certain embodiments, the needle sheath 17 is hollow, but other shaped arrangements of the interior of the needle sheath 17 are possible such as the one illustrated at FIG. 19.

Figure 18A:
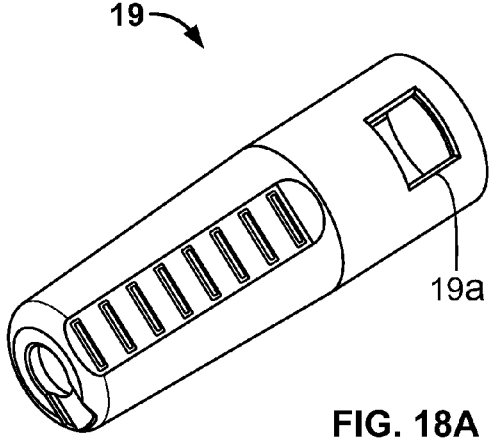
FIGS. 18a and 18b are perspective and cross sectional view of a rigid needle shield for use with the needle cover of FIGS. 17a and 17b.
Figure 18B:
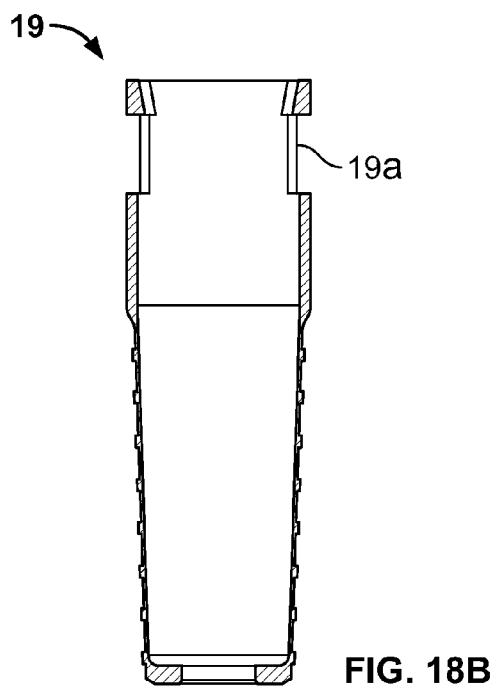
Figure 19:
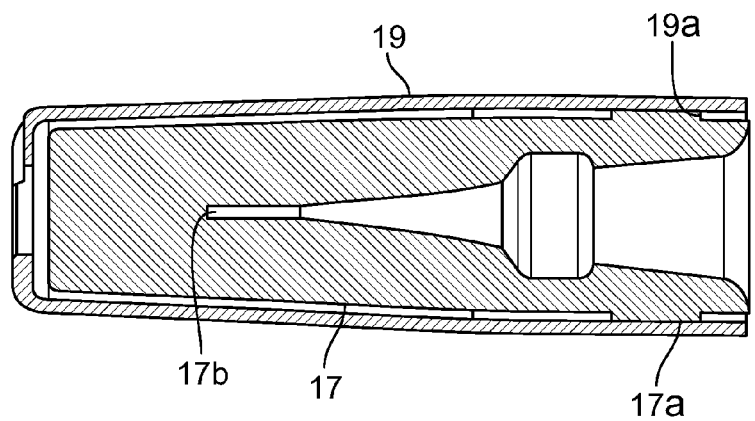
FIG. 19 is a cross sectional view of the rigid needle shield of FIGS. 18a and 18b arranged about the needle cover of FIGS. 17a and 17b and for use with the removable cap assembly of FIG. 16.

FIGS. 18a and 18b show views of a rigid needle shield 19 for use with the needle sheath 17 of FIGS. 17a and 17b. Rectangular openings 19a are provided at the rear end of the needle shield for receipt of the shoulder 17a of the needle sheath 17. FIG. 19 shows the rigid needle shield 19 arranged about the needle sheath 17 to form a needle cover assembly, which is also suitable for use with the removable cap assembly of FIG. 16. It will be noted that the inner needle-tip receiving part 17b of the needle sheath 17 of FIG. 19 is slightly differently shaped from that of the needle sheath 17 of FIGS. 17a and 17b, but otherwise the function of the needle sheath 17 is identical.

Figures 20A, 20B:
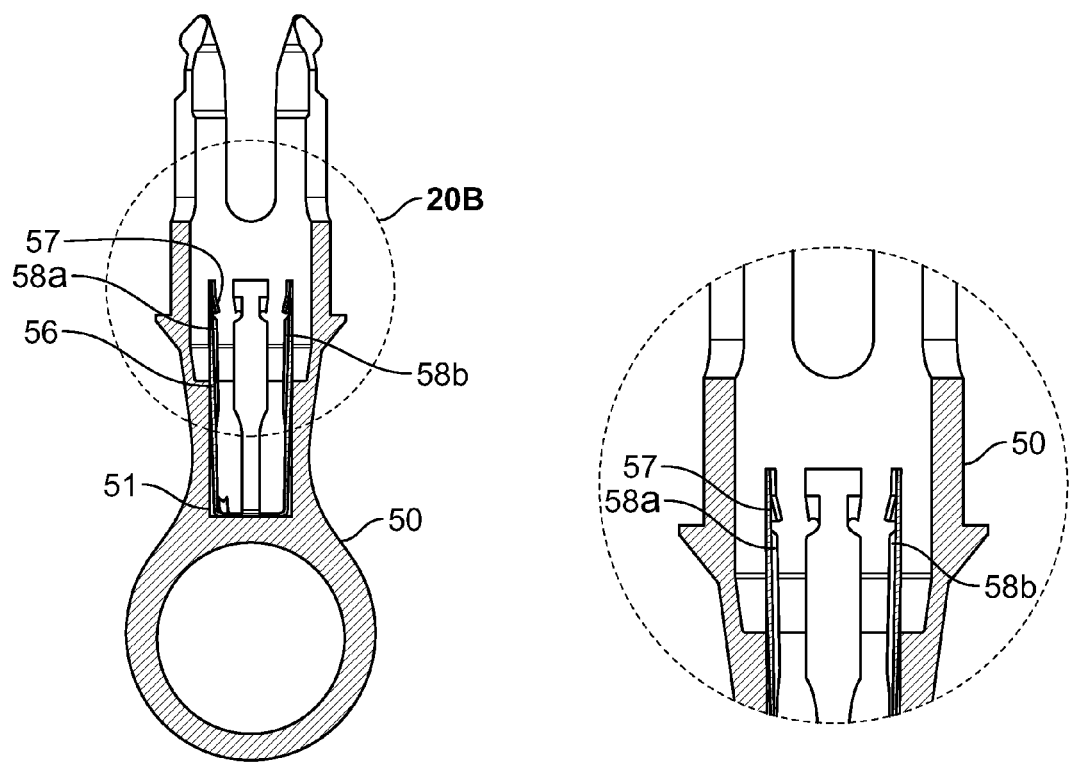
FIGS. 20a to 20c respectively show cross-sectional, cross-sectional detail and plan views of the connector and removable cap of the assembly of FIG. 16.
Figure 20C:
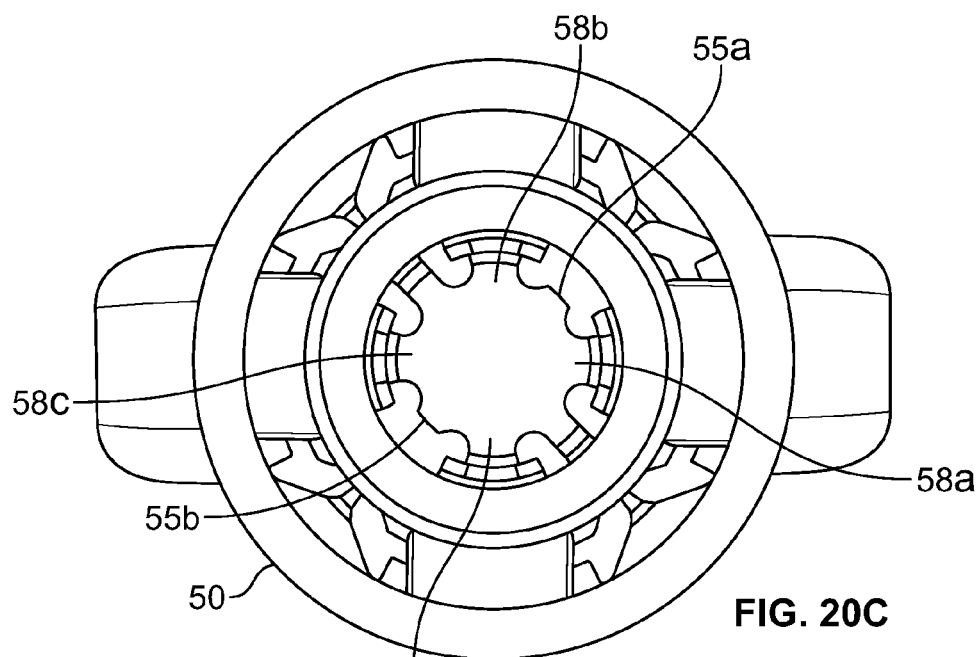

FIGS. 20a to 20c show various views of the connector 56 in combination with the removable cap 50. As shown, the initially cage-like or flower shaped connector 56, as illustrated in FIG. 22a, is bent so as to be confined within a cylindrical shaped inner cavity 51 of the removable cap 50 (see also FIGS. 21a and 21b). As a result, a plurality of first legs 58a-58d, which were initially disposed at about 80 degrees with respect to the horizontal are now about 90 degrees with respect to the horizontal. FIG. 20b shows upper internally facing barbs 57 protruding inwardly and forwardly to engage the needle cover 17 and/or rigid needle shield 19 with a connection that tightens as the removable cap 50 is pulled forwardly. This connection prevents the needle cover 17 and/or rigid needle shield 19 from being removed from the cap when a patient pulls on the removable cap 50 forwardly. FIG. 20c depicts a top view of the connector 56 being inserted in the removable cap 50. As shown, when the connector 56 is fitted within the removable cap 50, the plurality of first legs 58a-58d engage the inner surface of the removable cap 50 and the upper internally facing barbs 57 protrude inwardly and forwardly for engaging the needle cover 17 and/or rigid needle shield 19. FIG. 20c also shows the connector 56 including a second plurality of legs 55a-55b spaced symmetrically away from one another in the forward end of the connector 56. In some embodiments, the second plurality of legs 55a-55b are initially disposed more than 90 degrees (e.g., about 91 degrees to about 120 degrees) with respect to the horizontal. When the connector 56 is fitted within the removable cap 50, the second plurality of legs 55a-55b make contact with the inner surface of the removable cap 50. In some embodiments, the second plurality of legs 55a-55b dig into the inner surface of the removable cap 50 and remain fixed in place during use.

Figure 21A:
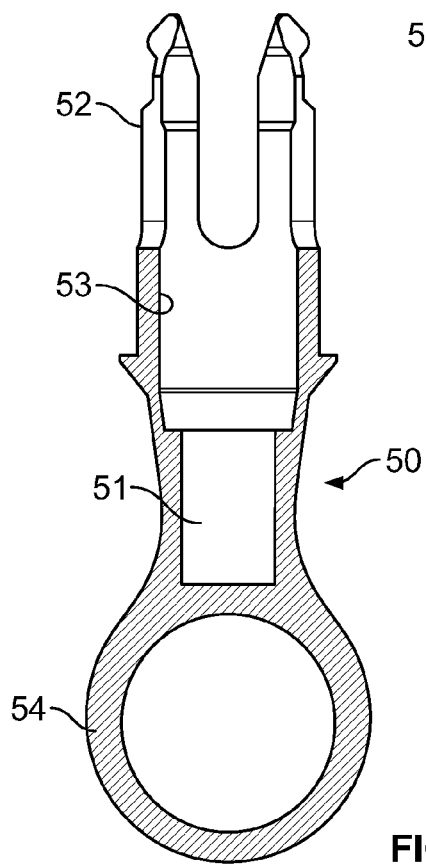
Figure 21B:
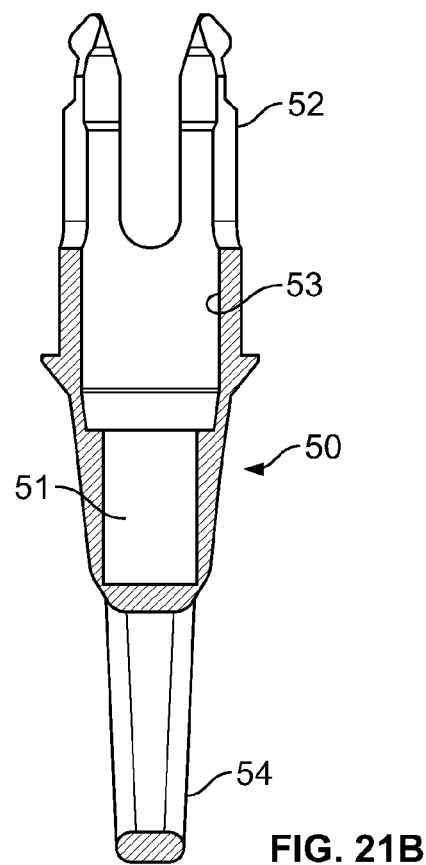

The various components of the removable cap 50 are more particularly described with reference to FIGS. 21a to 21c. As shown in FIG. 21a, the removable cap 50 defines a hollow inner space 51 shaped to receive the connector 56 and a gripping ring (ring pull') 54 shaped to receive a patient's finger or thumb. The cap 50 is provided at the brim thereof with a crown arrangement of first engagement features 52 that are sized and shaped to extend up into the cassette unit housing 20; 120 (e.g. see FIGS. 2 and 5) when the cap 50 is in the capping position. The removable cap defines an inner surface forming an orifice 53 (e.g., wider than the inner cavity 51) into which the patient can re-insert the needle after injection. As shown, the orifice 53 is wider than the forward end of the syringe barrel 12; 112.

The fitted relationship between the removable cap 50 and the syringe barrel 12; 112 is shown at FIGS. 2 and 5. The wider orifice 53 helps reduce the likelihood that a patient will inadvertently stab his or her self when attempting to replace the needle cap after injection. The inner cavity 51, which may have a cylindrical shape, extends deep into the cap 50 from the wider orifice. FIG. 21b shows a cross sectional side view of the removable cap 50 and FIG. 21c shows a top view of the removable cap 50. As shown, the removable cap 50 is symmetrical about its central axis.

The gripping ring 54 defines a finger aperture to receive a patient's thumb or other preferred finger for pulling the removable cap away from the cassette unit 1; 101 to expose the needle 14; 114. In certain embodiments, the finger aperture is adapted to receive a hook that some patients use to pull the removable cap 50 away from the cassette unit 1; 101. The removable cap 50 with gripping ring 54 makes it easier for patients to engage and disengage the needle cover 17 and/or rigid needle shield 19 from the syringe barrel 12; 112 as it does not require the patient to contort their fingers by pressing on the sides of a narrow needle cover 17/19. As noted before, the present auto-injector is intended for use by patients having compromised manual dexterity who may therefore experience difficulty pulling a conventional needle cover 17 and/or rigid needle shield 19 off the syringe 10 before self-injection. The gripping ring 54 addresses this need by allowing the patient to simply put the thumb or other preferred finger through the finger aperture 54 and pull on the removable cap to thereby remove the needle cover 17 and/or rigid needle shield 19.

FIGS. 22a to 22f show various views of the connector 56. As shown in FIG. 22a, the connector 56 includes the first plurality of legs 58a-58d spaced symmetrically away from one another. The connector 56 is made, in certain embodiments, from a thin sheet of stainless steel, formed by a tool that bends the first legs into angles with respect to the horizontal. Such configuration and the elastic nature of these legs aid in securing the needle cover 17 and/or rigid needle shield 19 to the removable cap 50. The needle cover 17 and/or rigid needle shield 19 and the removable cap 50 are also secured together through upper, internally facing barbs 57a-57c protruding from the first legs 58a-58d. The upper, internally facing barbs 57a-57c include tips 60a-60b that point toward the forward end of the connector 56 (i.e. the needle tip 15 end). As illustrated in FIGS. 22c and 22d, these barbs are spaced about the perimeter of the connector 56 near its proximal end, with each of the first legs (e.g. 58a) having two internally facing barbs (e.g. 57a-57b), and each barb containing a pair of barb tips (e.g. 60a-60b). In some embodiments, the upper, internally facing barbs 57a-57c are concaved as shown in FIGS. 22a to 22d. These barbs are shaped to engage the needle cover 17 and/or rigid needle shield 19 when the needle cover 17 and/or rigid needle shield 19 is fitted within the connector 56. More specifically, the barb tips (e.g. 60a and 60b) apply opposing force with respect to one another when they engage the needle cover 17 and/or rigid needle shield 19 as the barb tips 60a, 60b are disposed at two ends of a concaved surface (e.g. upper, internally facing barbs 57a-57c). In some embodiments, the upper, internally facing barbs 57a-57c are disposed at an angle with respect to the body of the first legs 58a-58d. This is more particularly shown in FIG. 22d. Such configuration may enhance the engagement between the needle cover 17 and/or rigid needle shield 19 and the connector 56 as added protrusion (i.e., angled disposition of the barbs 57a-57c with respect to the first legs 58a-58d) allows the barb tips 60a-60b to more securely dig into the needle cover 17 and/or rigid needle shield 19 when a user pulls the removable cap 50 forwardly. As depicted in FIG. 22d, the longitudinal axis 61 of the upper portion 62 of the first legs 58a-58d is disposed at angle [alpha] with respect to the central axis 63 of the upper, internally facing barb 57c. The central axis 63 may be disposed between about 3 degrees to about 30 degrees with respect to the longitudinal axis 61 of the first legs 58a-58d.

As noted above, the connector 56 contains a second plurality of legs 55a-55b spaced symmetrically away from one another in the forward end of the connector 56. As shown in FIG. 22e, each of the second plurality of legs contains lower, externally facing barb tips 64a-64d that point toward the rear end of the connector 56. These barbs engage a lower, interior portion of the removable cap 50, thereby barbing the connector 56 to the removable cap 50 in a manner similar to the connections between the upper, internally facing barb tips 58a-58d and the needle cover 17 and/or rigid needle shield 19 as described above. As the lower barbs 64a-64d extend proximally into the removable cap 50, these barbs 64a-64d prevent, in combination with the upper, internally facing barb tips 58a-58d, the removable cap 50 from disengaging from the connector 56.

Figure 24:
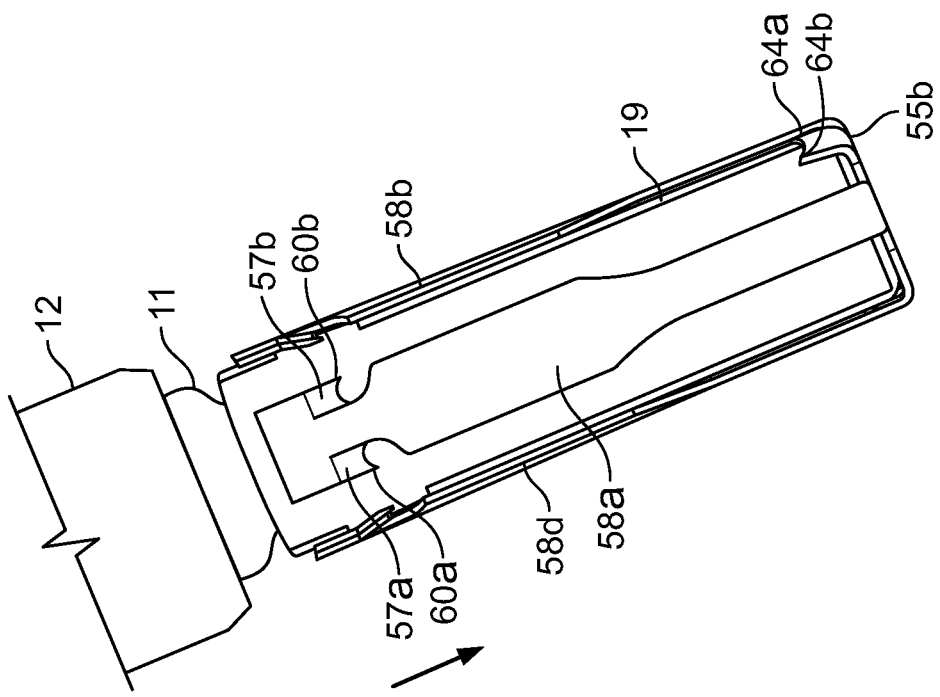
FIG. 24 is a perspective view of the removable cap assembly of FIGS. 16 and 23 with the removable cap removed for viewing clarity.
Figure 23:
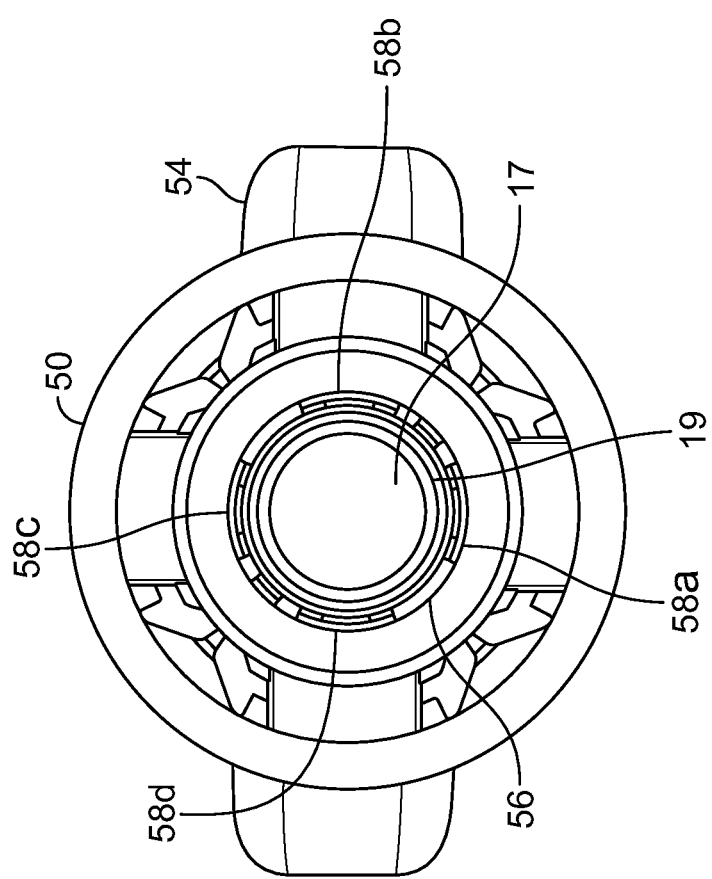
FIG. 23 is a plan view of the removable cap assembly of FIG. 16.
Figure 25:
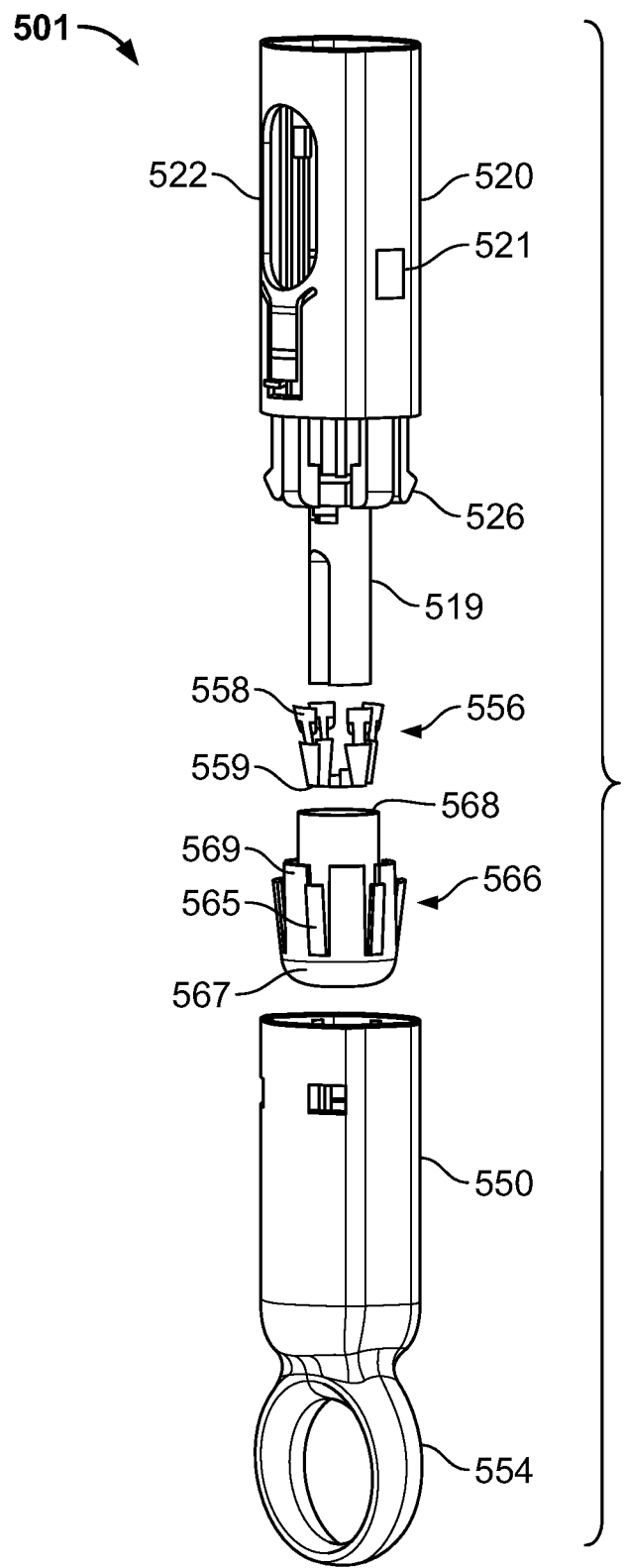
FIG. 25 is an exploded view of a fifth cassette unit of an auto-injector herein arranged for use with a 1 ml syringe.

FIGS. 23 and 24 depict an exemplary mating relationship between various components of the removable cap. More specifically, these figures show the needle cover 17 and rigid needle shield 19 being mated to the connector 56 and the connector 56 being mated to the removable cap 50. As shown, the connector 56 fits within the removable cap 50 and engages the needle cover 17 and/or rigid needle shield 19, connecting substantially permanently to the needle cover 17 and/or rigid needle shield 19 such that after engaged, if the removable cap 50 is pulled forwardly by the patient, the entire removable cap 50 and the needle cover 17 and rigid needle shield 19 covering the needle are removed as a unit, exposing the needle 14. In embodiments the rigid needle shield 19 is asymmetrical in shape. In embodiments, at least one pair of legs 58a-58d makes contact with the needle cover 17 and/or rigid needle shield 19 such that when the removable cap 50 is pulled, the entire removable cap 50 and the needle cover 17 and rigid needle shield 19 are removed as a unit. In embodiments, only one but not both pairs of legs 58a-58d connect with the needle cover 17 and/or rigid needle shield 19.

FIG. 23 depicts a top view of the removable cap 50 having the needle cover 17 and rigid needle shield 19 received within the connector 56 and the assembly being fitted within the removable cap 50. As shown, only the outermost portions of the first plurality of legs 58a-58d are visible in the top view as the upper, internally facing barbs 57 have engaged the outer surface of the rigid needle shield 19 and cannot be seen in the top view.

FIG. 24 depicts a perspective view of the assembly as depicted in FIG. 23 with the removable cap 50 removed for viewing clarity. The upper, internally facing barbs 57a-57b are adapted to receive the needle shield 19 when the needle cover 17 and rigid needle shield 19 are inserted onto the connector 56 in the direction indicated by the arrow, but the upper, internally facing barb tips 60a-60b are shaped to engage the needle shield 19 and prohibit backsliding of the needle shield 19 or removal of the connector 56 from the rigid needle shield 19 once engaged. As shown, once engaged, the tips 60a, 60b of the upper barbs 57a-57b dig into the outer surface of the needle shield 19.

In respect of all of the hereinbefore described cassette units 1; 101; 201; 301 the geometry of the removable cap 50; 150; 250; 350 is selected to allow for the needle cover 17; 117; 217; 317 to be sufficiently aligned with the needle 14; 114; 214; 314 of the syringe 10; 110; 210; 310 so that on re-capping the needle tip 15; 115; 215; 315 does not tend to catch or snag on the needle sheath 17; 117; 217; 317 inside the needle cover. Applicant has also found that it may be desirable to include further features to reduce the risk of needle catching or snagging on re-capping. FIGS. 25 to 27b show aspects of a fifth cassette unit 501 that includes such features. The fifth cassette unit 501 may be appreciated to be a variant of the fourth cassette unit 301.

The fifth cassette unit 501 is arranged for use with a 1 ml syringe 510 that is arranged to contain a liquid drug formulation (not shown). The cassette unit 501 comprises an elongate form cassette unit housing 520 with viewing window 522 and locking arms 526 that is arranged for receipt of the syringe 510 and inner housing sleeve 530 is sized and shaped for this purpose. The syringe 510 is of a standard 1 ml type having a barrel 512, needle 514, needle tip 515, needle cover 517 and other functional components identical to the 1 ml syringe of the fourth cassette unit, which for succinctness are therefore not further described. The cassette unit 501 is provided with a removable cap 550 and ring pull 554, which cap 550 is shown at FIGS. 26a to 27b in the capped position. In embodiments, the inner housing sleeve 530 also includes cap lock feature arranged for selectively preventing removal of the cap 550 from the cassette unit 501.

The removable cap 550 is provided with a spacer insert 566, which defines a central end hub 567. Inner boss 568 extends rearwards from the end hub 567 and defines a needle cover-receiving inner chamber. Outer crenellated boss 569 also extends rearwards from the end hub 567 and includes in the crenellated portions thereof flexible fingers 565, which splay out from the end hub 567 and thus, extend about the outer surface of the lower part of outer boss 569. The spacer insert 566 is often comprised of a plastic material and may be referred to as a plastic 'outer flower' structure. Inner chamber of boss 568 of insert 566 of the removable cap 550 is provided with a needle cover gripper 556 in the form of a cage-like structure and defining plural gripping elements 558 arranged about a central hub 559. The needle cover gripper 556 is often comprised of a metal and may be referred to as a metal 'inner flower' structure.

To assist with re-sheathing of the needle cover 517 and needle shield 519 on re-capping of the cassette unit 501 after an injection procedure, the position of insert 566 and connector 556 held there-within is arranged within the removable cap 550 such that end hub 567 of the spacer insert 566 is in spaced relationship to the effective end wall 549 of the removable cap 550. Having the end hub 567 in somewhat spaced relationship to the effective end wall 549 of the removable cap 550 allows for a certain 'give' in the axial position of the needle cover 517/shield 519 such that in the event of any snagging of needle cover 517/shield 519 by the needle tip 515 during re-sheathing, the spacer insert 566, connector 556 and needle cover 517/shield 519 is free to move into the 'give' space, thereby ensuring that the snagging event does not result in any bending, or even snapping, of the needle 514. The occurrence of any needle stick hazards during re-capping and re-sheathing is thus, minimized. In addition, the presence of 'give' space ensures that it is always possible to refit the cap 550, which may otherwise be prevented by needle snagging.

Figures 26A, 26B:
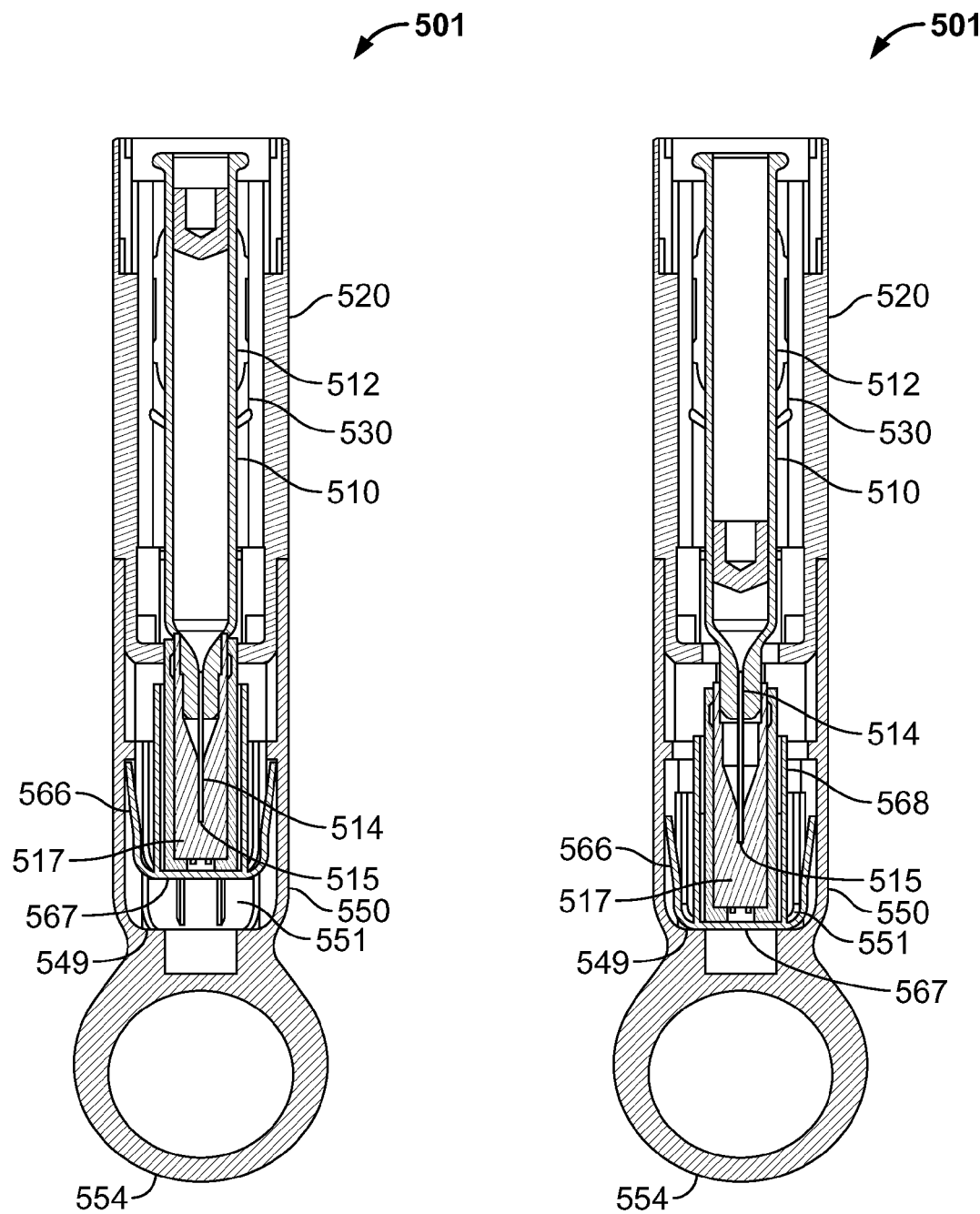
FIGS. 26a and 26b are sectional views of the fifth cassette unit of FIG. 25 at respective, first (pre-use) and second (after-use and recapping) positions.

Thus, in the first position of the cassette unit 501 as shown at FIGS. 26a and 27a it may be seen that the forward end of the central hub 567 of plastic 'outer flower' insert 566 is spaced from the end ledge 549 of the inner cavity 551 of the removable cap 550. In a second position of the cassette unit 501 as shown at FIGS. 26b and 27b, which corresponds to a post-capping configuration following an injection procedure, it may be seen that the forward end of the central hub 567 of plastic 'outer flower' insert 566 has moved into the 'give' space and now seats up against the end ledge 549 of the inner cavity 551 of the removable cap 550. In more detail, after an injection procedure as the user replaces the removable cap 550 back onto the cassette unit housing 520 the spacer insert 566 (and connector 556 and needle cover 517/shield 519 there-within) is free to move into the 'give' space defined between forward end of central hub 567 and end ledge 549. This movement will only happen if resistance to re-capping is created by interaction of the needle 514/needle tip 515 with the needle cover. By having taken up the 'give' space, any undue force on the needle 514 during the re-capping procedure has been avoided together with any risk of needle bending and/or snapping as a resulting of snagging events.

Figure 26C:
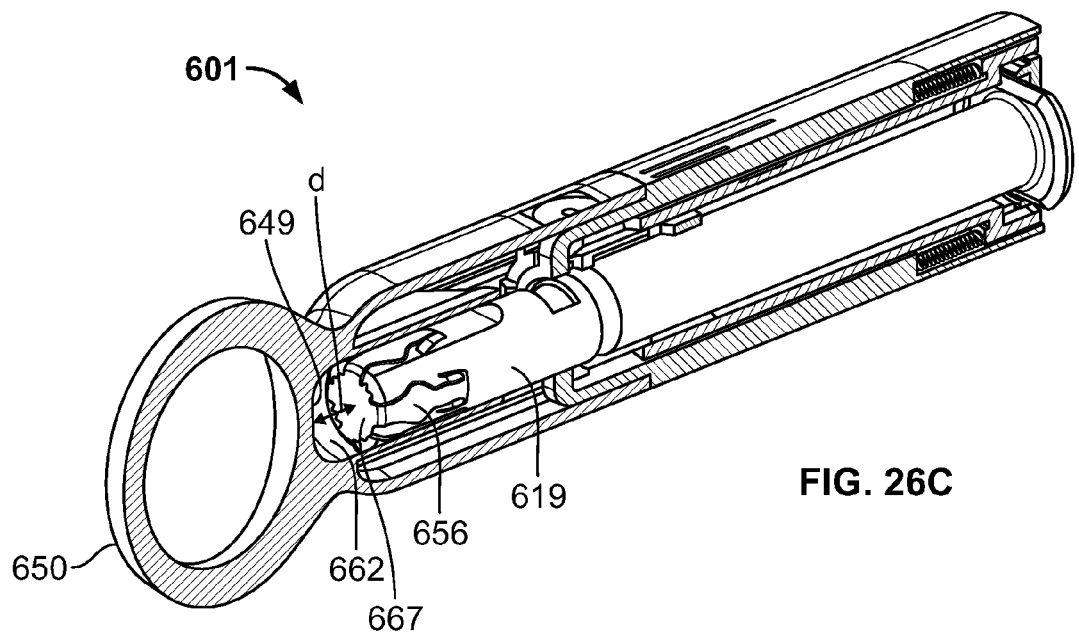
FIGS. 26c and 26d are perspective and side sectional view of a sixth cassette unit in first (pre-use) position.
Figure 26D:
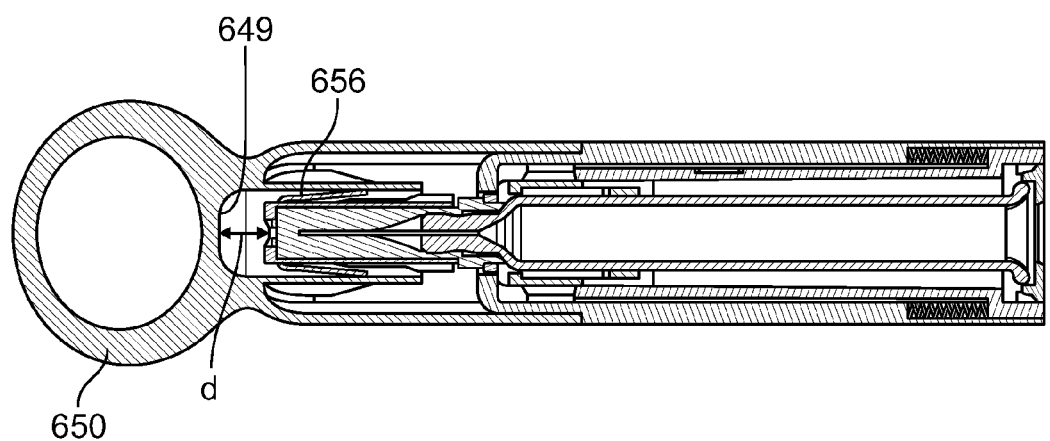
Figure 26E:
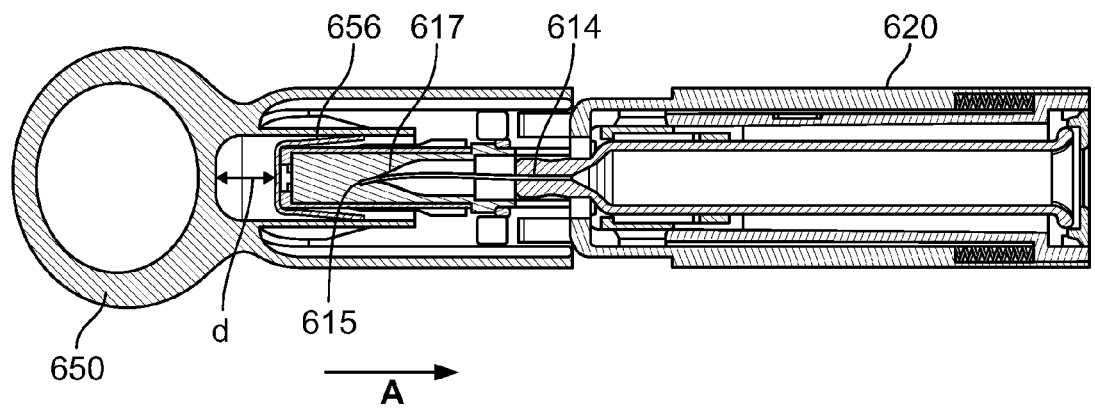
FIGS. 26e and 26f are sectional views of the sixth cassette unit in a recapping position and after-use position.
Figure 26F:
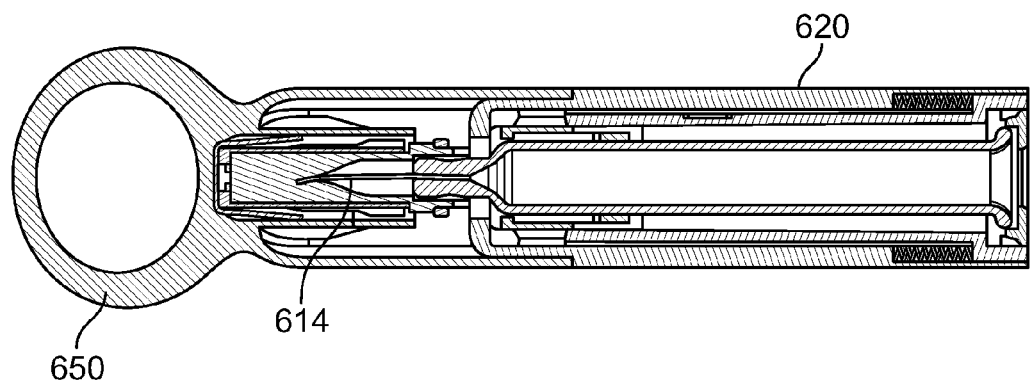

In certain implementations, the needle cover gripper 556 connects directly to the removable cap 550 without a spacer insert 566. FIGS. 26C and 26D show cross sectional views of a sixth cassette unit 601 that is ready to be used. As shown, the needle cover gripper 656 is fitted within an inner wall 662 of the removable cap 650. An end hub 667 of the needle cover gripper 656 is positioned at distance d away from the end wall 649 of the removable cap 650. This allows for a certain 'give' during re-sheathing if the needle tip 615 is misplaced within the needle cover 617/shield 619. More specifically, when the cap 650 is re-inserted onto the cassette, after injection, the removal cap 650 is allowed to travel along the distance d relative to the needle cover gripper 656. But, the force applied by the removal cap 650 during the re-capping process will not transfer directly to the needle cover gripper 656, the needle cover 617/shield 619, and the needle tip 615. This allows some flexibility for the patient to re-cap the device without being obstructed in the event the needle snags or gets caught on the side of the housing 620 during re-cap. As an example, FIGS. 26E and 26F show the removal cap 650 being recapped onto the cassette unit housing 620. More particularly, FIGS. 26E-26F show the needle tip 615 being misplaced into the needle cover 617. The needle tip 615 is now snagged in the side wall of the needle cover 617. Because the removal cap 650 is allowed to move relative to the needle cover gripper 656 (distance d as shown in FIG. 26E), the patient can continue to apply force along the arrow A to complete the re-sheathing process, and the removal cap 650 will move in the direction of arrow A without being impeded by the snagged needle tip 615. As shown, the needle cover gripper 656 and the needle cover 617/shield 619 will remain fixed in place. The cap 650 moves and occupies the space left by the distance d between the end wall 649 and the needle cover gripper 656. FIG. 26F shows the removal cap 650 that has traveled distance d to recap without breaking or bending the misplaced needle 614.

In respect of all of the hereinbefore described cassette units 1; 101; 201; 301 there is provided with a cap lock feature 40, 42; 140, 142; 240; 340 arranged for locking interaction with the engagement features 52; 152; 252; 352 of the removable cap 50; 150; 250; 350 for selectively preventing removal of the cap 50; 150; 250; 350 from the cassette unit 1; 101; 201; 301 and also for preventing rotation of the cap 50; 150; 250; 350 relative to the cassette unit housing 20; 120; 220; 320.

Details of the cap lock feature 340 of the fourth cassette unit 301 are now described by reference to FIGS. 28a to 28b. It will be appreciated that the general principles of operation of this cap locking function are applicable to each of the other cassette units 1; 101; 201; 501 described herein, As described previously, the fourth cassette unit 301 comprises an elongate form cassette unit housing 320 with second engagement features in the form of locking arms 326 arranged at the forward end thereof. The cassette unit 301 is provided with a removable cap 350 and ring pull 354. Inner housing sleeve 330 also includes cap lock feature in the form of an end-ring 340 arranged for selectively preventing removal of the cap 350 from the cassette unit 301. Operation of this cap lock feature 340 is now described.

Figure 28A:
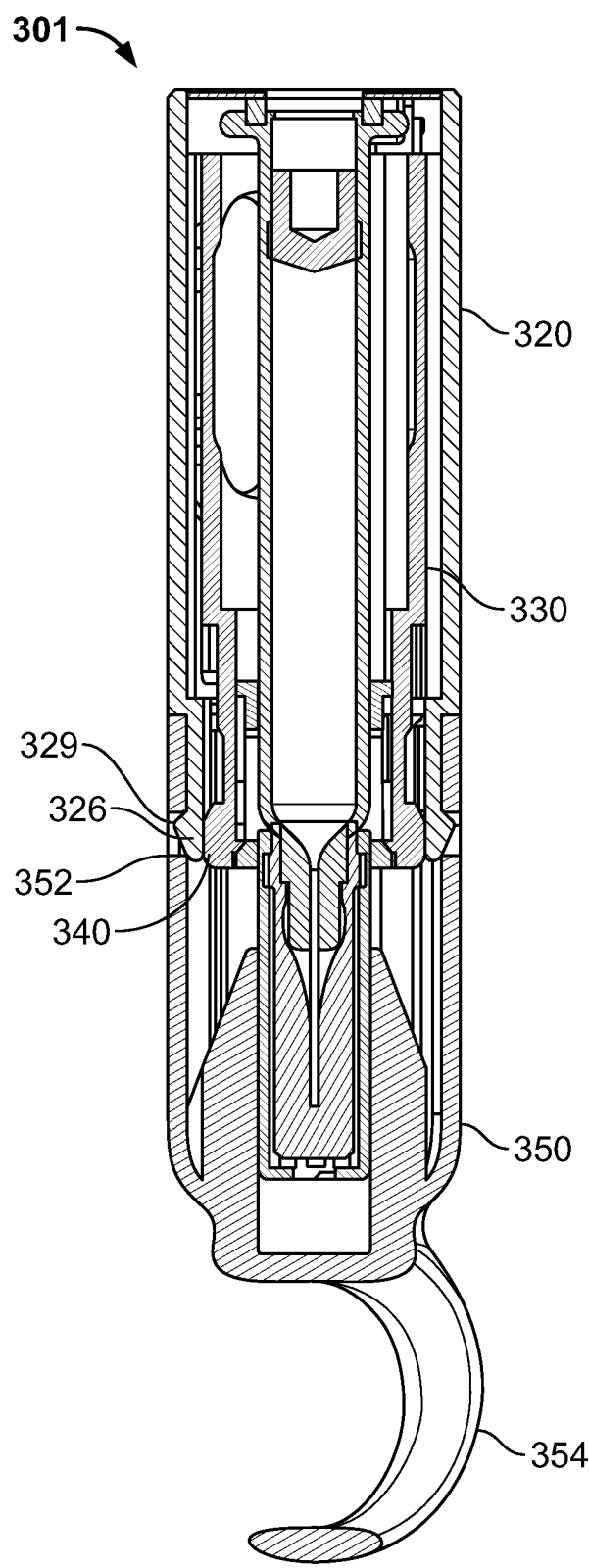
FIGS. 28a and 28b show sectional views of the fourth cassette unit of FIGS. 10 to 12 with the cap lock shown in the respective cap locked and cap unlocked positions.
Figure 28B:
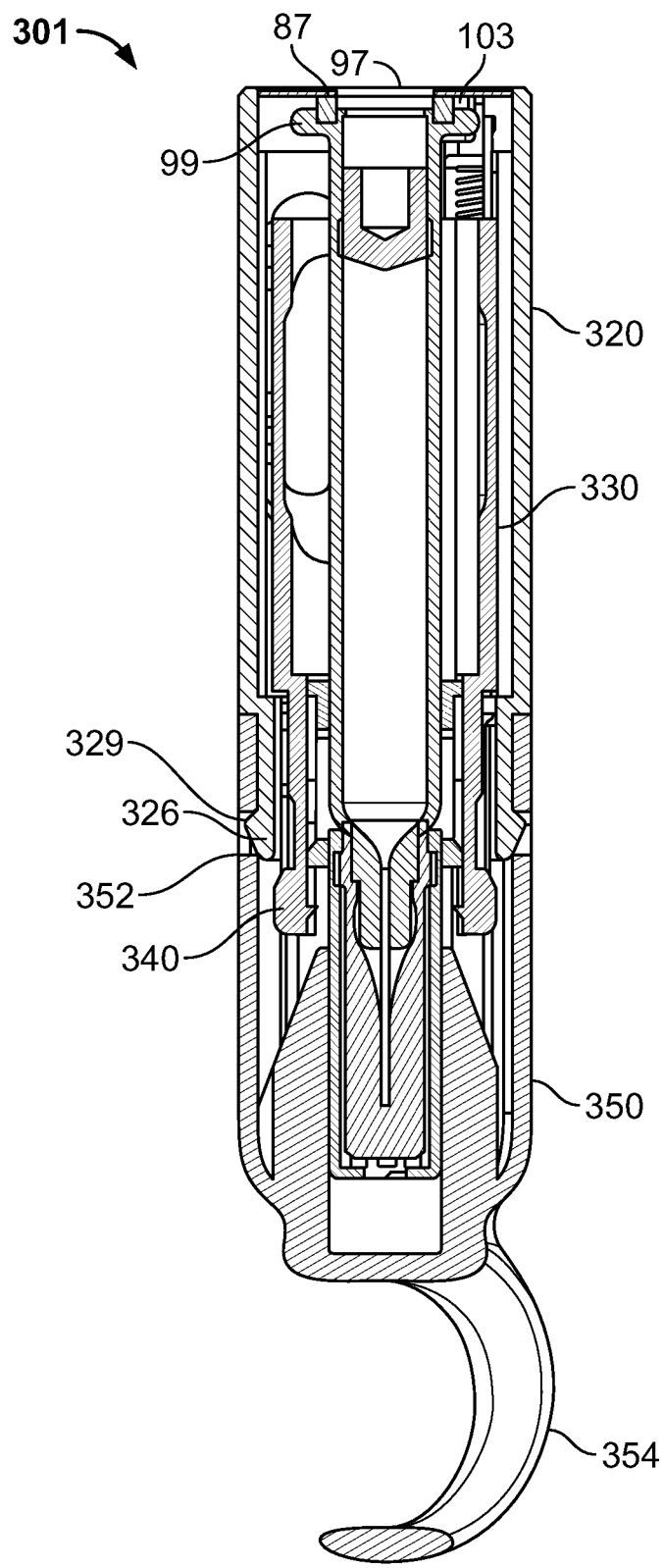

In both of FIGS. 28a and 28b, engaging tip 329 of each resilient locking arm 326 of the cassette unit housing 320 protrudes slightly into a through-hole first engagement feature 352 of the removable cap 350. It will be appreciated that this engaging interaction of the angled engaging tip 329 of locking arm 326 with rectangular through-hole feature 352 effectively prevents movement (including rotation) of the cap 350 relative to the cassette unit housing 320. It will also be appreciated that this engaging interaction can be released by pushing each locking arm 326 inwards, thereby clearing the engaging tip 329 from engaging relationship with each relevant through-hole 352. As shown, such inward pushing action on the locking arm 326 can be achieved (in the cap unlocked position of FIG. 28b) by pulling the cap 350 forwards and away from the cassette unit housing, which results in the angled tip 329 interacting with the wall edges of the through-hole 352 to push the locking arm 326 inwards. The cap lock feature 340 of the fourth cassette unit 301 operates by selectively blocking off the possibility of such inwards pushing action on the locking arms 326 to therefore prevent disengagement of tip 329 from the through-hole 352.

Thus, in the cap locked position of FIG. 28a, cap-lock ring 340 of the inner housing sleeve 330 seats up against the inner face of locking arm 326, thereby preventing any inwards movement thereof and so effectively also thereby, preventing any disengagement of the angled tip 329 of that locking arm 326 from its through-hole 352. However, in the cap unlocked position of FIG. 28b, the inner housing sleeve 330 has been moved forwards (e.g. as a result of its interaction with a mover feature of the drive unit, as described later) within the cassette unit housing 320 to a position in which cap-lock ring 340 of the inner housing sleeve 330 no longer seats up against the inner face of locking arm 326. As a result, inwards movement of the locking arm 326 is no longer prevented and disengagement of the tip 329 of the locking arm 326 from its through-hole 352 is achievable by suitable inwards pushing action on the tip 329/locking arm 326. Such inward pushing action on the locking arm 326 is achievable by pulling the cap 350 away from the cassette unit housing, which results in the angled tip 329 interacting with the wall edges of the through-hole 352 to push the locking arm 326 inwards.

FIG. 29 shows a drive unit 70 for use with any of the cassette units 1; 101; 201; 301; 501 described herein. The drive unit 70 comprises a drive unit housing 71 for housing a drive arrangement 80, which drive unit housing 71 is sized and shaped at its forward end for receipt of a cassette unit 1; 101; 201; 301; 501. FIG. 30 shows the drive unit 70 having received a representative cassette unit 1 at the docking position, wherein ring pull 54 of the removable cap 50 protrudes from the drive unit housing 71. The drive unit housing 71 is provided with a user-interface in the form of a screen 72, which may in embodiments be a touch-sensitive screen 72.

Figure 31:
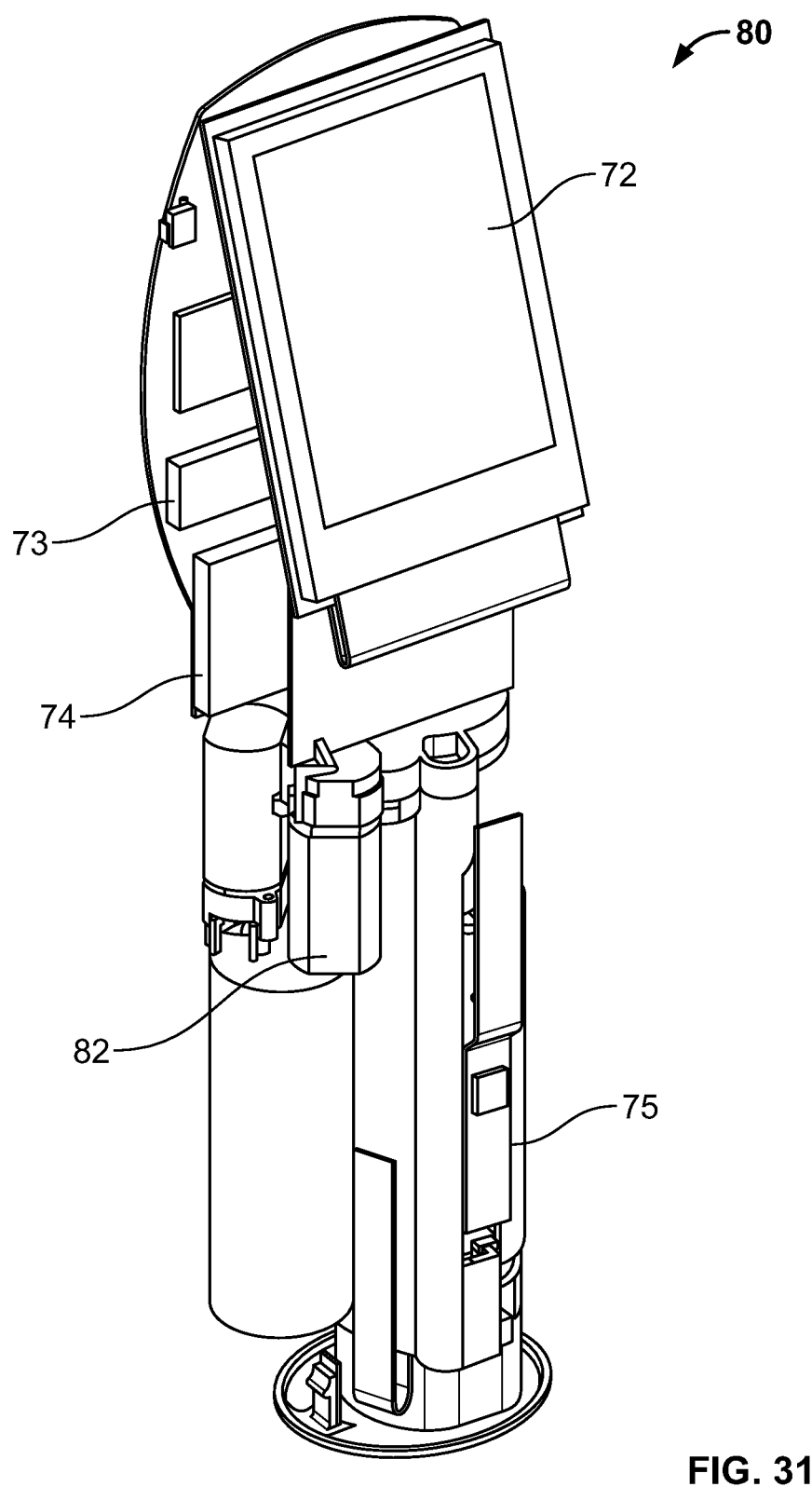
FIG. 31 is a perspective view of the first drive unit of FIG. 29 with the outer cover removed to show the drive arrangement thereof.
Figure 32:
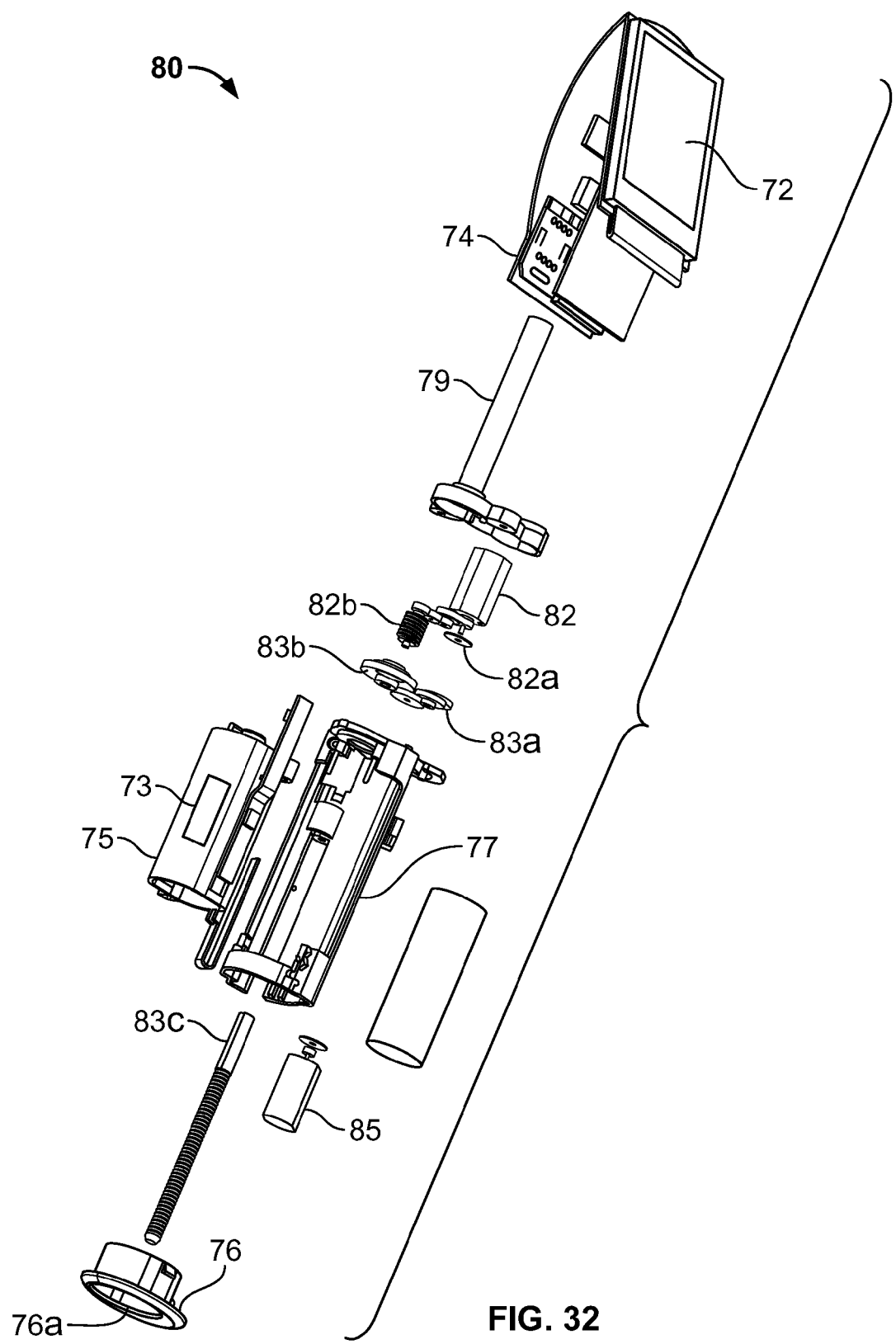
FIG. 32 is an exploded view of the first drive unit of FIG. 29 with the outer cover removed to show the drive arrangement thereof.

FIGS. 31 and 32 shows the inner workings of the drive unit 70 of FIGS. 29 and 30, which has been configured in particular for use with the third, fourth and fifth cassette units 201; 301; 501 herein. User-interface 72 may be seen to communicate with circuit board 74, which comprises electronic system circuitry that provides electronic control for the drive arrangement 80 and data processing capability. Further details of a representative electronic control system herein are later described by reference to FIG. 38. The circuit board 74 may also include inputs from various sensors and other electronic components including radiofrequency ID tag reader 73, which locates on cassette unit holder 75 and which is arranged for radiofrequency interrogation of an RFID tag on the cassette unit 1. In other embodiments, the radiofrequency ID tag reader 73 locates at the drive unit at a position closer to where the cassette unit 201; 301; 501 is arranged for receipt.

The cassette unit 201; 301; 501 is received and held within the drive unit housing 71 by cassette unit holder 75, which is received within inner holder frame 77, which in turn seats at forward frame end 76, which defines a cassette-unit receiving aperture/needle delivery aperture 76a therein. Cassette unit holder 75 mounts within frame 77 and is axially (e.g. slidably) movable therein under the selective drive action of first motor 82. The first motor 82 (e.g. stepper motor) selectively transfers drive via first gear 82a to a first drive transfer element in the form of worm 82b. That worm 82b interacts with a rack (not visible, but see also FIGS. 40a to 40i) locating on the back of cassette unit holder 75 to axially move the cassette unit holder 75 and cassette unit 201; 301; 501 and syringe 10 held thereby within the frame 77 from a rest position, in which the needle 14 with tip 15 of the syringe 10 is within the drive unit housing 71 to a use position, in which the needle 14 with tip 15 protrudes from the needle delivery aperture 76a of the drive unit housing.

Second motor 85 (e.g. stepper motor) selectively communicates via second gears 83a, 83b to a second drive transfer element in the form of a threaded screw 83c having cover 79 for subsequently transferring axial drive to the plunger 18 of the syringe 10 for moving the plunger 18 within the barrel 12 of the syringe 10 to eject at least part of the volume of liquid drug formulation contained therein.

Figure 33:
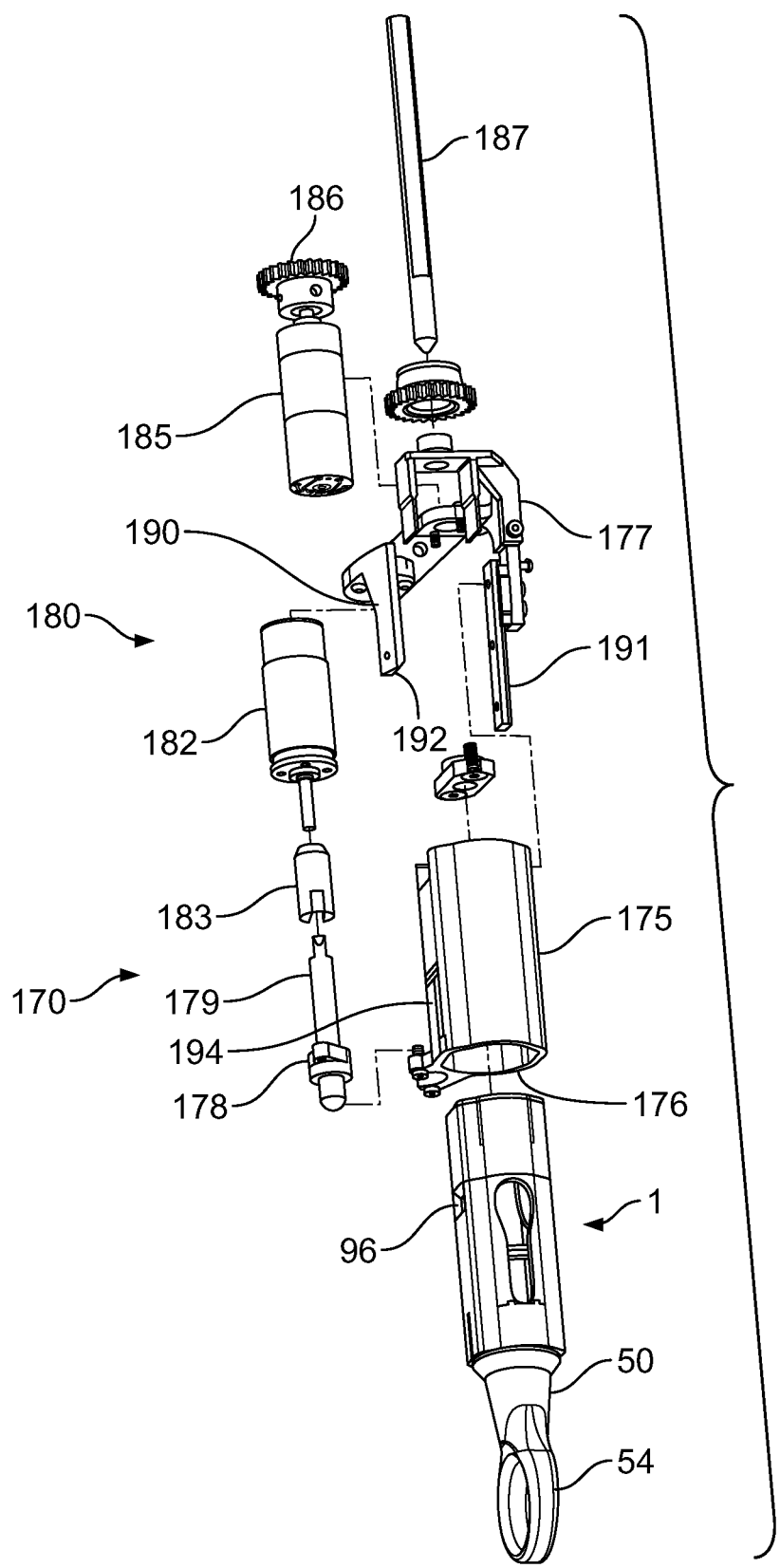
FIG. 33 is an exploded view of an alternative drive arrangement for use with the drive unit of FIG. 29, and particularly suitable for use with either of the first or second cassette units herein, and shown with the first cassette unit in non-exploded view.

FIG. 33 shows the inner workings of a second, alternative drive unit 170, which is configured in particular for use with the first and second cassette units 1; 101 herein as described herein. This drive unit 170 is now described in relation to its use with a first cassette unit 1, as described previously in relation to FIGS. 1 to 3. The drive unit 170 is shown with the outer housing and electronic system components removed and may be seen to be sized and shaped at its forward end for receipt of a representative cassette unit 1 having removable cap 50 and ring pull 54.

The cassette unit 1 is received and held within the second drive unit 170 by cassette unit holder 175, which is received within holder frame 177, which at its forward end defines a needle delivery aperture 176 therein. The holder frame 177 also defines a pusher arm 190 with ramped end 192 arranged selectively to push flexible locking arm 194 of cassette unit holder 175 into locking interaction with locking aperture 96 of cassette unit 1 as will be described later by reference to FIGS. 34 to 37b. Cassette unit holder 175 attaches via threaded coupling 178 to lead screw 179 and is axially drivable thereon under the selective action of the drive arrangement 180. The drive arrangement 180 comprises electrically powered source of axial drive in the form of a first stepper motor 182. Cassette holder 175 is guided axially on low friction bearing 191.

First stepper motor 182 selectively communicates via first coupling 183 to transfer drive to a first drive transfer in the form of first lead screw 179 and threaded coupling 178 for moving the cassette unit holder 175 and cassette unit 1 and syringe 10 held thereby from a rest position, in which the needle 14 with tip 15 of the syringe 10 is within the housing of the drive unit 170 to a use position, in which the needle 14 with tip 15 protrudes from the needle delivery aperture 176 of the drive unit housing.

Second stepper motor 185 also selectively communicates via second gear 186 to a second drive transfer element in the form of second lead screw 187 for subsequently transferring axial drive to the plunger 18 of the syringe 10 for moving the plunger 18 into the barrel 12 of the syringe 10 to eject at least part of the volume of liquid drug formulation contained therein.

In embodiments, the drive unit 70; 170 is arranged for sequential receipt of a cassette unit 1; 101; 201; 301; 501 herein. Thus, in embodiments, the drive unit 70; 170 is arranged for initial receipt of the cassette 1; 101; 201; 301; 501 at an intermediate pre-docking position and for subsequent transport of the cassette unit 1; 101; 201; 301; 501 to the docking position.

Figure 34:
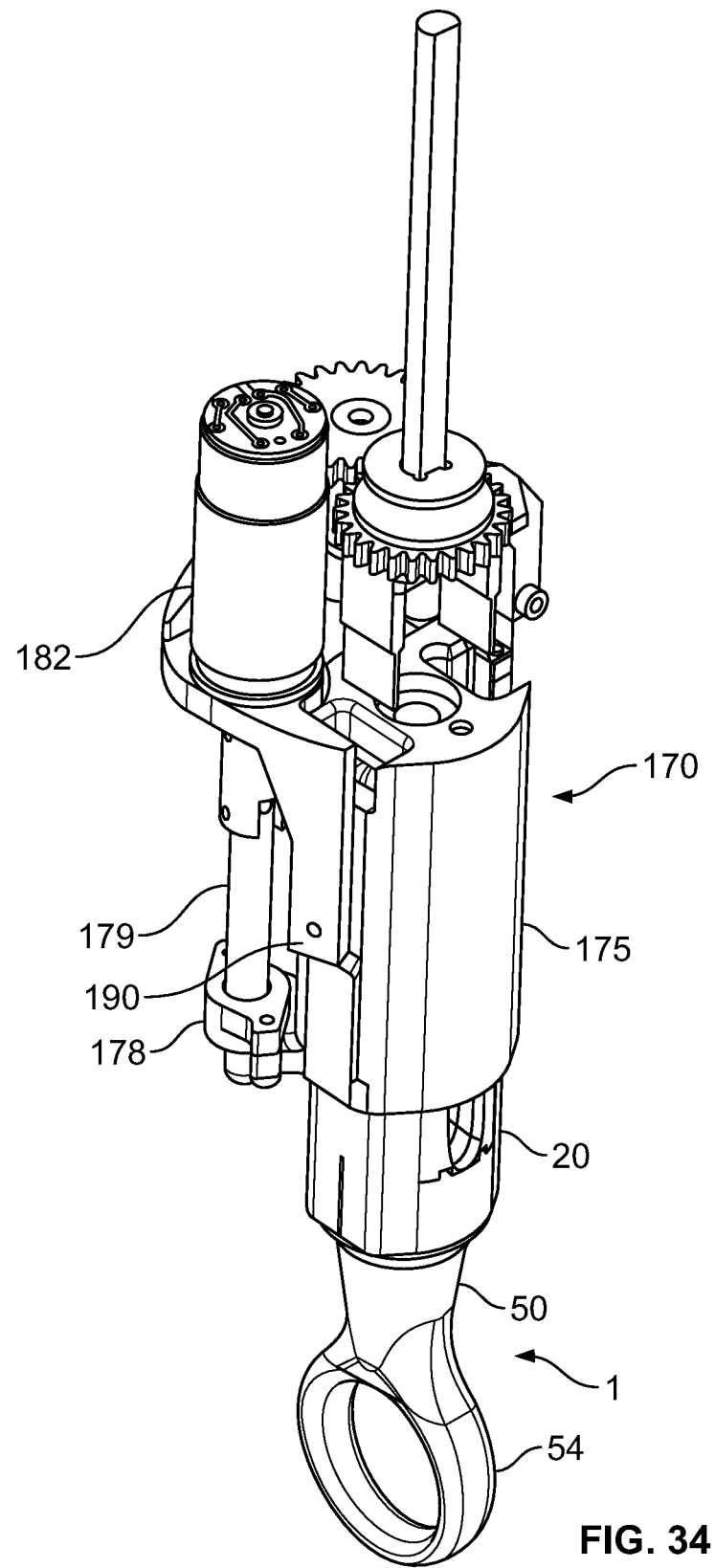
FIG. 34 is a perspective view of the alternative drive unit of FIG. 33 with a cassette unit received at an intermediate, pre-docking position.
Figure 35:
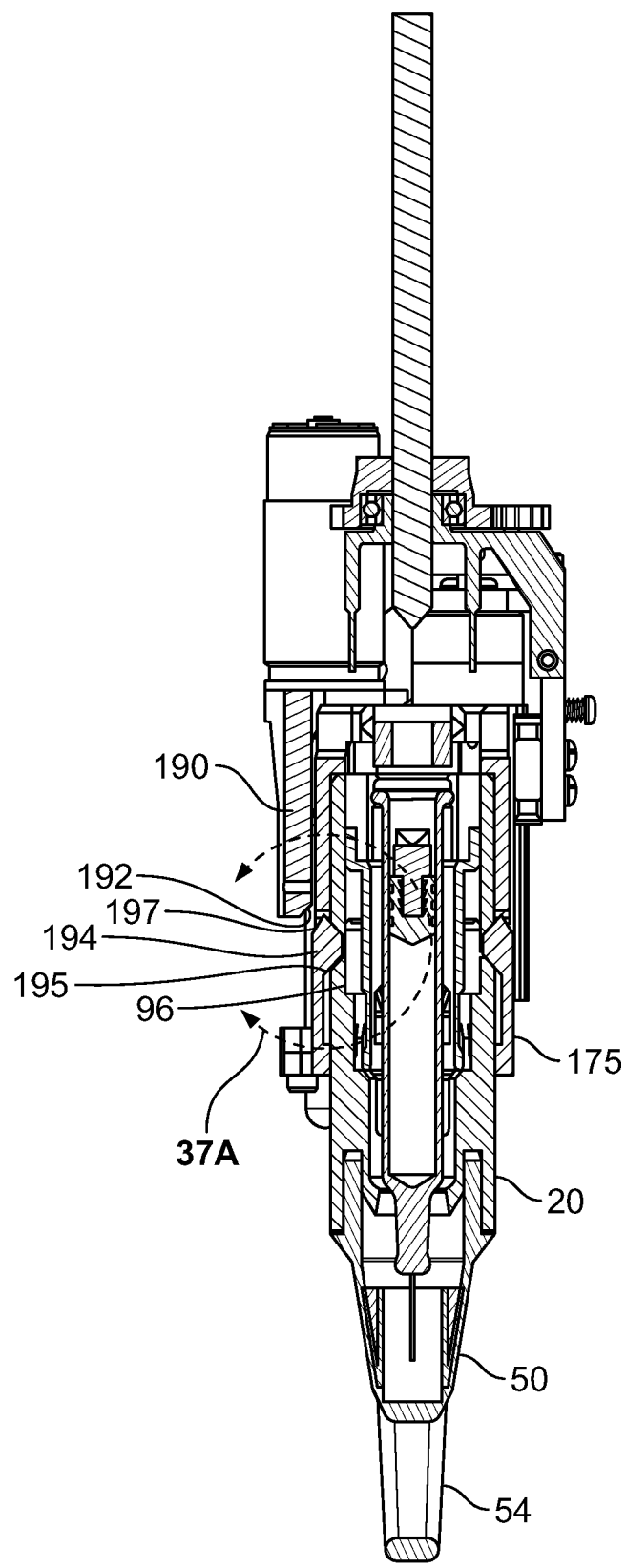
FIG. 35 is a sectional view of the alternative drive unit of FIG. 33 showing the unlocked relationship between the alternative drive unit and first cassette unit present at the intermediate, pre-docking (cassette unlocked') position.
Figure 36:
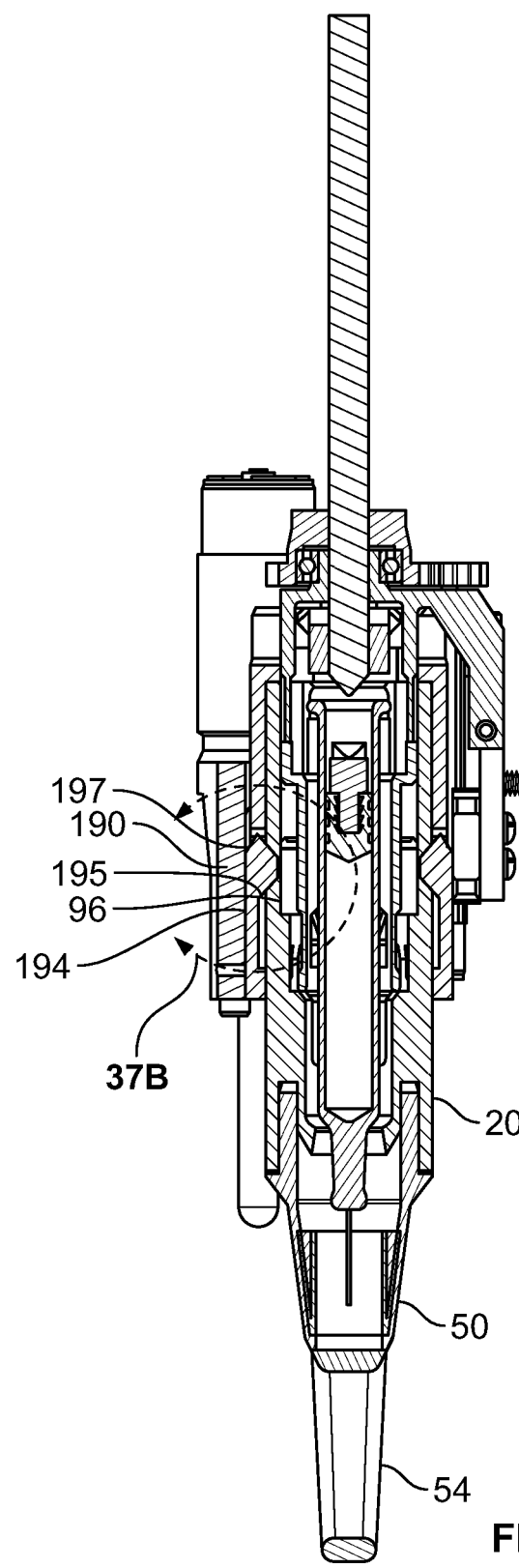
FIG. 36 is a sectional view of the alternative drive unit of FIG. 33 with the cassette unit now received at the docking (cassette locked') position.
Figure 37B:
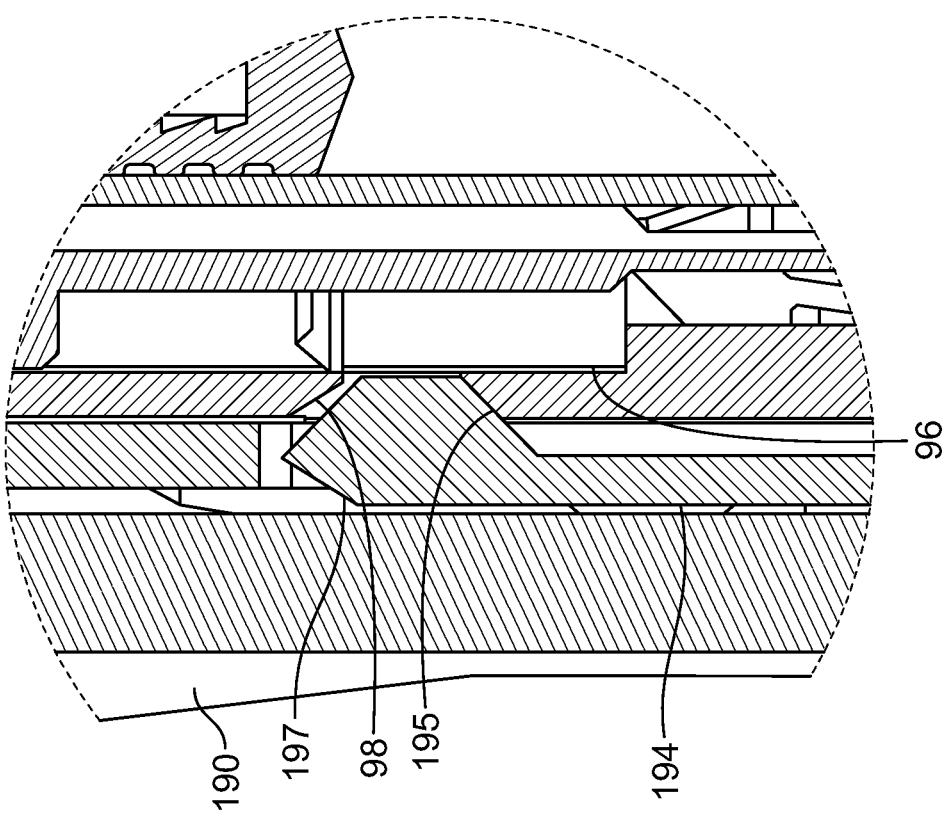
FIG. 37b is a sectional view of a detail from FIG. 36 showing the locked relationship between the drive unit and first cassette unit present at the docking position.
Figure 37A:
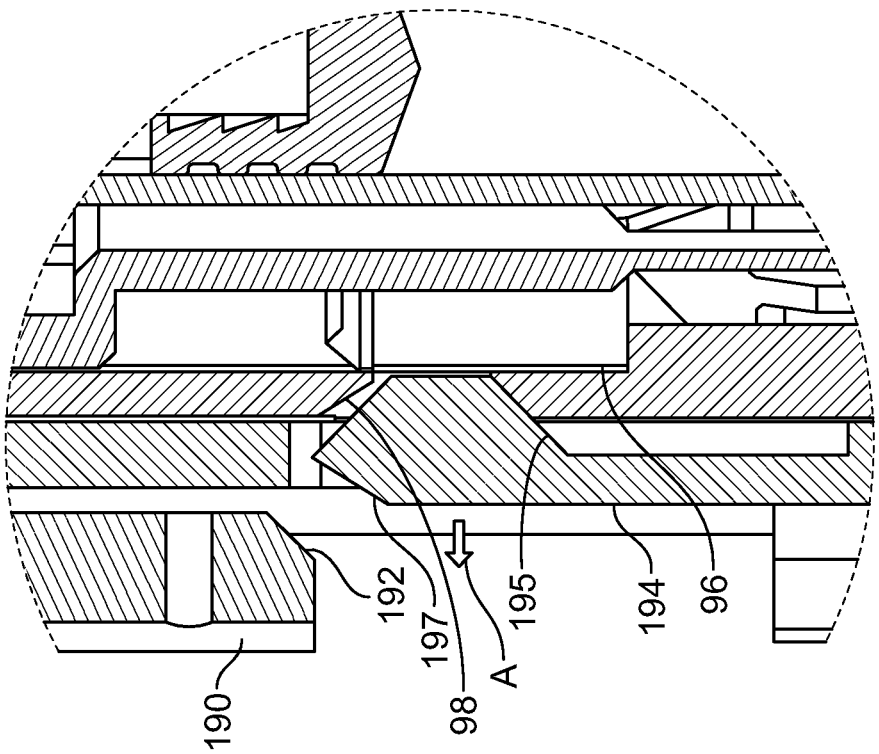
FIG. 37a is a sectional view of a detail from FIG. 35 showing the unlocked relationship between the drive unit and first cassette unit present at the intermediate, pre-docking position.

FIGS. 34 to 37b show aspects of receipt of housing 20 of representative cassette unit 1 provided with removable cap 50 and cap grip ring 54 into a second drive unit 170. FIGS. 34 and 35 show the cassette unit 1 received by the cassette unit holder 175 of the drive unit 170 at an intermediate pre-docking position. As shown in detail at FIG. 37a, in this intermediate pre-docking position the ramped end 192 of pusher arm 190 of holder frame 177 is spaced from, and therefore does not interact in pushing fashion with, the flexible locking arm 194 of cassette unit holder 175. The cassette unit 1 is therefore not yet locked into the cassette unit holder 175. In the fully docking position of FIG. 36, as shown in detail at FIG. 37b, the ramped end 192 of pusher arm has interacted with similarly ramped rear end 197 of flexible locking arm 194. In consequence, pusher arm 190 of holder frame 177 now pushes against flexible locking arm 194 of cassette unit holder 175 to maintain the locking end 195 thereof in locking interaction with locking aperture 196 of cassette unit 1. The cassette unit 1 is therefore now locked into the cassette unit holder 175. On removal of the cassette unit 1 from the device (e.g. post-injection), the inclined upper face 98 of the wall defining the locking aperture 96 acts such as to jack the flexible locking arm 194 in the direction as shown at FIG. 37a by arrow A.

In embodiments, the drive unit 70; 170 herein is arranged to initially receive the cassette unit 1; 101; 201; 301; 501 at the intermediate pre-docking position (e.g. of FIGS. 34 and 35) for automated verification thereof. Such verification can for example, be for the purpose of checking of drug and dosage information, checking that the drug is not past its expiry date and/or checking that the cassette has not been used previously. In embodiments, the cassette unit 1; 101; 201; 301; 501 further comprises an identifier 21; 121; 221; 321; 521 which may be an RFID tag and the drive unit 170 comprises a reader 73; 1050 for reading (interrogating) the identifier 21; 121; 221; 321; 521 of the cassette unit 1; 101; 201; 301; 501 and, in communication with the reader 73; 1050, a verifier (e.g. part of electronic system 74; 1001) for verifying the identifier 21; 121; 221; 321; 521.

In embodiments, the drive unit 70; 170 is arranged such that transport of the cassette unit 1; 101; 201; 301; 501 to the docking position is permitted only following positive verification of the identifier 21; 121; 221; 321; 521. Thus, only appropriately identified cassette units 1; 101; 201; 301; 501 are finally receivable into the device to enable injected drug delivery there from.

In embodiments, the drive unit 70; 170 is arranged such that transport of the cassette unit 1; 101; 201; 301; 501 from the intermediate position (e.g. of FIGS. 34 and 35) to the docking position (e.g. of FIG. 36) is permitted only following positive verification of the identifier 21; 121; 221; 321; 521. Thus, only appropriately verified cassette units are finally receivable into the device for drug delivery there from. In embodiments, that transport of the cassette unit 1; 101; 201; 301; 501 to the docking position is by automatic control under the action of the electrically powered source of drive 82; 182. Thus, in embodiments positive verification of the cassette unit 1; 101; 201; 301; 501 gives rise to a 'transport to docking position' signal from the electronic control unit 74; 1001 to the source of drive, which results in the required transporting action.

Figure 38:
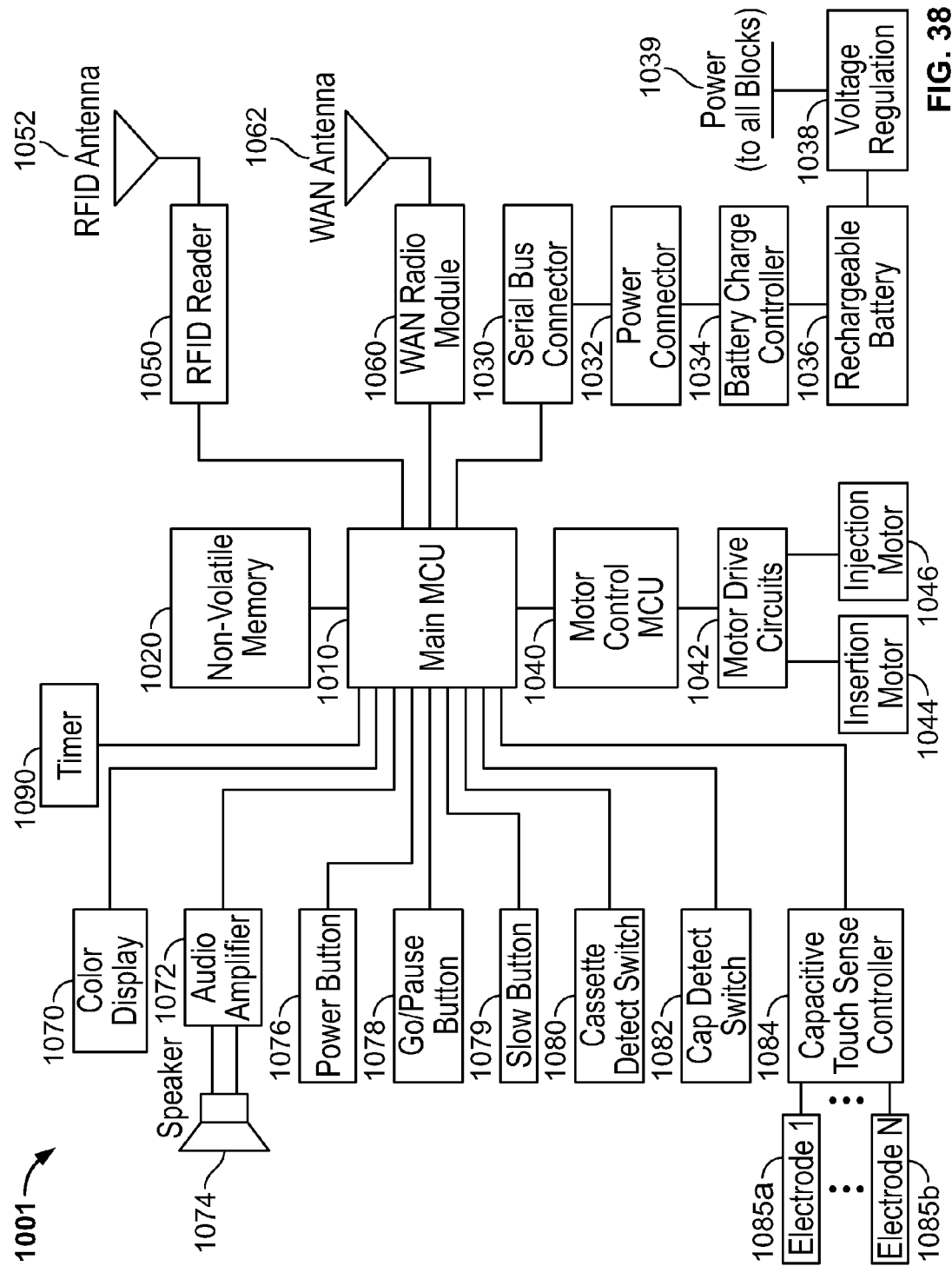
FIG. 38 is a system drawing of a suitable electronic control system for use with the drive unit of FIG. 29.

FIG. 38 shows aspects of a typical electronic control system 1001 herein. Main microprocessor control unit (MCU) 1010 communicates with the following:

Non volatile memory 1020;

Power regulating functions comprising serial bus connector 1030, which is used for power recharge and data communications; power connector 1032; battery charge controller 1034; rechargeable battery 1036; voltage regulator 1038 and power distribution 1039;

Motor control microprocessor control unit (MCU) 1040 for use in controlling the drive motor(s) 82, 85, 182, 185 and communicating with motor drive circuits 1042; insertion motor 82, 182, 1044 and injection motor 85, 185, 1046;

RFID reader 1050 with RFID antenna 1052 for use in reading an RFID tag on the cassette unit 1; 101; 201; 301; 501;

Wide Area Network (WAN) radio module 1060 with WAN antenna 1062 for use in communicating to an external computer network;

User-interface functions comprising colour display 1070; audio amplifier 1072 with speaker 1074; power button 1076; go/pause button 1078; and slow button 1079;

Sensing functions namely, cassette detect switch 1080 for detecting the presence of the cassette within the drive unit; Cap detect switch 1082 for detecting the presence of the removable cap 50; 150; 250; 350; 550 on the cassette unit 1; 101; 201; 301; 501; and capacitive touch sense controller 1084 with electrodes 1085a, 1085b (many such electrodes may be present) for detecting the presence of a user's skin;

Timer function 1090 (a sub-function of the MCU 1010)

In embodiments, the timer function 1090 of the MCU 1010 is initiated by the removal of the removable cap 50; 150; 250; 350; 550 and needle cover 17; 117; 217; 317; 517 from the cassette unit 1; 101; 201; 301; 501. In embodiments, cap detect switch 1080 detects removal of the removable cap 50; 150; 250; 350; 550 (e.g. together with needle cover 17; 117; 217; 317; 517 and rigid needle shield 19; 119; 219; 319; 519) from the cassette unit 1; 101; 201; 301; 501. The timer 1090 then starts counting. In embodiments, once the timer 1090 reaches a certain, pre-determined count a command to cancel the injection (e.g. by preventing the action of the drive/motor function of the drive unit 70; 180) is generated. Drive action of the drive unit 70; 170 is thus, prevented. In embodiments, the timer 1090 therefore acts to ensure that drug is delivered to the patient within a set time limit following removal of the removable cap 50; 150; 250; 350; 550 (e.g. together with needle cover 17; 117; 217; 317; 517 and rigid needle shield 19; 119; 219; 319; 519) from the cassette unit 1; 101; 201; 301; 501. Examples, of timers that may be used include time or actuation-based counters installed on an integrated circuit chip, such as an ePROM. Example ePROMs include those manufactured by Dallas Semiconductor.

Further aspects of the first auto-injector device herein may now be appreciated by reference to FIGS. 39a to 39i and FIGS. 40a to 40i and to the following description of a typical use operation: These show and describe sequential use steps of a first drive unit 70 essentially in accord with that already described by reference to FIGS. 31 and 32 as particularly used in conjunction with a fourth cassette unit 301 essentially in accord with that already described by reference to FIGS. 10 to 12. The first drive unit 70 includes an electronic control system (not shown) essentially of the type described by reference to FIG. 38. For clarity, only the parts of FIGS. 39a to 39i and 40a to 40i most relevant to the use operation being described are identified by labelling.

Figure 39A:
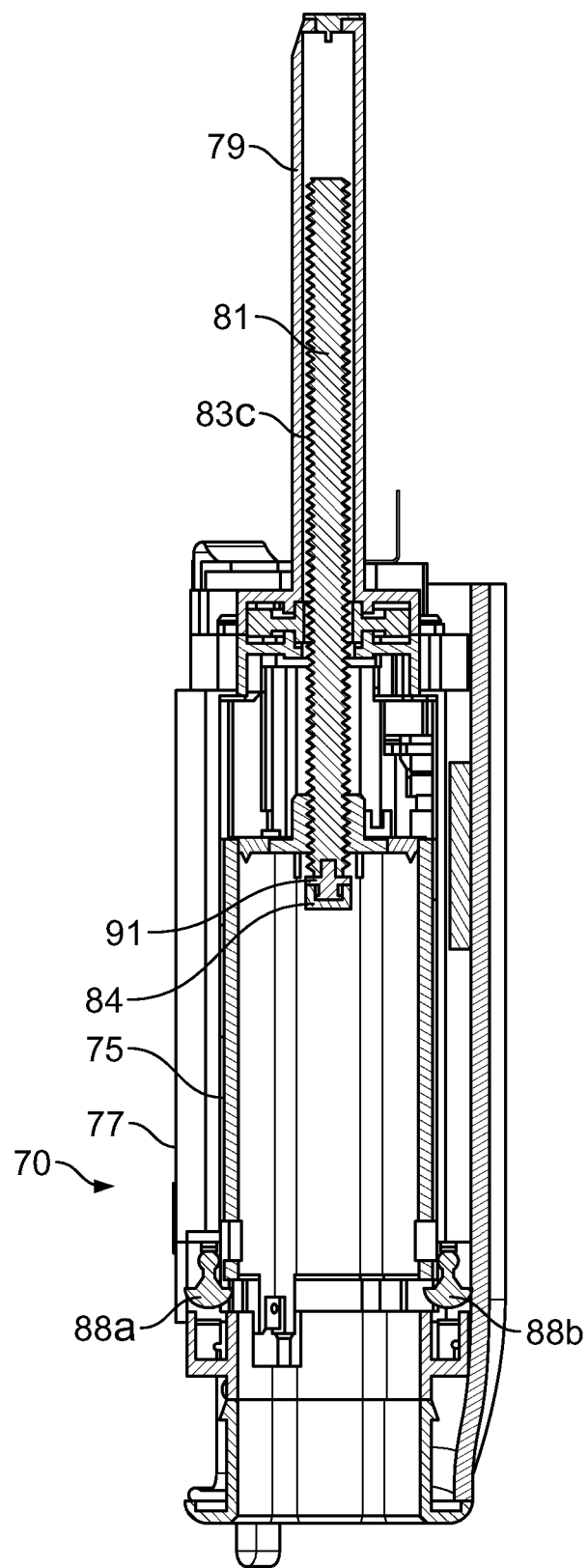
FIGS. 39a to 39i are sectional views showing sequential use steps of a first drive unit of FIGS. 31 and 32 with a fourth cassette unit of FIGS. 10 to 12.
Figure 39B:
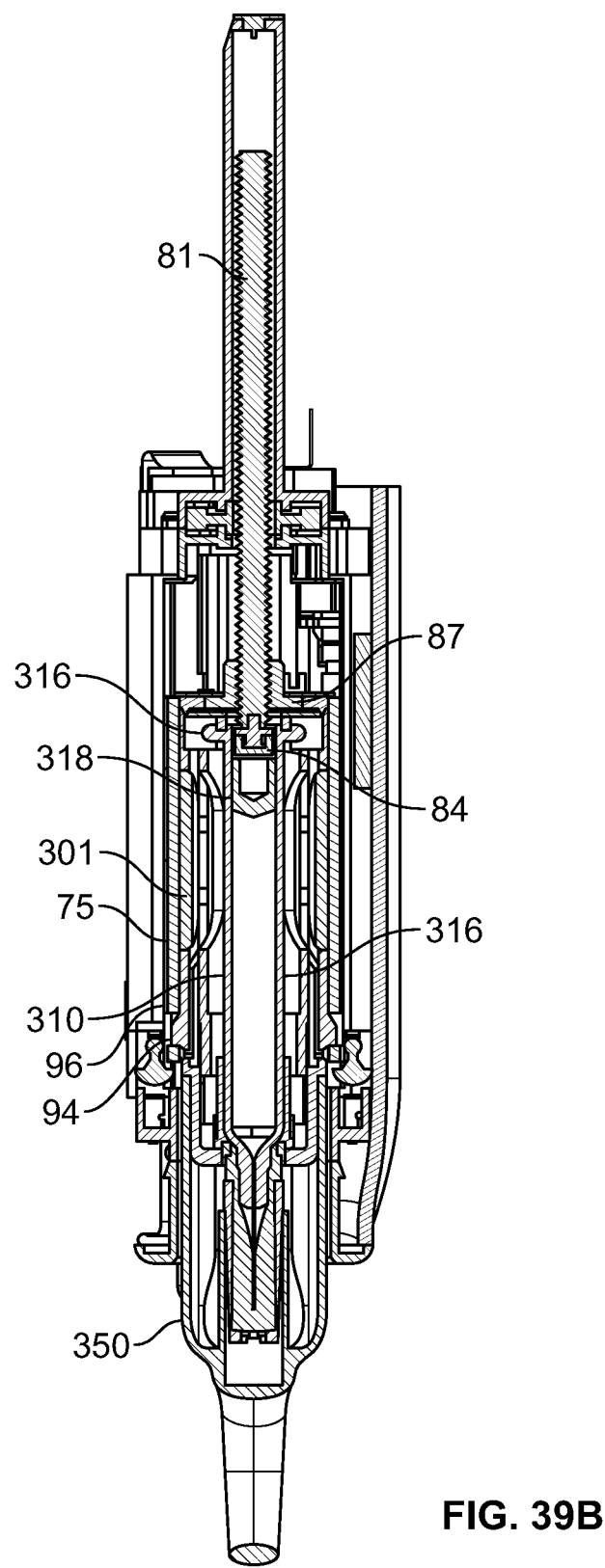
Figure 39C:
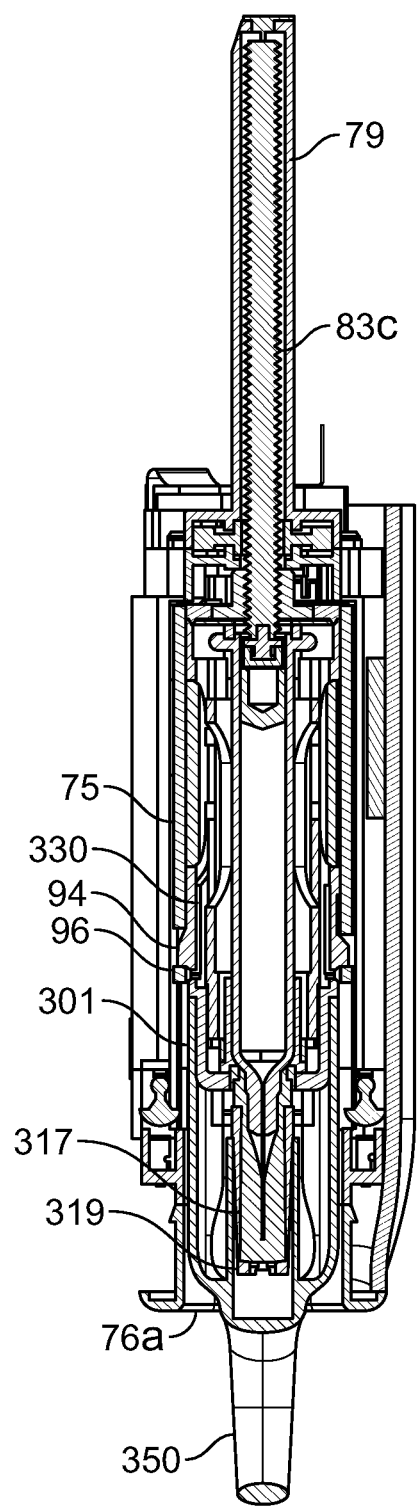
Figure 39D:
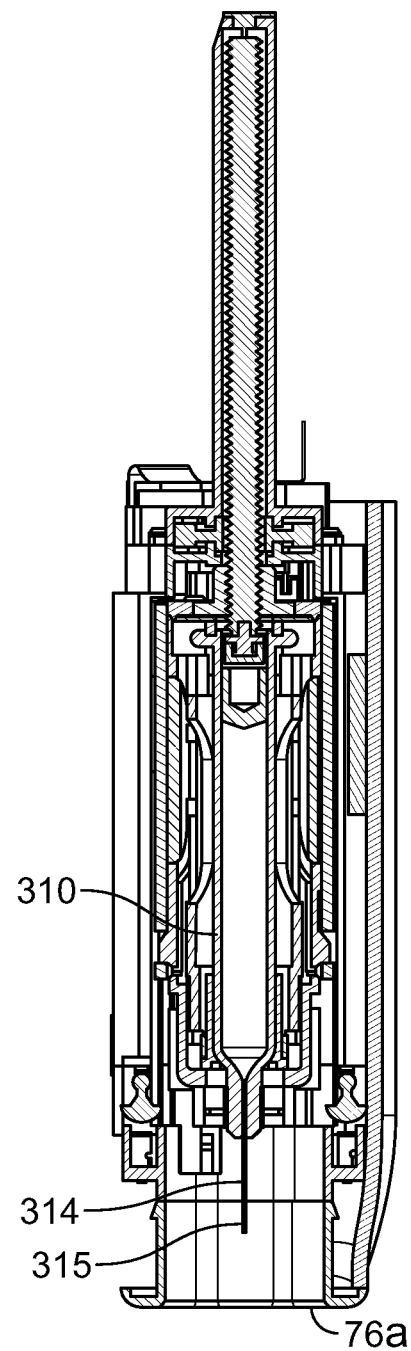
Figure 39E:
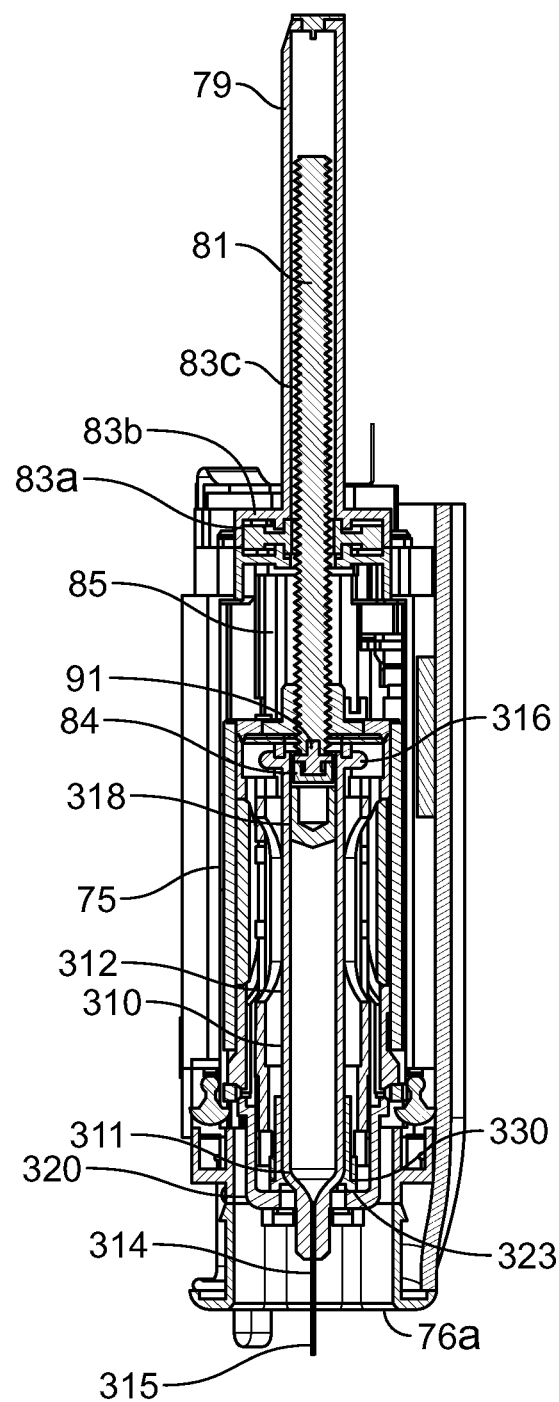
Figure 39F:
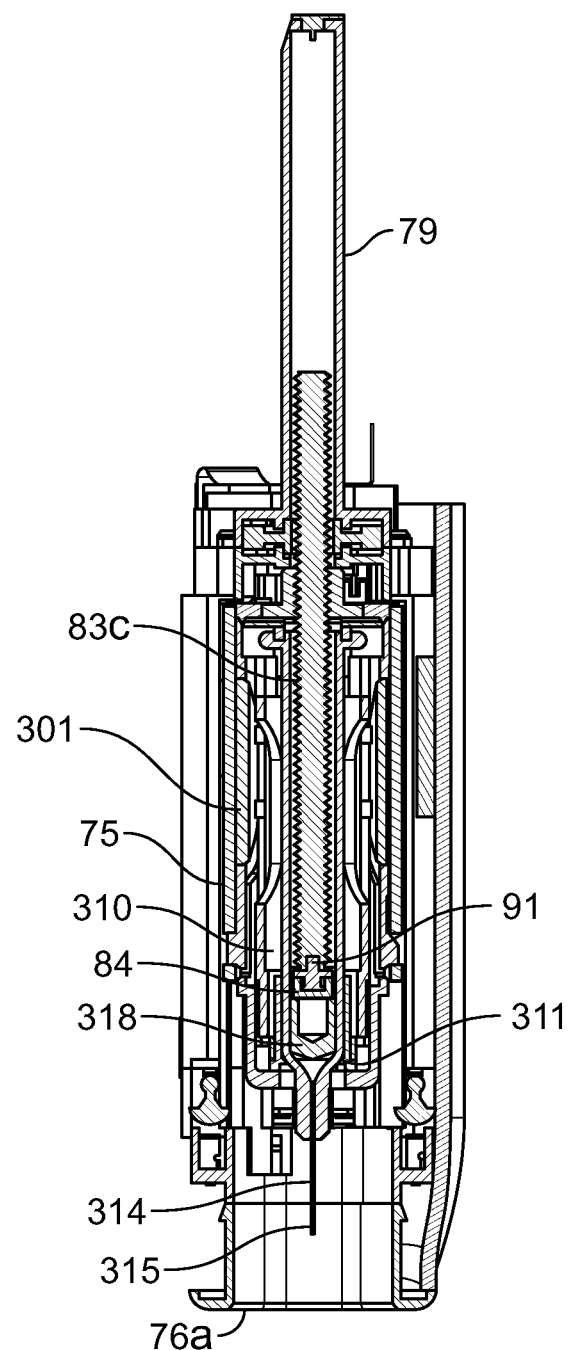
Figure 39G:
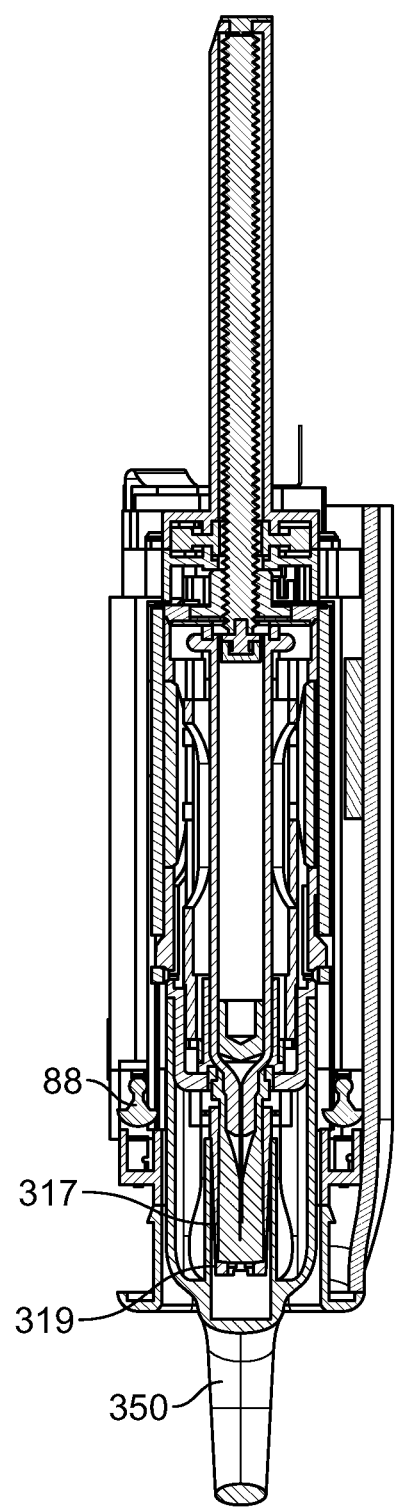
Figure 39H:
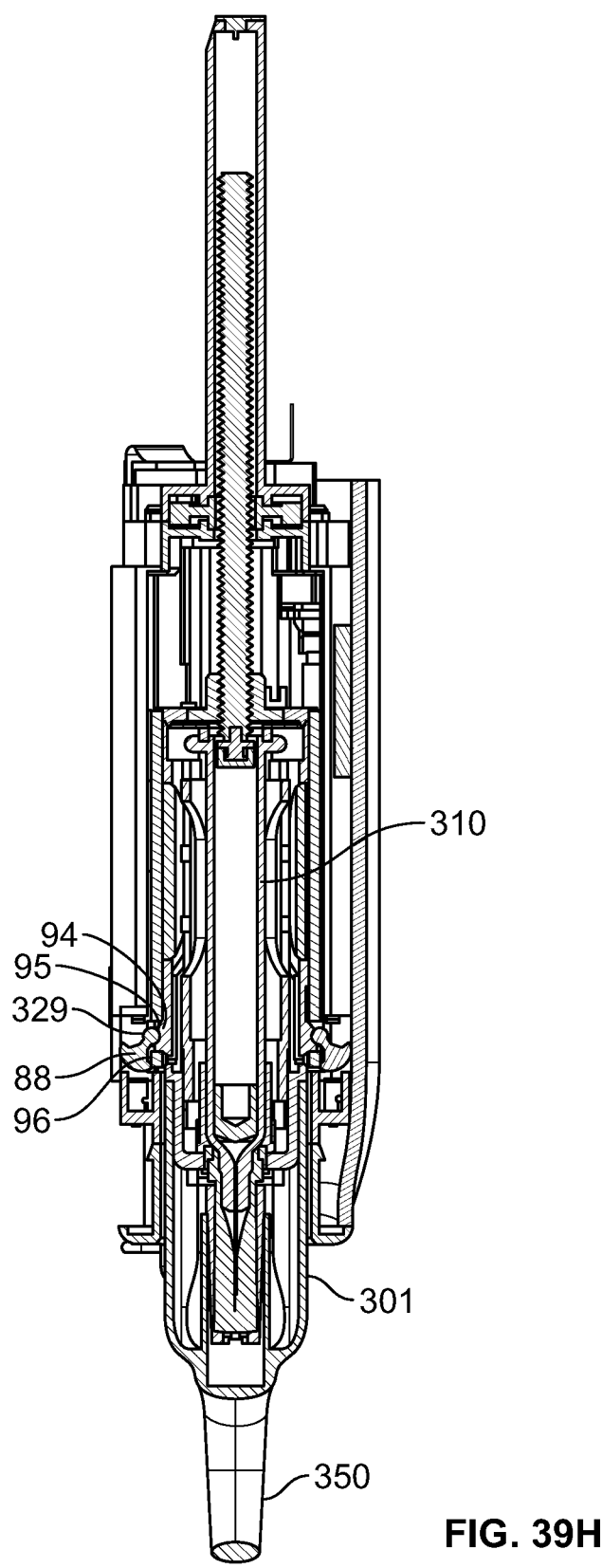
Figure 39I:
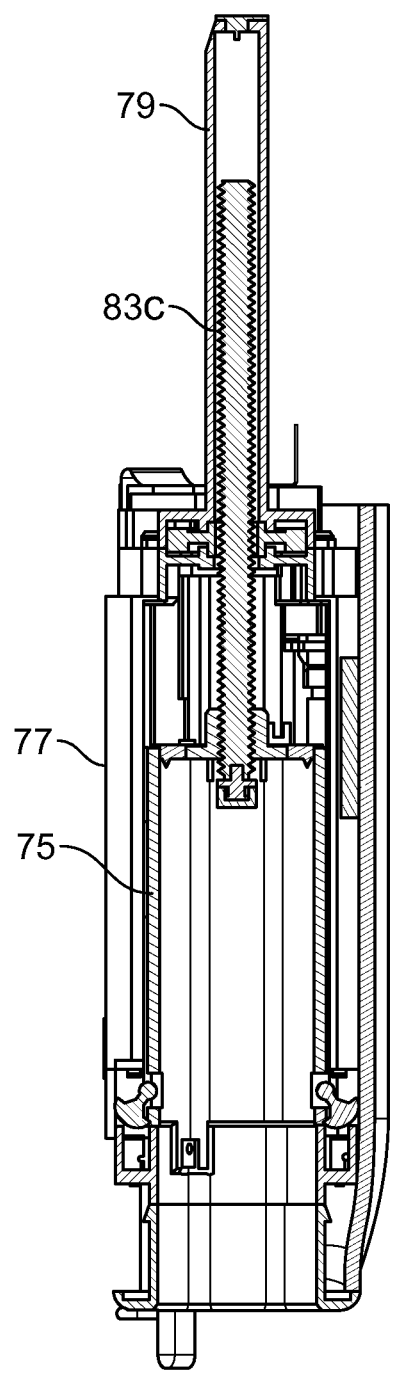
Figure 40A:
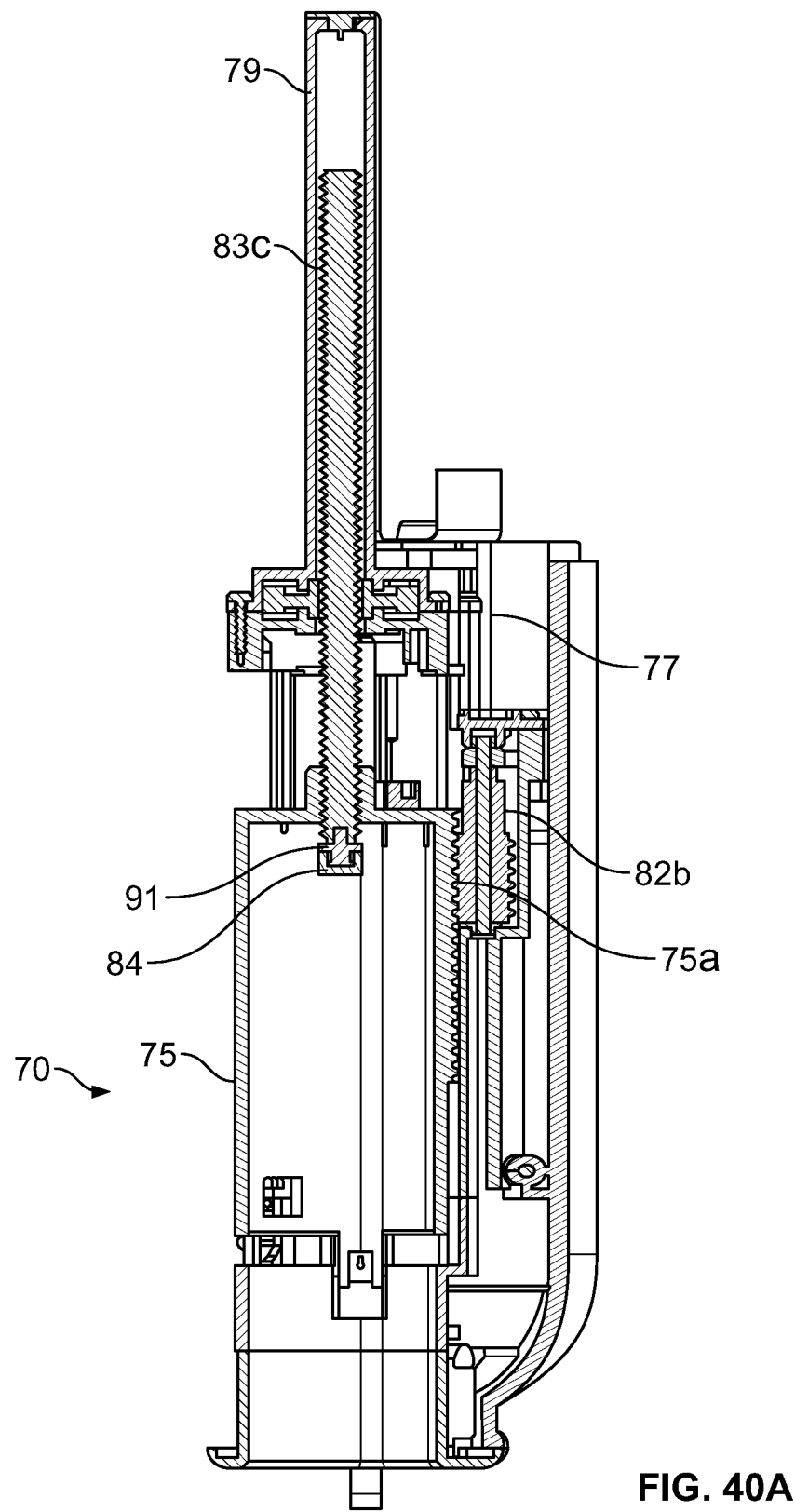
FIGS. 40a to 40i are sectional views showing sequential use steps of a first drive unit of FIGS. 31 and 32 with a fourth cassette unit of FIGS. 10 to 12, but with the view rotated 90° compared to those views of FIGS. 39a to 39i.
Figure 40B:
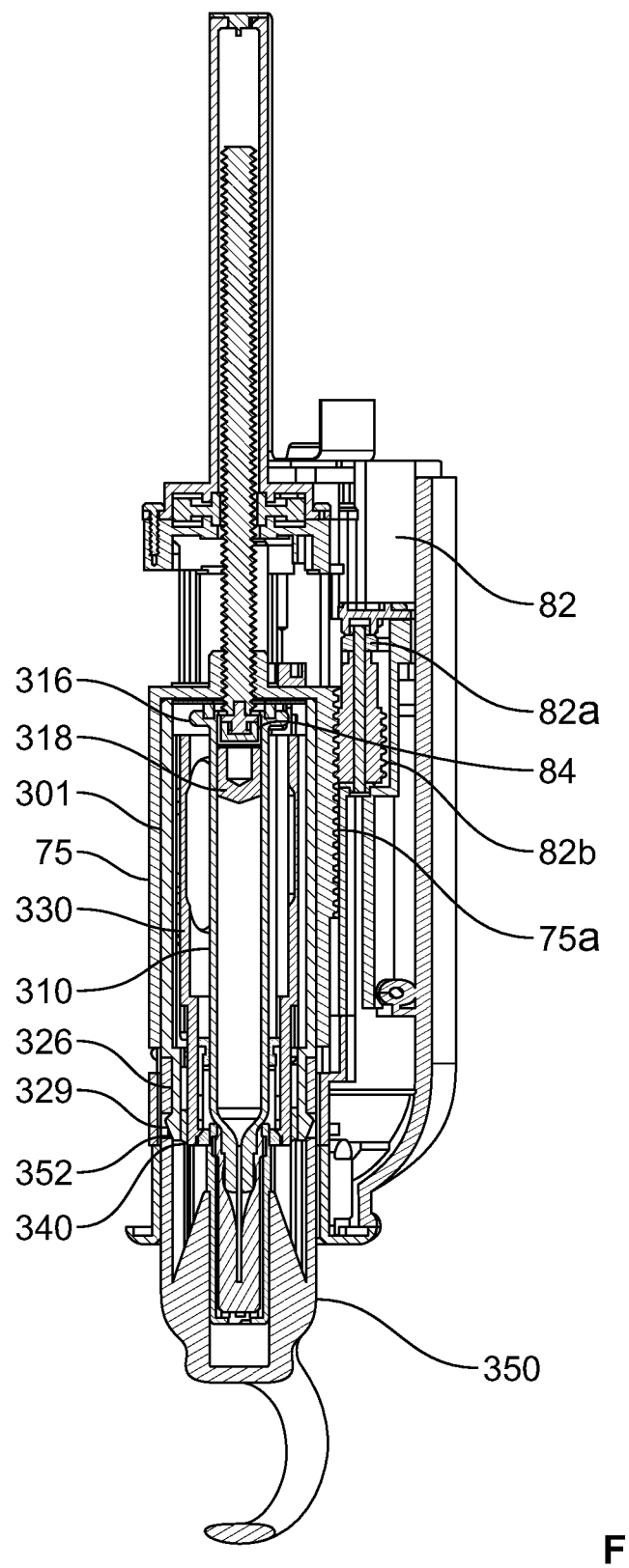
Figure 40C:
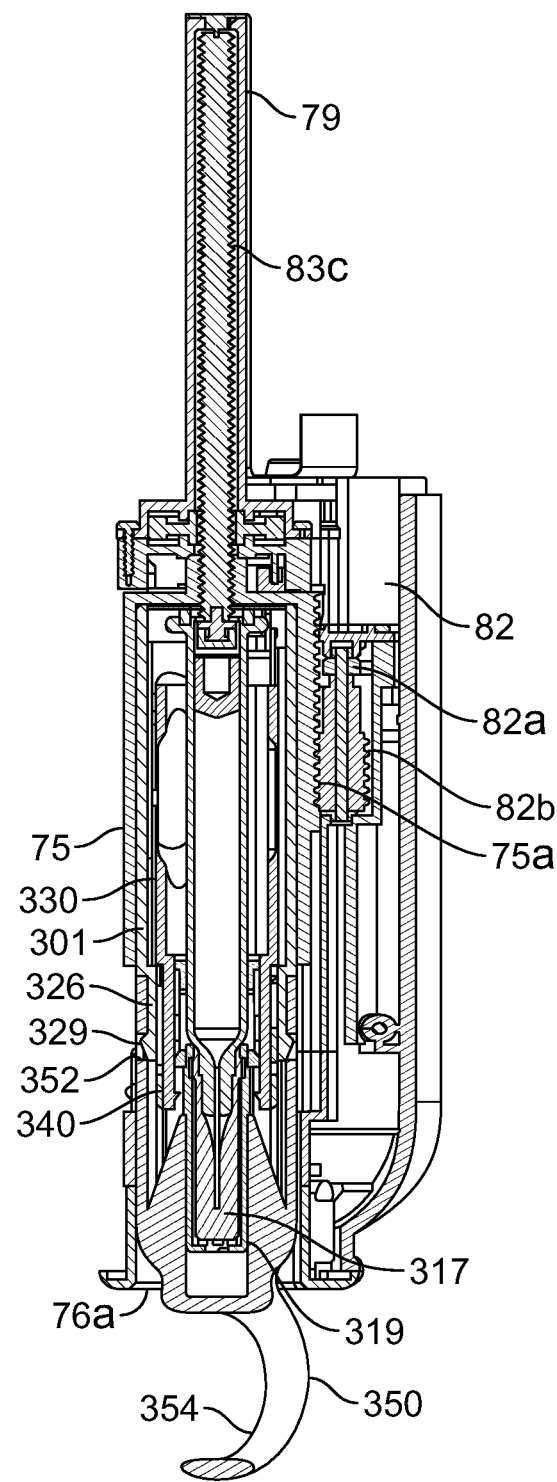
Figure 40D:
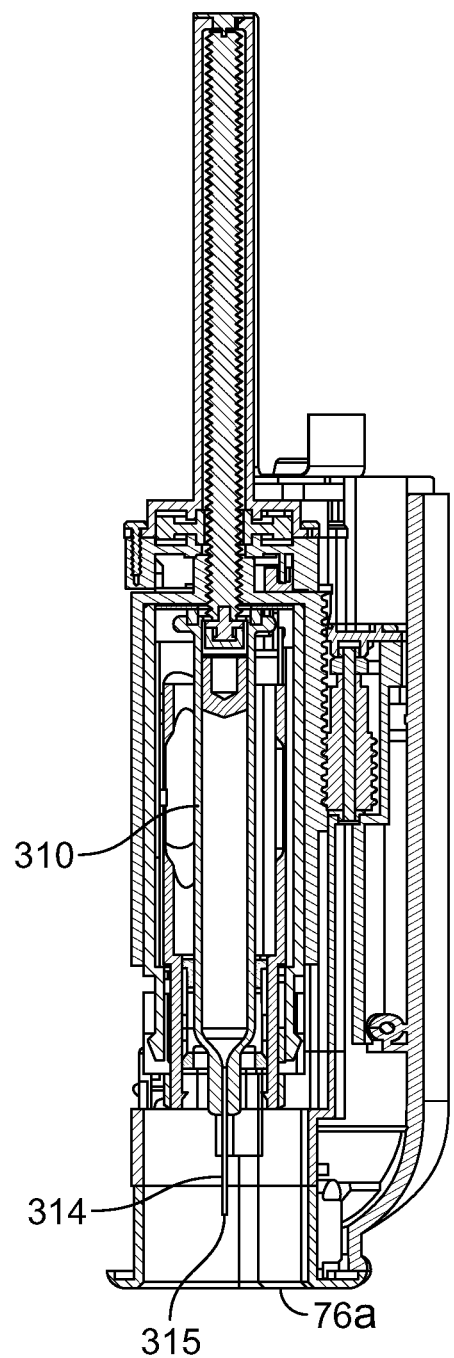
Figure 40E:
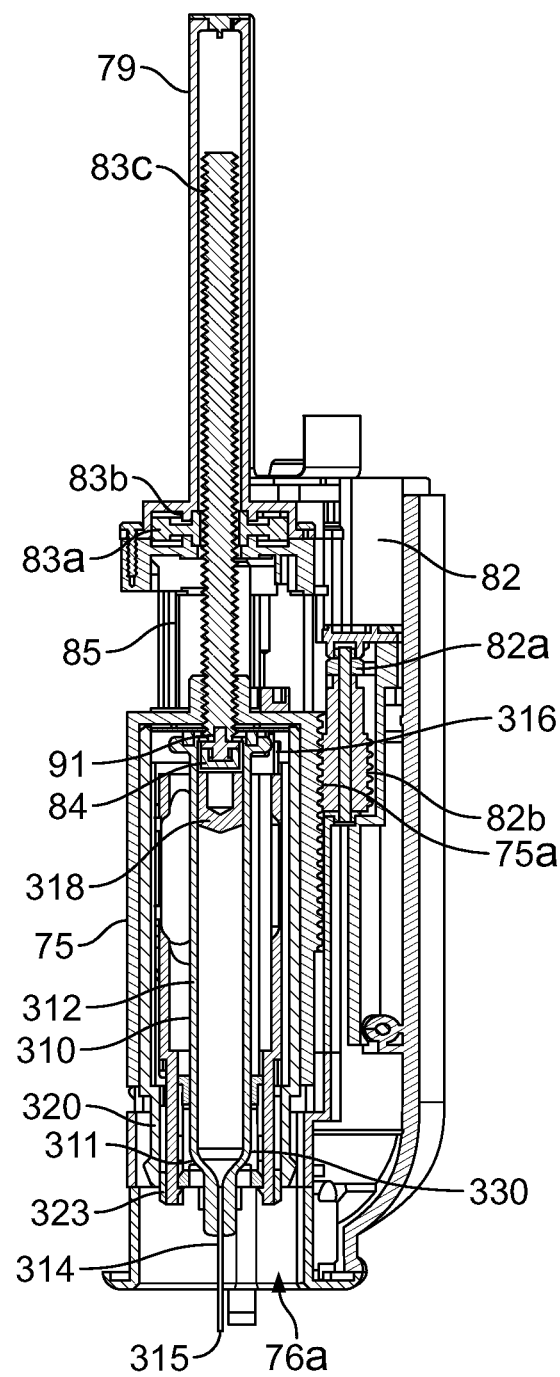
Figure 40F:
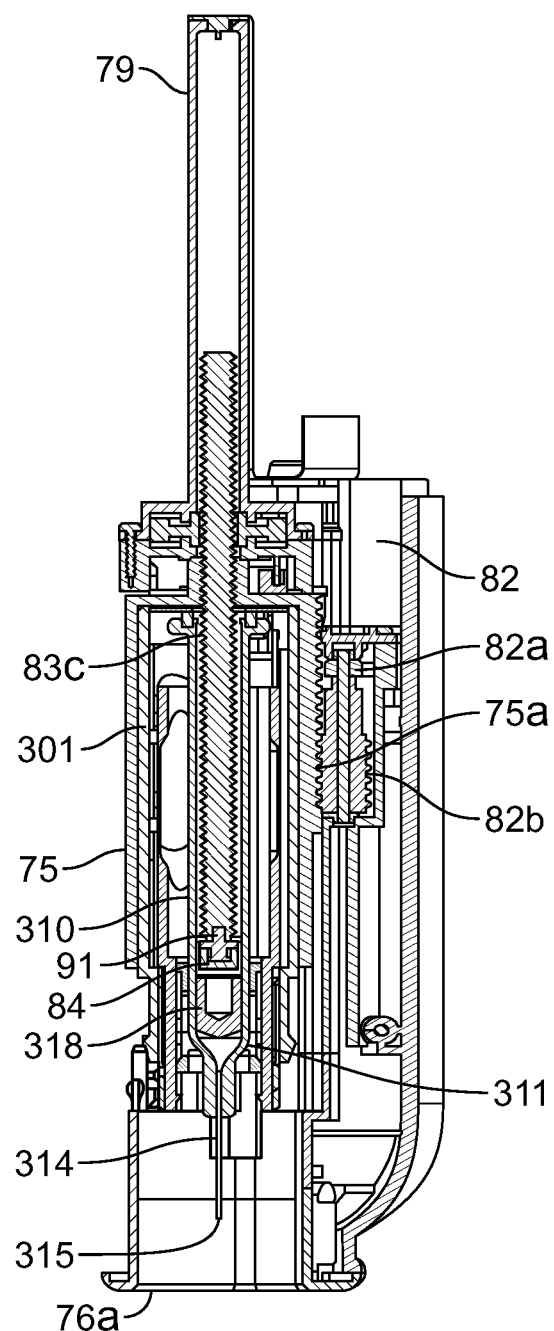
Figure 40G:
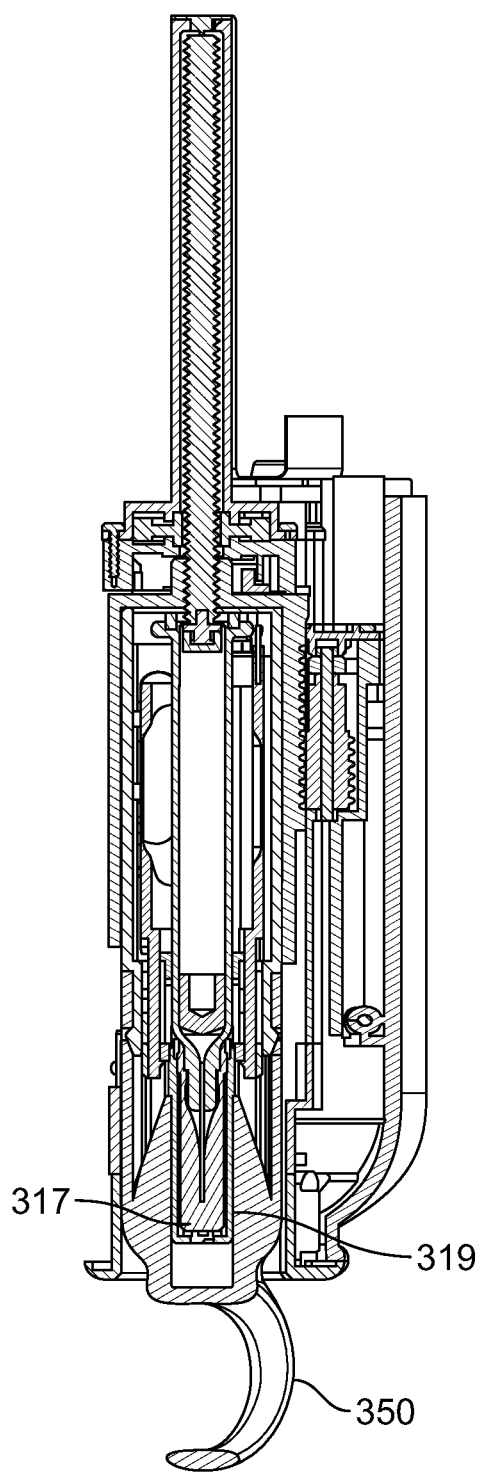
Figure 40H:
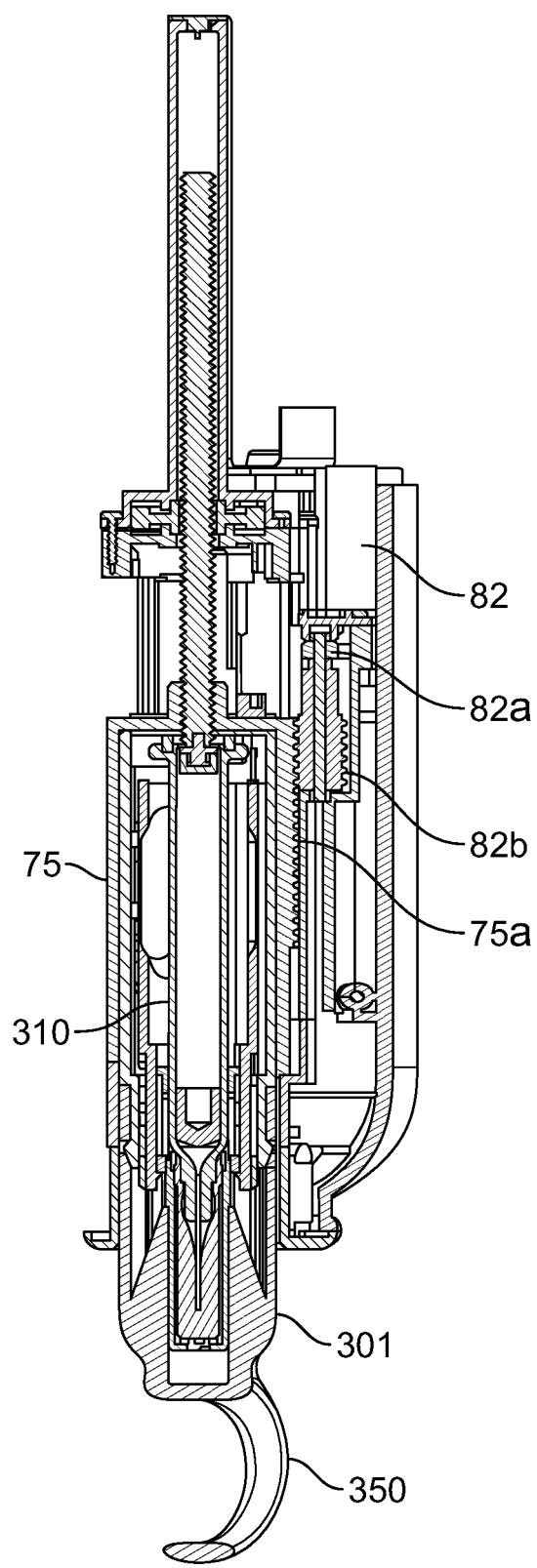
Figure 40I:
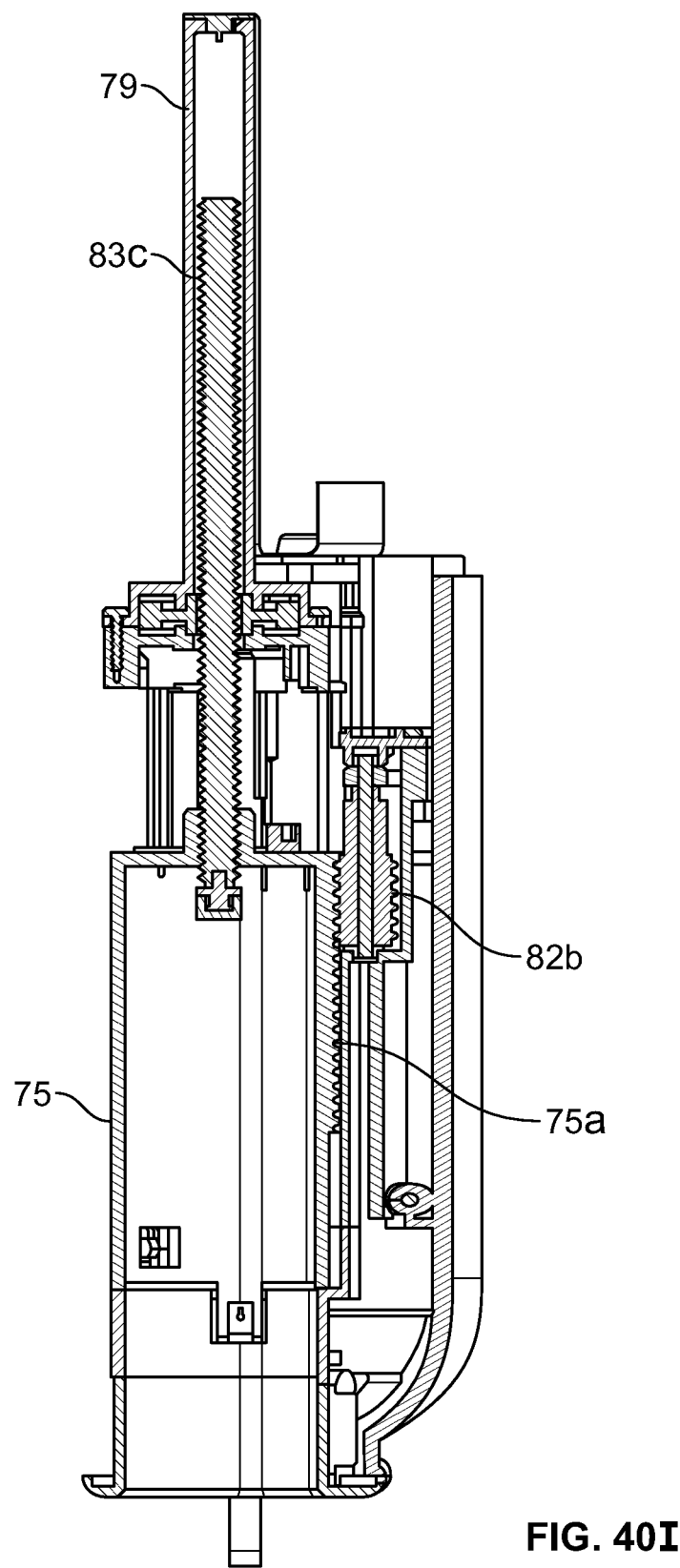

Initially, the auto-injector device is in the 'powered down' state as shown at FIGS. 39i and 40i, to which it returns after completion of a full use sequence, as described hereinbelow.

In a first stage of a typical use operation and to prepare for use of the device, the user hits the power on button 1076 and thereby turns the electronic control system 1001 on. A 'welcome message' is displayed on the screen 72; 1070 (see FIGS. 29 and 38), which instructs the user to insert the cassette unit 301.

After power on, the auto-injector device adopts the configuration as shown at FIGS. 39a and 40a, in which the drive unit 70 is initially in the 'cassette receipt' position. The cassette unit holder 75 is in the 'cassette receipt' position within frame 77. First drive transfer element in the form of worm drive 82b for movement of the cassette unit holder 75 sets it in the 'cassette receipt' position interacting (as visible in FIG. 40a only) with rack 75a provided along one side of the cassette holder. Second drive transfer element in the form of threaded screw 83c located within cover 79, the threaded screw 83c serving as a plunger rod 81 (FIG. 39a), for plunging movement of the plunger 318 of the syringe 310 is in its 'at rest' position. The cassette unit 301 contains a syringe including a syringe plunger 318 that interfaces with the plunger rod 81 upon activation for delivering medication.

Forward end of the threaded screw 83c is provided with narrow tipped end-piece 91 arranged for receipt as an insert to the rear end of the slaving part 84 that is in turn, arranged to seat against the rear end of the syringe plunger 318. The general function of the narrow tipped end-piece 91 of the threaded screw is to give rise to a point load instead of a face load. The slaving part 84 is made of a hard material, thus acting to reduce friction and torsion loads on the system. The slaving part 84 is arranged to function such that when a load is applied to its top face the load is evenly transmitted directly into the syringe plunger 318. In embodiments, the slaving part 84 is brightly-coloured and performs a second function of providing an easy-to-identify visual indicator of the position of the plunger 318 within the syringe 310 so that the patient can visually confirm the drug had been fully injected. Sprung-loaded cassette unit-unlock cams 88a, 88b, the function of which will be described later, are also in their 'at rest' positions.

In a second stage of a typical use operation, as shown at FIGS. 39b and 40b, the user inserts cassette unit 301 comprising syringe 310 and having removable cap 350 to the intermediate pre-docking position within the cassette unit holder 75 of the drive unit 70. In this position slaving part 84 seats up against syringe plunger 318 at the rear flange 316 end of the syringe 310.

As shown at FIG. 39b, in the intermediate pre-docking position the cassette unit 301 is locked into the cassette unit holder 75. Thus, flexible locking arms 94 of the cassette locate within locking apertures 96 of cassette unit holder 75. FIG. 39b also shows a port 87 that is disposed on the cassette unit 301 near the proximal region of the syringe 310. The port 87 is shaped and sized to receive the plunger rod 81 that is installed on the drive unit. In certain implementations, the port 87 defines a passageway into the cassette unit 301 through which the plunger rod 81 advances to drive the plunger 318 within the barrel 312 of the syringe 310. FIG. 28a shows a cross sectional view of an embodiment of the port 87. As shown, the port 87 includes a distal leg 99 that is received within the flange 316 of the syringe 310. The port 87 also includes an inner rim 97 for receiving the plunger rod 81 (FIG. 39b) and a top surface 103 that engages a distal portion of the drive unit. When the cassette unit 301 is mated to the drive unit 70, the plunger rod 81 of the drive unit 70 enters the port 87 to engage the syringe plunger 318 housed within the syringe 310.

As shown at FIG. 40b, in the intermediate pre-docking position, the removable cap 350 is in the cap locked position (also see FIG. 28a). Thus, cap-lock ring 340 of the inner housing sleeve 330 seats up against the inner face of locking arm 326, thereby preventing any inwards movement thereof and so effectively also thereby, preventing any disengagement of the angled tip 329 of that locking arm 326 from its through-hole 352.

Verification of the cassette unit 301 occurs at this intermediate pre-docking position. Thus, RFID reader 73; 1050 (see FIGS. 32 and 38) of the drive unit interrogates RFID tag 21 (see FIG. 3) of the cassette unit 301 and thereby, reads verification information from the RFID tag 21 of the cassette unit 301. Such verification can for example, be for the purpose of checking of drug and dosage information, checking that the drug is not past its expiry date and/or checking that the cassette unit 301 has not been used previously.

Upon positive verification of the cassette unit 301, the cassette unit holder 75 and cassette unit 301 are drawn further up (i.e. transported) into the drive unit 70 to the docking position of third stage of a typical use operation of FIGS. 39c and 40c. Such drawing up is achieved by the drive action of worm drive 82b on rack 75a of the cassette unit holder. The worm drive 82b receives axial drive from first motor 82; 1042 via gear 82a in response to a command from motor drive circuits 1042 acting under the control of motor control MCU 1040, which in turn communicates with main MCU 1010.

It will be noted that in the docking position, the threaded screw 83c has been drawn deeper into its cover 79. It will also be noted that end-ring 354 of removable cap 350 still protrudes out with the exit aperture 76a of drive 70, but otherwise the cassette unit 301 is fully within the drive unit 70.

As shown at FIG. 40c, in the docking position, the removable cap 350 is in the cap-unlocked state (also see FIG. 28b). Thus, inner housing sleeve 330 may be seen to have been moved relative to the cassette unit 301 to a position in which cap-lock ring 340 of the inner housing sleeve 330 no longer seats up against the inner face of locking arm 326. As a result, inwards movement of the locking arm 326 is no longer prevented and disengagement of the tip 329 of the locking arm 326 from its through-hole 352 is achievable by suitable inwards pushing action on the tip 329/locking arm 326. Such inward pushing action on the locking arm 326 is achievable by pulling the cap 350 away from the cassette unit 301, which results in the angled tip 329 interacting with the wall edges of the through-hole 352 to push the locking arm 326 inwards.

The screen 72; 1070 now displays an instruction to the user to remove the cap 350 of the cassette unit 301. The drive unit 70 is provided with a timer function 1090, which is initiated by the removal of the removable cap 350 from the cassette unit 301. Cap removal sensing means 1082 are provided to detect removal of the removable cap 350 from the cassette unit 301. The timer 1090 then starts counting. In embodiments, once the timer 1090 reaches a certain, pre-determined count a command to prevent the drive function 80 of the drive unit 70 is generated. Drive action of the drive unit 70 is thus, prevented. The timer therefore acts as a safety measure to ensure that drug is delivered to the patient within a set time limit following removal of the removable cap 350 from the cassette unit 301.

In a fourth stage of a typical use operation, as shown at FIGS. 39d and 40d, the user has removed the cap 350 together with needle cover 317 and rigid needle shield 319. The needle 314 with tip 315 of the syringe 310 is now uncovered, but still shrouded by the drive unit 70 and does not protrude from the exit aperture 76a thereof. The screen 72; 1070 now displays an instruction to the user to place the device (i.e. the exit aperture 76a thereof) against the injection site. Once the exit aperture 76a has been placed against the injection site electrodes 1085a, 1085b of capacitive touch sense controller (e.g. skin sensor) register the correct placing of the device at the injection site. The screen 72; 1070 now displays an instruction to the user to initiate the injection by pressing the 'inject' button. In other embodiments, such initiation of the injection may be configured to occur automatically on sensing of the correct placing of the device at the injection site.

In a fifth stage of a typical use operation, as shown at FIGS. 39e and 40e, the syringe 310 has now been advanced to the injection position, in which the tip 315 of the needle 315 protrudes out with the exit aperture 76a. Such advancement of the syringe 310 has been achieved by forward movement of the cassette unit holder 75, which is responsive to the forward driving action of worm drive 82b on rack 75a of the cassette unit holder 75. The worm drive 82b receives axial drive from first motor 82; 1042 via gear 82a in response to a command from motor drive circuits 1042 acting under the control of motor control MCU 1040, which in turn communicates with main MCU 1010. It will also be noted that in the injection position, the threaded screw 83c has been drawn forwards and slightly from its cover 79.

Once the syringe 310 is at the injection position of FIGS. 39e and 40e, ejection of drug from the syringe barrel 312 can commence. Such ejection in response to forward advancement of threaded screw 83c responsive to geared driving by gears 83a, 83b, which receive axial drive from second motor 85; 1046 in response to a command from motor drive circuits 1042 acting under the control of motor control MCU 1040, which in turn communicates with main MCU 1010. Threaded screw 83c via end-piece 91 acts on slaving part 84 such that forward advancement thereof results in forward moving of that slaving part 84, which in turn results in plunging movement of the plunger 318 within the barrel 312 of the syringe 310 to expel the drug formulation contents through the tip 315 of the needle 314 and into the injection site (e.g. skin of the user). The slaving part 84 functions such that when a driving load is applied to its top face by end-piece 91 of threaded screw 83c the load is evenly transmitted directly into the syringe plunger 318.

To reduce the risk of the syringe 310 shattering under the loads associated with injecting the drug, it is important for a majority of the load path to travel through the forward shoulder 311 of the syringe barrel 312 and lesser load to pass through the flange 316 at the rear end thereof. It may therefore be seen that forward shoulder 311 of the syringe 310 is surrounded by an annular shoulder support ring 330, which seats against the forward end of the inner wall 323 of the cassette unit housing 320. Information related to the progress of the injection may be displayed on the screen 72; 1070 including for example, a signal that 'injection has been completed successfully'.

In a sixth stage of a typical use operation, as shown at FIGS. 39f and 40f, post-completion of the injection, the needle 314 with tip 315 of the syringe 310 has been withdrawn back into the drive unit 70 into the removable cap unlocking position. Such withdrawal of the syringe 310 is achieved by rearwards movement of the cassette unit holder 75, which is responsive to the rearward driving action of worm drive 82b on rack 75a of the cassette unit holder 75. The worm drive 82b receives axial drive from first motor 82; 1042 via gear 82a in response to a command from motor drive circuits 1042 acting under the control of motor control MCU 1040, which in turn communicates with main MCU 1010.

It will be noted in the post-injection position of FIGS. 39f and 40f that threaded screw 83c with end-piece 91 has been advanced forward sufficiently to drive both slaving part 84 and the plunger 318 within the barrel 312 of the syringe 310 fully forwards. Thus, the leading end of the plunger 18 locates adjacent to the neck 311 of the syringe 310. The slaving part 84 is brightly-coloured and performs a secondary function of providing an easy-to-identify visual indicator of the position of the plunger 318 within the syringe 310 so that the patient can visually confirm the drug had been fully injected. The screen 72; 1070 now displays a message instructing the user to replace the cap 350.

In a seventh stage of a typical use operation, as shown at FIGS. 39g and 40g, the cap 350 with needle cover 317 and rigid needle shield 319 has now been replaced on the cassette unit 301 following completion of the injection procedure. At this stage, the cassette unit 301 is still in locked engagement with the cassette unit holder 75 and removal of the cassette unit 301 is therefore not possible. Threaded screw 83c with end-piece 91 has been withdrawn to the 'at rest' position.

In an eighth stage of a typical use operation, as shown at FIGS. 39h and 40h, the cassette unit holder 75 and cassette unit 301 carried thereby have been moved to a cassette unlock position forward of the 'cassette receipt' position of FIGS. 39b and 40b. Such return is achieved by the drive action of worm drive 82b on rack 75a of the cassette unit holder. The worm drive 82b receives axial drive from first motor 82; 1042 via gear 82a in response to a return command from motor drive circuits 1042 acting under the control of motor control MCU 1040, which in turn communicates with main MCU 1010.

As the cassette unit holder 75 is returned forwards the leading edge thereof interacts with sprung-loaded cassette unit-unlock cams 88 (only one labeled) to move them from their 'at rest' to 'actuated' positions. When in the 'actuated' position the rounded head 89 of cam 88 presses on engaging tip 95 of locking arm 94 to move that locking arm 94 out of locking engagement with the locking aperture and thus, to allow the cassette unit 301 to be released from the cassette unit holder 75.

The screen 72; 1070 now displays a message instructing the user to remove the cassette unit 301 from the drive unit 70. The user accordingly removes the cassette unit 301 to leave the drive 70 in the cassette unlock position as shown at FIGS. 39i and 40i, which remains when the device is turned off.

The screen 72; 1070 then displays a message confirming that the cassette removal operation is complete. A battery check and/or data communication step may also be performed. The user then hits the power button to turn the drive unit off and the drive unit is stowed in cassette unlock position until powered-up for a subsequent injection operation.

The auto-injector of the invention is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the auto-injector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-1R, IL-2, IL-3, IL-4, IL-5, IL-6, IL-13, IL17, interferon (IFN)-α, IFN-β, IFN-γ, granulocyte monocyte colony stimulating factor, tumour necrosis factor-α; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')$_2$ fragments. Polymeric derivatives of such proteins, polypeptides and oligopeptides include derivatives formed between the protein, polypeptide or oligopeptide and a naturally occurring or synthetic polymer, e.g. a polysaccharide or a polyalylklene polymer such as a poly(ethyleneglycol) [PEG] or derivative thereof, e.g. methoxypoly(ethyleneglycol) [mPEG]. Particular agents include growth hormones and hormones for the treatment of infertility. Other particular agents are for the treatment of epilepsy such as brivaracetam and seletracetam.

The auto-injector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

The auto-injector device herein has been found to be of particular utility wherein the concentration of the drug (e.g. a therapeutic biologic type drug) in the liquid drug formulation is quite high. In particular, where the drug is a pegylated antibody the auto-injector device has been found to be of particular utility wherein the concentration of the drug is greater than 100 mg/ml, particularly greater than 150 mg/ml such as 200 mg/ml.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:
1. An auto-injector comprising:
  a cassette unit comprising:
    a cassette unit housing defining a cassette unit housing cavity and a needle projection aperture, said cassette unit housing cavity arranged for receipt of a syringe comprising:
      a barrel for containing a volume of a liquid drug formulation;
      a hollow needle at a front end of said barrel, said hollow needle defining a needle tip for dispensing of said liquid drug formulation; and
      a plunger that is axially movable within the barrel;
    a removable cap that fits over and thereby, acts such as to close off, the needle projection aperture; and
    connecting to said removable cap, a needle cover defining a needle sheath for sheathing of said needle tip; and
  a drive unit, separate from and arranged for receipt of the cassette unit, comprising:
    a drive unit housing defining a docking cavity and a needle delivery aperture, wherein said docking cavity is arranged for docking receipt of the cassette unit at a docking position, whereupon said cassette unit and/or said syringe is movable from a rest position, in which the needle tip of the syringe is within the drive unit housing to a use position, in which the needle tip protrudes from said needle delivery aperture;
    a drive arrangement, said drive arrangement comprising:
      one or more electrically powered sources of axial drive;
      a first drive transfer element for transferring said axial drive to the cassette unit and/or to the syringe for advancing the syringe to said use position; and
      a second drive transfer element for subsequently transferring the axial drive to said plunger of the syringe for moving the plunger into the barrel of the syringe to eject at least part of said volume of liquid drug formulation;
    an electronic control system, in the drive unit housing, comprising a microprocessor control unit including a timer; and
    a cap detect switch in the drive unit housing, in communication with said microprocessor control unit, for detecting removal of the removable cap and needle cover from the cassette unit,
  wherein, on removal of the removable cap and needle cover from the cassette unit, said cap detect switch communicates with the timer to send a cap removal detection signal to the timer to initiate a time count, and
  wherein the timer is arranged such that on reaching a certain, pre-determined time count a stop command to stop the drive functioning of the drive unit is generated.

2. An auto-injector according to claim 1, wherein said stop command is to disable said one or more electrically powered sources of axial drive.

3. An auto-injector according to claim 1, wherein said stop command is to initiate a blocking function that acts to block the movement of said first and/or second drive transfer elements.

4. An auto-injector according to claim 1, wherein the drive unit includes an electronic display and the time count is displayed on the electronic display.

5. An auto-injector according to claim 1, wherein the timer is arranged such that on reaching said certain, pre-determined time count an alarm command to initiate an audible alarm of the drive unit is generated.

6. An auto-injector according to claim 1, wherein the removable cap is provided with a connector defining one or more needle cover gripping elements for gripping the needle cover.

7. An auto-injector according to claim 1, wherein the housing receives a syringe containing a liquid drug formulation.

8. An auto-injector according to claim 7, wherein said liquid drug formulation is arranged for storage at from 2-8° C. and for injected delivery at from 18-30° C.

9. An auto-injector according to claim 8, wherein the liquid drug formulation has a viscosity of less than 120 mPa·s at a delivery temperature of 20° C.

10. An auto-injector according to claim 7, wherein the liquid drug formulation comprises an aqueous formulation of a therapeutic biologic type drug.

11. An auto-injector according to claim 10, wherein said biologic type drug comprises an immunoglobulin or a fragment thereof.

12. An auto-injector according to claim 1, wherein said timer is installed on an integrated circuit chip.

13. An auto-injector drive unit comprising:
- a drive unit housing arranged for docking receipt of an injection cassette unit;
- a drive arrangement for ejecting at least part of a liquid drug formulation from the cassette unit;
- an electronic control system comprising a microprocessor control unit including a timer; and
- a cap detect switch in the drive unit housing, in communication with said microprocessor control, for detecting removal of a removable cap and needle cover from the cassette unit,
- wherein, on removal of the removable cap and needle cover from the cassette unit, said cap detect switch communicates with the timer to send a cap removal detection signal to the timer to initiate a time count, and
- wherein the timer is arranged such that on reaching a certain, pre-determined time count a stop command to stop drive functioning of the drive unit is generated.

14. An auto-injector drive unit according to claim 13, wherein said stop command disables one or more electrically powered sources of drive.

15. An auto-injector drive unit according to claim 13, wherein said stop command initiates a blocking function that acts to block movement of drive transfer elements.

16. An auto-injector drive unit according to claim 13, wherein the drive unit includes an electronic display and the time count is displayed on the electronic display.

17. An auto-injector drive unit according to claim 13, wherein the timer is arranged such that on reaching said certain, pre-determined time count an alarm command to initiate an audible alarm of the drive unit is generated.

* * * * *